(12) United States Patent
Wallach et al.

(10) Patent No.: US 8,236,507 B2
(45) Date of Patent: *Aug. 7, 2012

(54) MODULATORS OF TNF RECEPTOR ASSOCIATED FACTOR (TRAF), THEIR PREPARATION AND USE

(75) Inventors: David Wallach, Rehovot (IL); Nikolai Malinin, Rehovot (IL); Mark Boldin, Rehovot (IL); Andrei Kovalenko, Rehovot (IL); Igor Mett, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 372 days.

This patent is subject to a terminal disclaimer.

(21) Appl. No.: 12/365,136

(22) Filed: Feb. 3, 2009

(65) Prior Publication Data

US 2009/0291888 A1 Nov. 26, 2009

Related U.S. Application Data

(63) Continuation of application No. 09/155,676, filed as application No. PCT/IL97/00117 on Apr. 1, 1997, now Pat. No. 7,485,456.

(30) Foreign Application Priority Data

Apr. 2, 1996 (IL) .......................................... 117800
Aug. 26, 1996 (IL) .......................................... 119113

(51) Int. Cl.
*C12Q 1/68* (2006.01)
*C12P 21/06* (2006.01)
*C07K 1/00* (2006.01)

(52) U.S. Cl. ....................... 435/6.17; 435/69.1; 530/350
(58) Field of Classification Search ........................ None
See application file for complete search history.

(56) References Cited

U.S. PATENT DOCUMENTS

| | | | |
|---|---|---|---|
| 5,641,876 A | 6/1997 | McElroy et al. | |
| 5,804,412 A | 9/1998 | Gill et al. | |
| 5,843,721 A | 12/1998 | Rothe et al. | |
| 5,844,073 A | 12/1998 | Rothe et al. | |
| 7,485,456 B1 * | 2/2009 | Wallach et al. | 435/325 |

FOREIGN PATENT DOCUMENTS

WO PCT/9706182 2/1997

OTHER PUBLICATIONS

Marshall, Science. Aug. 25, 1995;269(5227)1050, 1052-5.*
Nyberg et al. Molecular Therapy, vol. 10, No. 6, pp. 976-980, 2004.*
Mosialos et al., "The Epstein-Barr Virus Transforming Protein LMP1 Engaging Signaling Proteins for the Tumor Necrosis Factors Receptor Family", *Cell* 80:389-399, (1995).
Cheng, et al, "Tank, aco-inducer with TRAF2 of TNF- and CD40L-mediated NF-KB activation", (1995).
Vandenabeele et al., Two tumor necrosis factors receptor: structure and function:, 399, (1995) *Trends in Cell Biology* 5:392-399, 1995.
Malinin et al., "MAP3K-related kinase involved in NF-kB induction by TNF, CD95 (1997) and IL-1", *Nature* 385:540-544.
Rothe et al., "The THRF2-TRAF Signaling Complex Contains Two Novel Proteins Related to Baculoviral Inhibitor of Apoptosis Proteins", *Cell* 83:1243-1252, (1995).
Lee et al., "T cell receptor-dependent cell death of T cell hybridomas mediated by the CD30 cytoplastmic domain in assocation with tumor necrosis factor receptor-associated factors," J Exp Med 183(2):669-674(1996).
Andrea D. Branch, A good antisense molecule is hard to find, TIBS, 47-48, (1998).
Stanley Crooke, Antisense Research and Applications, Chapter 1, Basic Principles of Antisense Therapeutics, Springer-Verlag Press, Berlin, Heidelberg, New York, p. 3. (1998).
W. French Anderson, Human gene therapy, Nature, vol. 392, pp. 25-30, (1998).
Stuart Orkin & Arno Motulsky, Report and Recommendations of the panel to assess the NIH investment in research on gene therapy. NIH web page (http://www.nih.gov), pp. 1-23, (1995).
J. Skolnick et al., TIBECH, "From genes to protein structure and function: novel applications of computational approaches in the genomic era," Jan. 2000, vol. 18, pp. 34-39.
P. Bork, Genome Research, "Powers and Pitfalls in Sequence Analysis: The 70% Hurdle,"2000, pp. 398-400.
T. Doerks et al., TIG, Genetwork, "Protein annotation: detective work for function prediction," Jun. 1998, vol. 14, No. 6, pp. 248-250.
W. French Anderson, Human gene therapy, Nature, vol. 392, pp. 25-30 (Apr. 1998).
Marshall et al. Gene Therapy's Growing Pains (Science, vol. 269, pp. 1050-1055, Aug. 1995).

* cited by examiner

*Primary Examiner* — Janet Epps-Smith
(74) *Attorney, Agent, or Firm* — Browdy and Neimark, PLLC

(57) ABSTRACT

A DNA sequence encoding a protein capable of binding to a tumor necrosis factor receptor-associated factor (TRAF) molecule, TRAF-binding proteins, their isoforms, analogs, fragments and derivatives encoded by the DNA sequence, their methods for the production of the DNA sequences and proteins, and the uses for the DNA sequence and proteins.

9 Claims, 46 Drawing Sheets

```
Length: 1906  July  7, 1996 12:35  Type: N  Check: 7122  ..

1  CATTGGGTCA CGCGGTGGCG GCGCTCTAGA ATAGTGGATC CCCCGGGCTG
 51  CAGGAATTCG ATTCGAGGCC ACGAAGGCCG GCGGCGCGGC GCAnGCACCG
101  GCCCGGGGAn AGGCnCCATG AGCGGATCnC nGAACnATGA CAAAAGACAA
151  TTTCTGCTGG AGCGACTGCT GGATGCAGTG AAACAGTGCC AGATCCGCTT
201  TnGAGGGAGA AAGGAGATTG CCTCGGATTC CGACAGCAGG GTCACCTGTC
251  TGTGTGCCCA GTTTGAAGCC GTCCTGCAGC ATGGCTTGAA GAGGAGTCGA
301  GGATTGGCAC TCACAGCGGC AGCGATCAAG CAGGCAGCGG GCTTTGCCAG
351  CAAAACCGAA ACAGAGCCCG TGTTCTGGTA CTACGTGAAG GAGGTCCTCA
401  ACAAGCACGA GCTGCAGCGC TTCTACTCCC TGCGCCACAT CGCCTCAGAc
451  gTGGGCCGGG GTCGCGCCTG GCTGcGCTGT GCCCTCAACG AACACTCCCT
501  GGAGCGCTAC CTGCACATGC TCCTGGCCGA CCGCTGCAGG CTGAGCACTT
551  TTTATGAAGA CTGGTCTTTT GTGATGGaTG AAGAAAGGTC CAGTATGCTT
601  CCTACCATGG CAGCAGGTCT GAACTCCATA CTCTTTGCGA TTAACATCGA
651  CAACAAGGAT TTGAACGGGC AGAGTAAGTT TGCTCCCACC GTTTCAGACC
701  TCTTAAAGGA GTCAACGCAG AACGTGACCT CCTTGCTGAA GGAGTCCACG
751  CAAGGAGtGA GCAGCCTGTT CAGGGAGATC ACAGcCTcCT cTGCCGTcTC
801  CATCcTCATC AAACCTGAAC AGGAGACCGA CCCTTGCCTG TCGTGTCCAG
851  GAATGTCAGT GCTGATGCCA AATGCAAAAA GGAGCGGAAG AAGAAAAAGA
```

FIG. 3A-1

```
 901  AAGTGACCAA CATAATCTCA TTTGATGATG AGGAAGATGA GCAGAACTCT
 951  GGGGACGTGT TTAAAAAGAC ACCTGGGGCA GGGGAGAGCT CAGAGGACAA
1001  CTCCGACCGC TCCTCTGTCA ATATCATGTC CGCCTTTGAA AGCCCCTTCG
1051  GGCCTAACTC CAATGGAATC AGAGCAGCAA CTCATGGAAA ATTGATTCCC
1101  TGTCTTTGAA CGGGGAGTTT GGGTACCAGA AGCTTGATGT GAAAAGCATC
1151  GAtGAtGAAG ATgTGGATGA AAACGAAGAT GACgTGTATG AAACTCATC
1201  AGGAAGGAAG CACAGGGGCC ACTCGGAGTC GCCCGAGAAG CCACTGGAAG
1251  GGAACACCTg CCTCTCCcAG ATGCACAGCT GGgCtCCGCT GAAGgTgCTG
1301  CaCAaTGACT CCGACATCCT CTTCCCTGTC AGTGGCGTGG gCTCCTACAG
1351  CCCAGCAGAT gCCCCCCTCG GAAGCCTGGA GAACGGGACA GGACCAGAGG
1401  ACCACGTTCT CCCGGATCCT GGACTTCGGT ACAGTGTGGA AGCCAGCTCT
```

FIG. 3A-2

1451 CCAGGCCACG GAAGTCCTCT GAGCAGCCTG TTACTTCTGC CTCAGTGCCA

1501 GAGTCCATGA CAATTAGTGA ACTGCGCCAG GCCACTGTGG CCATGATGAA

1551 CAGGAAGGAT GAGCTGGAGG AGGAGAACAG ATCACTGCGA AACCTGCTCG

1601 ACGGTGAGAT GGAGCACTCA GCCGCGCTCC GGCAAGAGGT GGACACCTTG

1651 AAAAGGAAGG TGGCTGAACA GGAGGAGCGG CAGGGCATGA AGGTCCAGGC

1701 GCTGGCCAGC TATCTTTGCT ATTTTGTGAG GAGATTCTAA CCCCACGTGA

1751 GAACCATGTG GTGGAGAAAT GGAGGGAGAG AGAAATCCAA CAGTTCCTGA

1801 TAGTCTCATT TGAGCTCCTG GATCCAGTCT TTCCTGAAGC TGTGTTTCCT

1851 CTGGACTTTT CATGTATGTG AGCCAATAAA TTGCTTTCAT TCCTTGAAAA

1901 AAAAAA

FIG. 3A-3

```
TRANSLATE of: 9hhh check: 7122 from: 1 to: 1906
generated symbols 1 to: 635.

9hhh.pep  Length: 604  August 23, 1996 15:03  Type: P  Check: 4554

1  XTGPGXGXMS GSXNXDKRQF LLERLLDAVK QCQIRFXGRK EIASDSDSRV

51  TCLCAQFEAV LQHGLKRSRG LALTAAAIKQ AAGFASKTET EPVFWYYVKE

101  VLNKHELQRF YSLRHIASDV GRGRAWLRCA LNEHSLERYL HMLLADRCRL

151  STFYEDWSFV MDEERSSMLP TMAAGLNSIL FAINIDNKDL NGQSKFAPTV

201  SDLLKESTQN VTSLLKESTQ GVSSLFREIT ASSAVSILIK PEQETDPCLS

251  CPGMSVLMPN AKRSGRRKRK *PT*SHLMMR KMSRTLGTCL KRHLGQGRAQ

301  RTTPTAPLSI SCPPLKAPSG LTPMESEQQL MEN*FPVFER GVWVPEA*CE

351  KHR**RCG*K RR*RVWKLIR KEAQGPLGVA REATGREHLP LPDAQLGSAE

401  GAAQ*LRHPL PCQWRGLLQP SRCPPRKPGE RDRTRGPRSP GSWTSVQCGS

451  QLSRPRKSSE QPVTSASVPE SMTISELRQA TVAMMNRKDE LEEENRSLRN

501  LLDGEMEHSA ALRQEVDTLK RKVAEQEERQ GMKVQALASY LCYFVRRF*P

551  HVRTMWWRNG GREKSNSS** SHLSSWIQSF LKLCFLWTFH VCEPINCFHS

601  LKKK
```

FIG. 3B clone 10  Length: 2631  August 23, 1996  17:18  Type: N  Check: 5107 ..

```
   1  CCCcTcTcAC AGCcCAgGCC ATCCAAGAGG GgCTGAGGAA AGAGCCCATC
  51  cACCGcGTGT cTGCAGcGGA GcTGGGAGGG AAGGTGAACC GGGCAcTACA
 101  GCAAGTGGGA GGTcTGAAGA GCCCTTGGAG GGGAGAATAT AAAGAACCAA
 151  GACATCCAcc GCCAAATCAA GCCaAtTACC ACCAGACCcT CcATGCCcAg
 201  CCGAGAGAGc TtTcGCCAAG GGCCCcAGGG CCCCGGCCAg CTGAGGAGAc
 251  AACAggCAGA GCCCcTAAGc TCCAGCcTCC TcTCCCACCA GAGCCCCAG
 301  AGCCaAACAA GTcTCCTCCC ttGACTttGA GCAAGGAGGA GTcTGGGATG
 351  TGGGAACCCT TACcTctGTC cTCCCTGGAG CCAGCCCCTG CCAGAAACCC
 401  CAGcTCACCA GAGcGGAAAG CAACCGTCCC GGAGCAGGAA CTGCAGCAGc
 451  TGGAAATAGA ATTATTCCTC AACAGCCTGT CCCAGcCATT TTcTcTGGAG
 501  GAGCAGGAGC AAATTCTcTc GTGCCTCAGC ATCGACAGCC TCTCCCtGTC
 551  GGATGACAGT GAGAAGAACC CATCAAAGGC CTCTCAAAGC TCGCGGGACA
 601  CCCTGAGCTC AGGCGTACAC TCCTGGAGCA GcAGGCCGA GGcTCGAAGc
 651  TCCAGCTGGA ACATGGTGcT GGCCCGGGgg CGgCCCACCG ACACCCCAAG
 701  CTATTTCAAT GGTGTGAAAG TCCAAATACA GTCTCTTAAT GGTGAACACC
 751  TGCACATCCG GGAGTTCCAC CGGGTCAAAG TGGGAGACAT CGCCACTGGC
 801  ATCAGCAGCC AGATCCCAGC TGCAGCCTTC AGCTTGGTCA CCAAAGACGG
 851  GCAGCCTGTT CGCTACGACA TGGAGGTGCC AGACTCGGGC ATCGACCTGC
 901  AGTGCACACT GGCCCCTGAT GGCAGCTTCG CCTGGAGCTG GAGGGTCAAG
 951  CATGGCCAGC TGGAGAACAG GCCCTAACCC TGCCCTCCAC CGCCGGcTCC
1001  ACACTGCCGG aAAGCAGCCT TCCTGCTCGG tGCACGATGC TGCCCTGaAA
1051  AcACAGGcTC AGCcGTTCCC AgGGgATyTG .CCAGcCCCC cGGcTcArcA
1101  G.tGGGaAcC AGGGcCTcG. CAGC.AGC.A AGGT.gGGGG CAAGC.AGAA
1151  TGCcTCCCAG GATTTcACA. CcTGAGCCC. TGCCCCA.CC cTGcTGaadA
1201  AAAcAyT.CC GCcAcGtGAA GagAcAGaAG GAGGATGG.C AGGAgTt..A
1251  CcTygGGGAA aCaAAAcAGg gaTcTTt.tT cTGcCCcTGc TCCAGT.cGA
```

FIG. 4-1

1301 gtTGGCCTG. ACCCGcTTGG A.TCAgtGAC CATTTGtTGG CAGA.CAGGG
1351 GagAgCAGcT TCCAGCcTGG gTCAGAAGGG GTGGGcGAGC CCtTcGGCCC
1401 cTcAcCCT.c cAGGcTGcTG tG.AGAGTGT CAAGTGtGTA AGGG.CCCAA
1451 A.cTcAGG.T TCAGTGCAGA ACCAgGT.CA GCAGGTATGC CCGCCCG.TA
1501 GGTTAA...GG GGGCCcTcT. AAACCCCTTG cCT.GGCCT. CAcCT.GGCC
1551 AGCTCA.CCC cTTTTGGGTG TAGGGGAAAA GAATGCCTGA CCCTGGGAAG
1601 GCTwCCCTGG TAgAATACAC CACACTTTTC AGGTTGTTGC AACACAGGTC
1651 CTGAGTTGAC CTCTGGTTCA GCCAAGGACC AAAGAAGGTG TGTAAGTGAA
1701 GTGGTTCTCA gT.CCCCAgA CATgTgCCCC TTTGCTGCTG GCTACCACTC
1751 TTCCCCAgAg CAGCAGGcCC CgAgCCCCTT CAGGcCCAgC AcTGcCCCAG
1801 AcTCgCTGGC aCTCAGTTCC CTCATCTGTA AAGGTGAAGG GTGATGCAGG

1851 ATATGCCTGA CAGGAACAGT CTGTGGAtGG AcATGATCAg TGcT.AAGG.
1901 AAAGCAGcAG AGaGAGACGy TCcGGCGCCC CAg.CCCCAc T.ATCAGTgT
1951 .CCAgCGTGC T.GGTT.CCC CAg.AGCACA GcT.CAg.CA TcA.CACTGA
2001 CACT.CAcCC T.GCCcTGCC CCT.GGCCA. GAgGGTACTG CCG.ACGGCA
2051 CTTTGCAc.T CTGATG.ACC TCAAAGCACT TTCATGgcT. GcCCTct..G
2101 GCAGGG.CAG GG.CAGGG.C AgTGAcA.CT GTAgG.AGCA TA.gCAA.GC
2151 CAgGAGATGG GGTG.AAGGG A.CACAGTCT TGAGCTGTCC A.CATGCATG
2201 TGAcT.CCTC AAAcCTcTT. .CCAG.ATTT CTCTAAGAAT AGCA.CCCCC
2251 TT.CCCCATT GCCCCAGCTT AgCCTCTTCT CCCAGGGGAG CTA.CTCAgG
2301 ACTCACGTAg CATTAAATCA GCTGTG.AAT CGTCAGGGGG TGTCTGCTAg
2351 CCTCAACCTC CTGGGGCaGG GGACgCCGAg ACTCCGTGGG AgAAgCTCAT
2401 TCcCaCATCT TGCCAAgACA gCCTTT.GTC CAgCTGTCCA CATTGAgTCA
2451 gACTGCTCCC GGGGAgAgAg cCCCGGcCCC CAgCACATAA AGAACTGCAG
2501 CCTTGGTACT GCAGAGTCTG GGTTGTAGAG AACTCTTTGT AAGCAATAAA
2551 GTTTGGGGTG ATGACAAATG TTAAAAAAAG GCCTTCGTGG CCTCGAATCA
2601 AGCTTATCGA TACCGTCGAC CTCGAGGGGG G

FIG. 4-2

```
Length: 1253   July 10, 1996   clone15

1 CATTGGAGTC ACGCGGTGGC GGCGCTCTAG AATAGTGGAT CCCCGGGCTg
  51 CA.GGAATTC GATTCGAGcC CACGAAGGCC CCTTCTTCTG TGGTCGCGGC
 101 ACGTTTACaG CCGCAAGCAc CCAGCGGCAg CTGAAGGAGG CTTTTGAgAG
 151 GCTCCTgCCC CAGGTGGAGG CGGCCCGCAA GGCCATCCgC GCCGCTCAGG
 201 TGGAGCGCTA TGTGCCCGAA CACGAGCGAT GCTGCTGGTG CCTGTGCTGC
 251 GGCTGTGAGG TGCGGGAACA CCTGAGCCAT GGAAACCTGA CGGTGCTGTA
 301 CGGGGGgCTG CTGGAGCATC TGGCCAGCCC AGAGCACAAG AAAGCAACCA
 351 ACAAATTCTG GTGGGAGAAC AAAGCTGAGG TCCAGATGAA AGAGAAGTTT
 401 CTGGTCACTC CCCAGGATTA TGCGCGATTC AAGAAATCCA TGGTGAAAGG
 451 TTTGGATTCC TATGAAGAAA AGGAGGATAA AGTGAtCAAG GAGaTGgCAG
 501 CTCAGATCCG TGaGGTGGAg CAGAgCCGAC AGGAGgTGGt TCGGtCTGTc
 551 TTAGAgCcTC AGGCAGTGCC AGAcCCAGAA GAGGGcTCTT CAGCAcCTAG
 601 AAGCTGGAAA GGGATGAACA GCCAAGTAGc TTCCAGCTTA CAGcAGcCCT
 651 CAAATTTGGA CCTGCCACCA GCTCCAGAGC TTGAcTGGAT GGAGACAGGA
 701 CCATCTCTGA CATTCATTGG CCATCAGGAT ATACCAGGAG TTGGTAACAT
 751 CCACTCAGGT GCCACACCTC CCTGGATGAT CCAAGATGAA GAATACATTG
 801 CTGGGAACCA AGAAATAGGA CCATCCTATG AAGAATTTCT TAAAGAAAAG
 851 GAAAAACAGA AGTTGAAAAA ACTcCCCCCA GACCGAGTTG GGGCCAACTT
 901 TGATCACAGC TCCAGGACCA GTGCAGGCTG GCTGCCCTCT TTTgGGcCGC
 951 GTCTGGAATA ATGGACGCCG CTGGCAGTCC AGACATCAAC TcCAAAACTG
1001 AAGCTGCAGC AATGAAGAAG CAGTCACATA CAGAAAAAAG CTAATCATGC
1051 TCTCTACCAA CTACCATGAG GCTAAAAGCC AAAGTCAACC AAACCCCTAT
1101 TATACCTTCC ACCCAAATTC TTTATCATTG TCTTTCTTAG GAAACAGACA
1151 TACTCATTCA TTTGATTTAA TAAAGTTTTA TTTTTCGGCC TTCGTGGCCT
1201 CGAATCAAGC TTATCGATAC CGtCGACCTC GAGGGGGGGC CGTACCCACT
1251 TTT
```

FIG. 5A

```
TRANSLATE of: 15cc check: 9389 from: 2 to: 1253
generated symbols 1 to: 417.

15cc.pep  Length: 417  August 23, 1996 14:32  Type: P  Check: 7921  ..

1  IGVTRWRRSR  IVDPRAAXNS  IRAHEGPFFC  GRGTFTAAST  QRQLKEAFER
   51  LLPQVEAARK  AIRAAQVERY  VPEHERCCWC  LCCGCEVREH  LSHGNLTVLY
  101  GGLLEHLASP  EHKKATNKFW  WENKAEVQMK  EKFLVTPQDY  ARFKKSMVKG
  151  LDSYEEKEDK  VIKEMAAQIR  EVEQSRQEVV  RSVLEPQAVP  DPEEGSSAPR
  201  SWKGMNSQVA  SSLQQPSNLD  LPPAPELDWM  ETGPSLTFIG  HQDIPGVGNI
  251  HSGATPPWMI  QDEEYIAGNQ  EIGPSYEEFL  KEKEKQKLKK  LPPDRVGANF
  301  DHSSRTSAGW  LPSFGPRLE*  WTPLAVQTST  PKLKLQQ*RS  SHIQKKANHA
  351  LYQLP*G*KP  KSTKPLLYLP  PKFFIIVFLR  KQTYSFI*FN  KVLFFGLRGL
  401  ESSLSIPSTS  RGGRTHF
```

FIG. 5B

```
1    AGC GGG ACT GTG CCG TGT GGA ACG TGT TGA AGG TGG ACT CTG TTA CCA TTG
                                         31
                                          *
61   AGG ATG TTT GGA GGA TGA GTA TGT GTG GCA GAG GCA CAC ATA AAC AGG CAG AGA CCC TTT
                             *                   91
121  GCC CCT GCC CTT CTC CCC CAA CCC AAG GCT GAC CTG TGT TCT CCC AGG TCT GGG ATT CTA
                                                 151
181  AGT GAC CTG CTC TGT GTT TGG TCT CTC TCA GGA TGA GCA CAA GCC TGG GAG ATG GCA GTG
                                             211  *                      M   A   V
241  ATG GAA ATG GCC TGC CCA GGT GCC CCT GGC TCA GCA GTG CAG AAG GAA CTC CCC
     M   E   M   A   C   P   G   A   P   G   S   A   V   Q   K   E   L   P
                                                 271
301  AAG CCA AAG GAG AAG ACG CCG CCA CTG GGG AAA CAG AGC TCC GTC TAC AAG CTT GAG
     K   P   K   E   K   T   P   P   L   G   K   Q   S   S   V   Y   K   L   E
                                                     331
361  GCC GTG GAG AGC AGC AGC CCT GTG TTC TGC GGA AAG TGG GAG ATC CTG AAT GAC GTG ATT ACC
     A   V   E   S   S   S   P   V   F   C   G   K   W   E   I   L   N   D   V   I   T
                                                         391
421  AAG GGC ACA GCC AAG GAA TCC GAG GCT GCA GGG CCA GCA GGG CCA CCC ACC TTT TCA GAA CGC ATT TTC ATC GCC CAG
     K   G   T   A   K   E   S   E   A   A   G   P   A   G   P   P   T   F   S   E   R   I   F   I   A   Q
                                                             451
481  GCT GAG TGT GAG AAT AGC CAA GAG TTC AGC CCC ACC CCC AAC AAT GTG GCC CAT
     A   E   C   E   N   S   Q   E   F   S   P   T   P   N   N   V   A   H
                                                     511
541  GGG TCC AAA CAG TAC AGC CAG TCC GAG AGT CTT GAT CAG ATC
     G   S   K   Q   Y   S   Q   S   E   S   L   D   Q   I
                                                 571
```

FIG. 6-1

```
601
GCT ACA GAG AAA GGC AAA ATG GCC CGT TGT TGT AAG GGA AAG CGT AGC AAA GCC CGG
 A   T   E   K   G   K   M   A   R   C   C   K   G   K   R   S   K   A   R
661
AAG AAA CGG AAG AAG AAG AGC CGT TCA AAG TCC CTG GCT CAT GCA CCA GGA GTG GCC TTG GCC AAA
 K   K   R   K   K   K   S   R   S   K   S   L   A   H   A   P   G   V   A   L   A   K
721
CCC CTC CCC AGG ACC CCT GAG AGC CAG GAG TGC ACC ATC CCA GTG CAG GAG GAT GAG
 P   L   P   R   T   P   E   S   Q   E   C   T   I   P   V   Q   E   D   E
781
CCA CTC GGC GCC CCA TAT GTT AGA AAC ACC TGC TTC ACC AAG CCT CTG AAG GAA CCA
 P   L   G   A   P   Y   V   R   N   T   C   F   T   K   P   L   K   E   P
841
GGC CTT GGG CAA CTC TGT TTT AAG CAG CTT CCG GAG GGC CTA CGG CCG GCT CTG CCT CGA
 G   L   G   Q   L   C   F   K   Q   L   P   E   G   L   R   P   A   L   P   R
901
TCA GAA CTC CAC AAA CTG ATC AGC CCC TTG CAA TGT CTG AAC CAC GTG TGG AAA CTG CAC
 S   E   L   H   K   L   I   S   P   L   Q   C   L   N   H   V   W   K   L   H
961
CAC CCC CAG GAC GGA GGC CCA CCT CCC CTG ACG CCC AAA CCT CAC TTC CCC TAT AGC AGA TCC TTC
 H   P   Q   D   G   G   P   P   P   L   T   P   K   P   H   F   P   Y   S   R   S   F
1021
CCT CAT CCC TTC CCA TTC CAC CCT CTC CAG CCC TGG CCC AAA CCT CCA CAC CCT CTG GAG AGC AAA
 P   H   P   F   P   F   H   P   L   Q   P   W   P   K   P   P   H   P   L   E   S   K
1081
CTG GGC AAA CTG GCC TGT GTA GAC AGT CCA AAG CCC CTG TTG CCT GGC CCA GAG TAC CAT GCT CTG
 L   G   K   L   A   C   V   D   S   P   K   P   L   L   P   G   P   E   Y   H   A   L
1141
CTG GCC TGT GGT GCC CAT GAG AAG TTT TCT GTG GAG TAC CTA GTG CAT CTG CAA GGC
 L   A   C   G   A   H   E   K   F   S   V   E   Y   L   V   H   L   Q   G
1201
TCT CGT GGT GCC CAT GAG AAG TTT TCT GTG GAG GAA TAC CTA GTG CAT GCT CTG CAA GGC
 S   R   G   A   H   E   K   F   S   V   E   E   Y   L   V   H   A   L   Q   G
1261
AGC GTG AGC TCA AGC CAG GCC CAC AGC CTG GCC AAG ACC TGG GCA GCA CGG
 S   V   S   S   S   Q   A   H   S   L   A   K   T   W   A   A   R
```

FIG. 6-2

```
1321
     GGC TCC AGA TCC CGG GAG CCC AGC CCC AAA ACT GAG GAC AAC GAG GGT GTC CTG CTC ACT
      G   S   R   S   R   E   P   S   P   K   T   E   D   N   E   G   V   L   L   T
1381                                              1351
     GAG AAA CTC AAG CCA GTG GAT TAT GAG TAC CGA GAA GAA GTC CAC TGG GCC ACG CAC CAG
      E   K   L   K   P   V   D   Y   E   Y   R   E   E   V   H   W   A   T   H   Q
1441                                              1411
     CTC CGC CTG GGC AGA GGC TCC TTC GGA GTG CAC GAG ATG GAG GAC AAG CAG ACT GGC
      L   R   L   G   R   G   S   F   G   E   V   H   R   M   E   D   K   Q   T   G
1501                                              1471
     TTC CAG TGC GCT GTC AAA AAG GTG CGC CTG GAA GTA TTT CGG GCA GAG GAG CTG ATG GCA
      F   Q   C   A   V   K   K   V   R   L   E   V   F   R   A   E   E   L   M   A
1561                                              1531
     TGT GCA GGA TTG ACC TCA CCC AGA ATT GTC CCT TTG TAT GGA GCT GTG AGA GAA GGG CCT
      C   A   G   L   T   S   P   R   I   V   P   L   Y   G   A   V   R   E   G   P
1621                                              1591
     TGG GTC AAC ATC TTC ATG GAG CTG CTG GAA GGT GGC TCC CTG GGC CAG GTC AAG GAG
      W   V   N   I   F   M   E   L   L   E   G   G   S   L   G   Q   L   V   K   E
1681                                              1651
     CAG GGC TGT CTC CCA GAG GAC CGG GCT CTG TAC TAC CTG TAC CAG GCC CTG GAG GGT CTG
      Q   G   C   L   P   E   D   R   A   L   Y   Y   L   Y   Q   A   L   E   G   L
1741                                              1711
     GAA TAC CTC CAC TCA CGA AGG ATT CTG CAT GGG GAC GTC AAA GCT GCT GTG CTC CTG
      E   Y   L   H   S   R   R   I   L   H   G   D   V   K   A   A   N   V   L   L
1801                                              1771
     TCC AGC GAT GGG AGC CAC GCC CTC CTC TGT GAC TTT GGC CAT GCT CCT CTT CAA CCT
      S   S   D   G   S   H   A   L   L   C   D   F   G   H   A   V   C   L   Q   P
1861                                              1831
     GAT GGC CTG GGA AAG TCC TTG CTC ACA GGG GAC TAC ATC CCT GGC ACC GAG ACC CAC ATG
      D   G   L   G   K   S   L   L   T   G   D   Y   I   P   G   T   E   T   H   M
1921                                              1891
     GCT CCG GAG GTG GTG CTG GGC AGG AGC TGC GAT GCC AAG GTG GAT GTC TGG AGC TGC
      A   P   E   V   V   L   G   R   S   C   D   A   K   V   D   V   W   S   C
                                                  1951
```

FIG. 6-3

```
1981
TGT ATG ATG CTG CAC ATG CTC AAC GGC TGC CAC CCC TGG ACT CAG TTC CGA GGG CCG
 C   M   M   L   H   M   L   N   G   C   H   P   W   T   Q   F   R   G   P
                                         2011
2041
CTC TGC CTC AAG ATT GCC AGC GAG CCT CCG AGG ATC GAG GAG ATC CCA TCC TGC GCC
 L   C   L   K   I   A   S   E   P   P   R   I   E   E   I   P   S   C   A
                                         2071
2101
CCT CTC ACA GCC CAG GCC ATC CAA GAG GGG CTG AGG AAA GAG CCC ATC CAC CGC GTG TCT
 P   L   T   A   Q   A   I   Q   E   G   L   R   K   E   P   I   H   R   V   S
                                         2131
2161
GCA GCG GAG CTG GGA GGG AAG GTG AAC CGG CTG AGG GTG CAA GGT CTG AAG AGC
 A   A   E   L   G   G   K   V   N   R   L   R   V   Q   G   L   K   S
                                         2191
2221
CCT TGG AGG GGA GAA TAT AAA GAA CCA AGA CAT CCA CCG CCA CAA AAT TAC CAC
 P   W   R   G   E   Y   K   E   P   R   H   P   P   P   Q   N   Y   H
                                         2251
2281
CAG ACC CTC CAT GCC CAG CCG AGA GAG CTT TCG CCA AGG GCC CCC CGG CCA GCT
 Q   T   L   H   A   Q   P   R   E   L   S   P   R   A   P   R   P   A
                                         2311
2341
GAG GAG ACA ACA GGC AGA GCC CCT AAG CTC CAG CCT CCT CTC CCA GAG CCC GAG
 E   E   T   T   G   R   A   P   K   L   Q   P   P   L   P   E   P   E
                                         2371
2401
CCA AAC AAG TCT CCT TGG ACT TTG AGC AAG GAG GAG TCT GGG ATG TGG GAA CCC TTA
 P   N   K   S   P   W   T   L   S   K   E   E   S   G   M   W   E   P   L
                                         2431
2461
CCT CTG TCC CTG CAG CAG CCA CCT CCA GCC CCT AGA AAC CCC TCA AGC CGG AAA GCA
 P   L   S   L   Q   Q   P   P   P   A   P   R   N   P   S   P   E   R   K   A
                                         2491
2521
ACC GTC CCG GAG CAG GAA CTG CAG GAG ATA GAA ATT CTC TTC CTC AAC AGC CTG TCC
 T   V   P   E   Q   E   L   Q   E   I   E   I   L   F   L   N   S   L   S
                                         2551
2581
CAG CCA TTT TCT GAG AGT GAG AAG AAC CCA TCA AAG GCC TCT CAA AGC ATC GAC ACC
 Q   P   F   S   E   S   E   K   N   P   S   K   A   S   Q   S   I   D   T
                                         2611
2641
TCC CTG TCG GAT GAC CAC CAC TCA AAG GCC GAG GCT CGA AGC TCC CGG GAC
 S   L   S   D   D   H   H   S   K   A   E   A   R   S   S   R   D
                                         2671
2701
CTG AGC TCA GGC GTA CAC TCC TGG AGC AGC CAG GCC GAG GCT CGA AGC TCC AGC AAC
 L   S   S   G   V   H   S   W   S   S   Q   A   E   A   R   S   S   W   N
                                         2731
2761
ATG GTG CTG GCC CGG GGG CGG CCC ACC GAC ACC CCA AGC TAT TTC AAT GGT GTG AAA GTC
 M   V   L   A   R   G   R   P   T   D   T   P   S   Y   F   N   G   V   K   V
                                         2791
```

FIG. 6-4

```
2821
CAA ATA CAG TCT CTT AAT GGT GAA CAC CTG CAC ATC CGG GAG TTC CAC CGG GTC AAA GTG
 Q   I   Q   S   L   N   G   E   H   L   H   I   R   E   F   H   R   V   K   V
2881                                                         2911
GGA GAC ATC GCC ACT GGC ATC AGC CAG ATC CCA GCT GCA GCC TTC AGC TTG GTC ACC
 G   D   I   A   T   G   I   S   Q   I   P   A   A   A   F   S   L   V   T
2941                                             2971
AAA GAC GGG CAG CCT GTT CGC TAC GAC ATG GAG GTG CCA GAC TCG GGC ATC GAC CTG CAG
 K   D   G   Q   P   V   R   Y   D   M   E   V   P   D   S   G   I   D   L   Q
3001                                 3031
TGC ACA CTG GCC CCT GAT GGC AGC TTC GCC TGG AGC GTC AAG CAT TGC CGG CAG CTG
 C   T   L   A   P   D   G   S   F   A   W   S   V   K   H   C   R   Q   L
3061
GAG AAC AGG CCC TAA CCC TGC CCT CCA CCG CCG GCT CCA CAC TGC CGG AAA GCA GCC TTC
 E   N   R   P   *
3121
CTG CTC GGT GCA CGA TGC CCT GAA AAC AGC TCA GCC GTT CCC AGG GGA TTG CCA
3181
GCC CCC CGG CTC ACA GTG GGA ACC ATG GCC TCG CAG CAG CAA GGT GGG GGC AAG CAG AAT
3241
GCC TCC CAG GAT TTC ACA CCT GAG CCC TGC CCC ACC CTG CTG AAA AAA CAT CCG CCA CGT
3301
GAA GAG ACA GAA GGA GGA TGG CAG GAG TTA CCT GGG GAA ACA AAA CAG GGA TCT TTT TCT
3361
GCC CCT GCT CCA GTC GAG GCT TGG ATC AGT GAC CAT TTG TTG GCA GAC
3421
AGG GGA GAG CAG CTT CCA GCC TGG GTC AGA AGG GGT GGG CGA GCC CTT CGG CCC CTC ACC
```

FIG. 6-5

```
3481
CTC CAG GCT GCT GTG AGA GTG TCA AGT GTG TCA AGT GCA GAA
                                                  3511
                                        CCC AAA CTC AGG TTC AGT GCA GAA
3541
CCA GGT CAG CAG GTA TGC CCG CCC GTA GGT TAA GGG GGC CCT CTA AAC CCC TTG CCT GGC
                                                  3571
3601
CTC ACC TGG CCA GCT CAC CCC TTT TGG GTG TAG GGG AAA AGA ATG CCT GAC CCT GGG AAG
                                                  3631
3661
GCT CCC TGG TAG AAT ACA CAC TTT TCA GGT TGT TGC AAC ACA GGT CTC GAG TTG ACC
                                                  3691
3721
TCT GGT TCA GCC AAG GAC CAA AGA AGG TGT GTA AGT GAA GTG GTT CTC AGT CCC CAG ACA
                                                  3751
3781
TGT GCC CCT TTG CTG GCT ACC ACT CTT CCC CAG AGC AGC AGG CCC CGA GCC CCT TCA
                                                  3811
3841
GGC CCA GCA CTG CCC CAG ACT CGC TGG CAC TCA GTT CCC TCA TCT GTA AAG GTG AAG GGT
                                                  3871
3901
GAT GCA GGA TAT GCC TGA CAG GAA CAG TCT GTG GAT GGA CAT GAT CAG TGC TAA GGA AAG
                                                  3931
3961
CAG CAG AGA GAG ACG TCC GGC GCC CCA CTA TCA GTG TCC AGC GTG CTG GTT CCC
                                                  3991
4021
CAG AGC ACA GCT CAG CAT CAC ACT GAC ACT CAC CCT GCC CTG CCC CTG GCC AGA GGG TAC
                                                  4051
4081
TGC CGA CGG CAC TTT GCA CTC TGA TGA CCT CAA AGC ACT TTC ATG GCT GCC CTC TGG CAG
                                                  4111
```

FIG. 6-6

```
4141
GGC AGG GCA GGG CAG TGA CAC TGT AGG AGC ATA GCA AGC CAG GAG ATG GGG TGA AGG GAC
                                        4171
4201
ACA GTC TTG AGC TGT CCA CAT GCA TGT GAC TCC TCA AAC CTC TTC CAG ATT TCT CTA AGA
                                                4231
4261
ATA GCA CCC CCT TCC CCA TTG CCC CAG CTT CCC TTC TCC CAG GGG AGC TAC TCA GGA
                                                        4291
4321
CTC ACG TAG CAT TAA ATC AGC TGT GAA TCG TCA GGG GGT GTC TGC TAG CCT CAA CCT CCT
                                                                4351
4381
GGG GCA GGG GAC GCC GAG ACT CCG TGG GAG ACT CTC ATT CCC ACA TCT TGC CAA GAC AGC
                                                                        4411
4441
CTT TGT CCA GCT GTC CAC ATT GAG TCA GAC TGC TCC CGG GGA GAG AGC CCC GGC CCC CAG
                                                                                4471
4501
CAC ATA AAG AAC TGC AGC CTT GGT ACT GCA GAG TCT GGG TTG TAG AGA ACT CTT TGT AAG
                                                                                        4531
4561
CAA TAA AGT TTG GGG TGA TGA CAA ATG TTA AAA AAA
                                        4596
```

FIG. 6-7

```
s3  1 ------------------------- 0
s4  1 ------------------------- 0
s9  1 ------------------------- 0
s7  1 ------------------------- 0
s2  1 ------------------------- 0
s6  1 MPFLRKIAGTAHTHSRSDSNSSVKFGHQPTSSV 33
s8  1 ------------------------- 0
s1  1 ------------------------- 0
s5  1 ------------------------- 0 s3  1 ------------------------- 0
s4  1 ------------------------- 0
s9  1 ------------------------- 0
s7  1 ------------------------- 0
s2  1 ------------------------- 0
s6 34 ASTKSSSKSPRATSRKSIYDDIRSQFPNLTPNS 66
s8  1 ------------------------- 0
s1  1 ------------------------- 0
s5  1 ------------------------- 0
```

FIG. 7-1

```
s3   1 ---------------------------------  0
s4   1 ---------------------------------  0
s9   1 ---------------------------------  0
s7   1 ---------------------------------  0
s2   1 ---------------------------------  0
s6   1 ---------------------------------  0
s8  67 TSSQFYESTPVIEQSFNWTTDDHISAGTLENPT 99
s1   1 ---------------------------------  0
s5   1 ---------------------------------  0 s3   1 ------------------------------    0
s4   1 ------------------------------    0
s9   1 ------------------------------    0
s7   1 ------------------------------    0
s2   1 ------------------------------    0
s6   1 ------------------------------    0
s8   1 -----------------------RKSSGGNSVNSLSF 132
s1 100 SETNSSYKNDNGPSSLSDSRKSSGGNSVNSLSF   0
s5   1 ---MMMDILNTQQKAAEGGRVLAPHTIS       26
```

FIG. 7-2

|  |  |  |  |
|---|---|---|---|
| s3 | 1 | | 0 |
| s4 | 1 | | 0 |
| s9 | 1 | | 0 |
| s7 | 1 | | 0 |
| s2 | 1 | | 0 |
| s6 | 1 | | 0 |
| s8 | 133 | DKLILSWDPTDPDEWTMHRVTSWFKFHDFPESW | 165 |
| s1 | 1 | | 0 |
| s5 | 27 | SKLVKRLSSHSSHKLSRSDLKALGGSETISDGP | 59 |
| s3 | 1 | | 0 |
| s4 | 1 | | 0 |
| s9 | 1 | | 0 |
| s7 | 1 | | 0 |
| s2 | 1 | | 0 |
| s6 | 1 | | 0 |
| s8 | 166 | ILFFKKHQLFGHRFIKLLAYDNFAVYEKYLPQT | 198 |
| s1 | 1 | | 0 |
| s5 | 60 | SQLTFKDRYVFNESLYLKKLKKTALDDYYTRGI | 92 |

FIG. 7-3

```
s3  1 ------------------------------- 0
s4  1 ------------------------------- 0
s9  1 ------------------------------- 0
s7  1 ------------------------------- 0
s2  1 ------------------------------- 0
s6  1 ------------------------------- 0
s8  199 KTASYTRFQQLLKKTMTKNVTNSHIRQKSASKL 231
s1  1 ------------------------------- 0
s5  93 KLTNRYEEDDGDEIIRLSNGDRIDEDLHSGVK 125 s3  1 -------------------------------- 0
s4  1 -------------------------------- 0
s9  1 -------------------------------- 0
s7  1 -------------------------------- 0
s2  1 -------------------------------- 0
s6  1 -------------------------------- 0
s8  232 KSSRSSSIKSKLKNSKSQEDISNSRSTSESA 264
s1  1 -------------------------------- 0
s5  126 FFSTTPYCRKMRSDSDELAWNEIATERFKWQSM 158
```

FIG. 7-4

| | | |
|---|---|---|
| s3 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s4 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s9 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s7 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s2 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s6 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s8 | 265 | L S P T K S G P S K T D E K N F L H S T H Q K T K S A S S L Y 297 |
| s1 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s5 | 159 | L A R V L K G D I V K G E K T R I A N Q V K K P G L N K E L S D E 191 |

| | | |
|---|---|---|
| s3 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s4 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s9 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s7 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s2 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s6 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s8 | 298 | R R S F I S L R G S S S S N A S S A K S P S N I K L S I P A R P H 330 |
| s1 | 1 | ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ ‐ 0 |
| s5 | 192 | I W L E L K A W L N G R T M Q E M E Q S L T Y L R D S S D S V F E 224 |

```
s3  1 --------------------------------- 0
s4  1 --------------------------------- 0
s9  1 --------------------------------- 0
s7  1 --------------------------------- 0
s2  1 --------------------------------- 0
s6  1 --------------------------------- 0
s8  331 SHIESNSTLTKSASPPASPPASPSYPSIFRRHHKSS 363
s1  1 --------------------------------- 0
s5  225 EIMKFQIPQGKILSLDALEAILQDLMNRYHSV 257 s3  1 --------------------------------- 0
s4  1 --------------------------------- 0
s9  1 --------------------------------- 0
s7  1 --------------------------------- 0
s2  1 --------------------------------- 0
s6  1 --------------------------------- 0
s8  364 SESSLIKNSLFGSGIGEEAPTKPNPQGHSLSSEN 396
s1  1 --------------------------------- 0
s5  258 SYWPNLKKMYKDKPITNTAEFTARIDVMNSWLN 290
```

| | | | |
|---|---|---|---|
| s3 | 1 | | 0 |
| s4 | 1 | | 0 |
| s9 | 1 | | 0 |
| s7 | 1 | | 0 |
| s2 | 1 | | 0 |
| s6 | 1 | | 0 |
| s8 | 397 | L A K G K S K H Y E T N V S S P L K Q S S L P T S D D K G N L W N | 429 |
| s1 | 1 | | 0 |
| s5 | 291 | F K T N L T L R R Q E L D D W I N R F S P I S S S D N C Q E D F D | 323 |
| s3 | 1 | | 0 |
| s4 | 1 | | 0 |
| s9 | 1 | | 0 |
| s7 | 1 | | 0 |
| s2 | 1 | | 0 |
| s6 | 1 | | 0 |
| s8 | 430 | K F K R K S Q I G V P S P N T V A Y V T S Q E T P S L K S N S S T | 462 |
| s1 | 1 | | 0 |
| s5 | 324 | G V P Q W N C K M K I L A E Q L M K E K N I E S I F Q K | 351 |

FIG. 7-7

```
s3                                                          - 0
s4                                                          - 0
s9                                                          - 0
s7                                                          - 0
s2                                                          - 0
s6                                                          - 0
s8  463 ATLTVQTADVNIPSPSSSPPPPIPKTANRSLEVI                  - 495
s1                                                          - 0
s5  352     KIFYPLSPWMFKLKLHFIVYRET                         - 374 s3                                                          - 0
s4                                                          - 0
s9                                                          - 0
s7                                                          - 0
s2                                                          - 0
s6                                                          - 0
s8  496 STEDTPKISSTTASFKETYPDCINPDKTVPVPV                   - 528
s1                                                          - 0
s5  375 LTKMNIKYPYERLRSLLAFPVLIKEVILTRLS                    - 407
```

FIG. 7-8

| | | | |
|---|---|---|---|
| s3 | 1 | - - - - - - - - - - - - - - - - - - - - - - - - - - - - - - - - - - - - - - | 0 |
| s4 | 1 | - - - - - - - - - - - - - - - - - - - - - - - - - - - - - - - - - - - - - - | 0 |
| s9 | 1 | - - - - - - - - - - - - - - - - - - - - - - - - - - - - - - - - - - - - - - | 0 |
| s7 | 1 | - - - - - - - - - - - - - - - - - - - - - - - - - - - - - - - - - - - - - - | 0 |
| s2 | 1 | - - - - - - - - - - - - - - - - - - - - - - - - - - - - - M E Y Y | 4 |
| s6 | 1 | - - - - - - - - - - - - - - - - - - - M E Q T A E G T D L L I | 14 |
| s8 | 529 | N N Q K Y S V K N F L L D Q K F Y P L K K T G L N D S E N K Y I L | 561 |
| s1 | 1 | - - - - - - - - - - - - - - - - - - - - - - - - - - - - - - - - - - - - - - | 0 |
| s5 | 408 | Y A R K L K N P T M M M I D Q M I D D F N A F I R L S V Q L K Y T | 440 |

| | | | |
|---|---|---|---|
| s3 | 1 | - - - - - - - - - - - - - - - - - - - - - - - - - - - - - - - - - - - - - - | 0 |
| s4 | 1 | - - - - - - - - - - - - - - - - - - - - - - - - - - - - - - - - - - - - - - | 0 |
| s9 | 1 | - - - - - - - - - - - - - - - - - - - - - - - - - - - - - - - - - - - - - - | 0 |
| s7 | 1 | - - - - - - - - - - - - - - - - - - - - - - - - - - - - - - - - - - - - - - | 0 |
| s2 | 5 | T S K - - - E - - - - - V A E W L K S I G - L E K Y I E Q F S | 26 |
| s6 | 15 | G D - - E K T N D L P F V Q L F E E I G - C T Q Y L D S F I Q | 43 |
| s8 | 562 | V T K - - D - - - N V S F V P L N L K S V A K L S S F K E S A L | 588 |
| s1 | 1 | - - - - - - - - - - - - - - - - - - - - - - - - - - - - - - - - - - - - - - | 0 |
| s5 | 441 | L T K Y C S N L P F D V D F D P T F E N T V I E A I R Y L F F L L | 473 |

```
s3          1                                                                                        -    0
s4          1                                                                                        -    0
s9          1                                                                                        -    0
s7          1                                                                                        -    0
s2         67  - - - - - - - - - - - - - - - - - VNRLKNLMEKVSSLSTATLSMNSELIPEKHCVI - -             73
s6         90  - - - - - - - - - - - - - - - - - PLTSENNVPLKSVKSKSSMRSGTSSLIASTDDV - -            122
s8        649  - - - - - - - - - - - - - - - - - - - - - - - - - - - - - - - - - - -            681
s1          1  - - - - - - - - - - - - - - - - - TFANASEAEKWLSSIFENLGAMKRKLNRFSNIL - -              0
s5        540                                                                                       572 s3          1                                                                                        -    0
s4          1                                                                                        -    0
s9          1                                                                                        -    0
s7          1                                                                                        -    0
s2         74  - - - - - - - - - - - - - - - - - RFIACNGQTRAVQSRGDY - - - - - QKTLAIALKK           101
s6        123  - - - - - - - - - - - - - - - - - FILNDGSAKKVNVNGCFNADSIKKRLIRRLPHE                 155
s8        682  - - - - - - - - - - - - - - - - - SIVTSSSDITSFDEHASGSGRRYPQTPSYYDR                  714
s1          1  - - - - - - - - - - - - - - - - - - - - - - - - - - - - - MVTAVPAVFSKL              12
s5        573  - - - - - - - - - - - - - - - - - VKAFQNSAVYQINHNAQLVKKL - - KDAHYFLVY             603
```

```
s3    -  : : : :                                                              -   0
s4    -  : : : :                                                              -   0
s9   14  SAVGQKELPKPKEKTPPLGKKQSSVYKLEAVE                                        46
s7    -  : : : :                                                              -   0
s2  148  KEKPCPSFEDLRRS-WEIELAQPAALSSQSSLS                                      179
s6  213  DQT-PSDKAISTS-KKLYL--RTLSALSQVGP                                       240
s8  781  KDEGTEIDFNHRRE-SPYTKPELAPKREAPKPP                                      812
s1   79  REKTGKGLSATRLSASSEDISDRLAGVSVGLPS                                      111
s5  670  KGEDSKGIPYYRVVANSSSDLDRHAHQSKKKNF                                      702 s3    -  : : : :                                                              -   0
s4    -  : : : :                                                              -   0
s9   47  KSPVFCGKWEILNDVITKGTAKEGSEAGPAAIS                                       79
s7    -  : : : :                                                              -   0
s2  180  PKLSS--VLPTSTQKRSVRSNNAKPFESY---                                       206
s6  241  SSSN--LLA---QNKGISHNNAEGKLRIDNTEK                                      268
s8  813  ANTSPQRTLSTSKQNKPIRLVRASTKISRSKRS                                      845
s1  112  STTTEQPKPAVQTKGRPHSQCLNSSPLSHAQLM                                      144
s5  703  STDPFDQHLD-EKNNEVFELEVALSSLGALVVL                                      734
```

```
s3    1                                                                            0
s4    1                                                                            0
s9  146  RKKSSKSLAHAGVALAKPLPRTPEQESCTIPV                                         178
s7    1                                                                            0
s2  242  LSIRTSQGHNLG---NFGQEILPRSS------RRA                                      267
s6  313  RLSIAQRRPLSAESNNIGDILLKHSN-----AV                                        340
s8  905  PSLKMKQKVNRSNSTVSTSNSIFYSPLLKRG                                          937
s1  204  PVFTQSRPPPSSNIHRPKPSRPVPGSTSKLGDA                                        236
s5  801  EKRCSLNSIESSLQKINKAYYKLTYTVLNNYKG                                        833 s3    1                                                                            0
s4    1                                                                            0
s9  179  QEDESPLGAPYVRNTPQFTKPLKEPGLGQLCFK                                        211
s7    1                                                                            0
s2  268  RPSELVCPLSSLRI----------------SVA                                        284
s6  341  DMALLQGLDQTRL------------------SSKL                                      357
s8  938  NSKRVVSTSAADIFEENDITFADAPPMFDSDD                                         970
s1  237  TKSSMTLDLGSASRCDDSFGGGNSGNAVIPSD                                         269
s5  834  ILGSFMKQCPGNELLNSIFMFGRDFGRSFLKYN                                        866
```

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| s3 | 462 | | | | P | T | L | E | Y | G | | | | | | | | | | | | | | | | | | | | 467 |
| s4 | 462 | | | | P | T | L | E | Y | G | | | | | | | | | | | | | | | | | | | | 467 |
| s9 | 786 | | | | F | S | L | E | Q | E | Q | I | L | S | C | L | S | I | D | S | L | S | D | D | S | E | K | N | P | S | K | A | S | Q | 818 |
| s7 | 491 | | | | A | N | L | H | Y | D | Q | A | T | I | K | P | T | N | N | P | I | M | S | Y | K | E | D | L | A | F | T | F | P | S | G | Q | S | 523 |
| s2 | 0 | | | | — | — | — | — | — | — | — | — | — | — | — | — | — | — | — | — | — | — | — | — | — | — | — | — | — | — | — | 659 |
| s6 | 0 | | | | — | — | — | — | — | — | — | — | — | — | — | — | — | — | — | — | — | — | — | — | — | — | — | — | — | — | — | 717 |
| s8 | 0 | | | | — | — | — | — | — | — | — | — | — | — | — | — | — | — | — | — | — | — | — | — | — | — | — | — | — | — | — | 1478 |
| s1 | 0 | | | | — | — | — | — | — | — | — | — | — | — | — | — | — | — | — | — | — | — | — | — | — | — | — | — | — | — | — | 672 |
| s5 | 0 | | | | — | — | — | — | — | — | — | — | — | — | — | — | — | — | — | — | — | — | — | — | — | — | — | — | — | — | — | 1314 |
| | | | | | | | | | | | | | | | | | | | | | | | | | | | | | | |
| s3 | 0 | | | | — | — | — | — | — | — | — | — | — | — | — | — | — | — | — | — | — | — | — | — | — | — | — | — | — | — | — | 467 |
| s4 | 0 | | | | — | — | — | — | — | — | — | — | — | — | — | — | — | — | — | — | — | — | — | — | — | — | — | — | — | — | — | 467 |
| s9 | 819 | | | | S | S | R | D | T | L | S | G | V | H | S | W | S | Q | A | E | R | S | A | M | D | L | K | L | Q | T | P | L | Y | R | P | 851 |
| s7 | 524 | | | | A | A | E | D | D | D | E | L | T | E | S | K | I | R | A | F | L | D | E | K | A | M | D | L | K | L | Q | T | P | L | Y | E | 556 |
| s2 | 0 | | | | — | — | — | — | — | — | — | — | — | — | — | — | — | — | — | — | — | — | — | — | — | — | — | — | — | — | — | 659 |
| s6 | 0 | | | | — | — | — | — | — | — | — | — | — | — | — | — | — | — | — | — | — | — | — | — | — | — | — | — | — | — | — | 717 |
| s8 | — | | | | — | — | — | — | — | — | — | — | — | — | — | — | — | — | — | — | — | — | — | — | — | — | — | — | — | — | — | 1478 |
| s1 | 0 | | | | — | — | — | — | — | — | — | — | — | — | — | — | — | — | — | — | — | — | — | — | — | — | — | — | — | — | — | 672 |
| s5 | 0 | | | | — | — | — | — | — | — | — | — | — | — | — | — | — | — | — | — | — | — | — | — | — | — | — | — | — | — | — | 1314 |

FIG. 7-26

| | | | | | | | | | | | | | | | | | | | | | | | |
|---|---|---|---|---|---|---|---|---|---|---|---|---|---|---|---|---|---|---|---|---|---|---|---|
| s3 | 0 | | | | | | | | | | | | | | | | | | | | | | 467 |
| s4 | 0 | | | | | | | | | | | | | | | | | | | | | | 467 |
| s9 | 852 | T | D | T | P | S | Y | F | N | G | V | K | V | Q | I | Q | S | L | N | G | E | H | L | H | I | R | E | F | H | R | V | K | V | G | 884 |
| s7 | 557 | G | F | Y | N | S | L | N | V | S | S | T | P | S | P | V | G | T | G | N | K | E | N | V | P | S | N | I | N | L | P | P | K | S | 589 |
| s2 | 0 | | | | | | | | | | | | | | | | | | | | | | 659 |
| s6 | 0 | | | | | | | | | | | | | | | | | | | | | | 717 |
| s8 | 0 | | | | | | | | | | | | | | | | | | | | | | 1478 |
| s1 | 0 | | | | | | | | | | | | | | | | | | | | | | 672 |
| s5 | 0 | | | | | | | | | | | | | | | | | | | | | | 1314 |
| s3 | 0 | | | | | | | | | | | | | | | | | | | | | | 467 |
| s4 | 0 | | | | | | | | | | | | | | | | | | | | | | 467 |
| s9 | 885 | D | I | A | T | G | I | S | S | Q | I | P | A | A | A | F | S | L | V | T | K | D | G | Q | P | V | R | Y | D | M | E | V | P | D | 917 |
| s7 | 590 | R | S | P | K | R | M | L | S | R | R | L | S | T | A | I | E | G | A | C | A | P | S | P | V | T | H | S | K | R | I | S | N | I | 622 |
| s2 | 0 | | | | | | | | | | | | | | | | | | | | | | 659 |
| s6 | 0 | | | | | | | | | | | | | | | | | | | | | | 717 |
| s8 | 0 | | | | | | | | | | | | | | | | | | | | | | 1478 |
| s1 | 0 | | | | | | | | | | | | | | | | | | | | | | 672 |
| s5 | 0 | | | | | | | | | | | | | | | | | | | | | | 1314 |

Alignment block 1:

| Seq | Start | Sequence | End |
|---|---|---|---|
| s3 | 0 | – | 467 |
| s4 | 0 | – | 467 |
| s9 | 918 | SGIDLQCTLAPDGSFAWSWRVKHGQLENRP | 947 |
| s7 | 623 | GGLNGEAIQEAQLPRHNEWKDLLGSQREAVNSS | 655 |
| s2 | 0 | – | 659 |
| s6 | 0 | – | 717 |
| s8 | 0 | – | 1478 |
| s1 | 0 | – | 672 |
| s5 | 0 | – | 1314 |

Alignment block 2:

| Seq | Start | Sequence | End |
|---|---|---|---|
| s3 | 0 | – | 467 |
| s4 | 0 | – | 467 |
| s9 | 0 | – | 947 |
| s7 | 656 | FSERQRRWKEELDEELQRRKKREIMRQAVNLSPPK | 688 |
| s2 | 0 | – | 659 |
| s6 | 0 | – | 717 |
| s8 | 0 | – | 1478 |
| s1 | 0 | – | 672 |
| s5 | 0 | – | 1314 |

SEQUENCE LISTING

```
<160> NUMBER OF SEQ ID NOS: 23

<210> SEQ ID NO 1
<211> LENGTH: 1906
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t

<400> SEQUENCE: 1
cattgggtca cgcggtggcg gcgctctaga atagtggatc ccccgggctg caggaattcg      60
attcgaggcc acgaaggccg gcggcgcggc gcangcaccg gcccggggan aggcnccatg     120
agcggatcnc ngaacnatga caaaagacaa tttctgctgg agcgactgct ggatgcagtg     180
aaacagtgcc agatccgctt tngagggaga aaggagattg cctcggattc cgacagcagg     240
gtcacctgtc tgtgtgccca gtttgaagcc gtcctgcagc atggcttgaa gaggagtcga     300
ggattggcac tcacagcggc agcgatcaag caggcagcgg gctttgccag caaaaccgaa     360
```

-continued

```
acagagcccg tgttctggta ctacgtgaag gaggtcctca acaagcacga gctgcagcgc    420
ttctactccc tgcgccacat cgcctcagac gtgggccggg gtcgcgcctg gctgcgctgt    480
gccctcaacg aacactccct ggagcgctac ctgcacatgc tcctggccga ccgctgcagg    540
ctgagcactt tttatgaaga ctggtctttt gtgatggatg aagaaaggtc cagtatgctt    600
cctaccatgg cagcaggtct gaactccata ctctttgcga ttaacatcga caacaaggat    660
ttgaacgggc agagtaagtt tgctcccacc gtttcagacc tcttaaagga gtcaacgcag    720
aacgtgacct ccttgctgaa ggagtccacg caaggagtga gcagcctgtt cagggagatc    780
acagcctcct ctgccgtctc catcctcatc aaacctgaac aggagaccga cccttgcctg    840
tcgtgtccag gaatgtcagt gctgatgcca aatgcaaaaa ggagcggaag aagaaaaaga    900
aagtgaccaa cataatctca tttgatgatg aggaagatga gcagaactct ggggacgtgt    960
ttaaaaagac acctggggca ggggagagct cagaggacaa ctccgaccgc tcctctgtca   1020
atatcatgtc cgccttttgaa agcccccttcg ggcctaactc caatggaatc agagcagcaa   1080
ctcatggaaa attgattccc tgtctttgaa cggggagttt gggtaccaga gcttgatgt   1140 gaaaagcatc gatgatgaag atgtggatga aaacgaagat gacgtgtatg aaactcatc   1200 aggaaggaag cacaggggcc actcggagtc gcccgagaag ccactggaag gaacacctg   1260 cctctcccag atgcacagct gggctccgct gaaggtgctg cacaatgact ccgacatcct   1320
cttccctgtc agtggcgtgg gctcctacag cccagcagat gccccctcg aagcctgga   1380 gaacgggaca ggaccagagg accacgttct cccggatcct ggacttcggt acagtgtgga   1440
agccagctct ccaggccacg gaagtcctct gagcagcctg ttacttctgc ctcagtgcca   1500
gagtccatga caattagtga actgcgccag gccactgtgg ccatgatgaa caggaaggat   1560
gagctggagg aggagaacag atcactgcga aacctgctcg acggtgagat ggagcactca   1620
gccgcgctcc ggcaagaggt ggacaccttg aaaaggaagg tggctgaaca ggaggagcgg   1680
cagggcatga aggtccaggc gctggccagc tatctttgct attttgtgag gagattctaa   1740
ccccacgtga gaaccatgtg gtggagaaat ggagggagag agaaatccaa cagttcctga   1800
tagtctcatt tgagctcctg gatccagtct ttcctgaagc tgtgtttcct ctggactttt   1860
catgtatgtg agccaataaa ttgctttcat tccttgaaaa aaaaaa                  1906
```

<210> SEQ ID NO 2
<211> LENGTH: 604
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature

```
<222> LOCATION: (37)..(37)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (334)..(334)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (354)..(355)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (569)..(570)
<223> OTHER INFORMATION: Xaa can be any naturally occurring amino acid

<400> SEQUENCE: 2

Xaa Thr Gly Pro Gly Xaa Gly Xaa Met Ser Gly Ser Xaa Asn Xaa Asp
1               5                   10                  15

Lys Arg Gln Phe Leu Leu Glu Arg Leu Leu Asp Ala Val Lys Gln Cys
            20                  25                  30

Gln Ile Arg Phe Xaa Gly Arg Lys Glu Ile Ala Ser Asp Ser Asp Ser
        35                  40                  45

Arg Val Thr Cys Leu Cys Ala Gln Phe Glu Ala Val Leu Gln His Gly
50                  55                  60

Leu Lys Arg Ser Arg Gly Leu Ala Leu Thr Ala Ala Ile Lys Gln
65                  70                  75                  80

Ala Ala Gly Phe Ala Ser Lys Thr Glu Thr Glu Pro Val Phe Trp Tyr
                85                  90                  95

Tyr Val Lys Glu Val Leu Asn Lys His Glu Leu Gln Arg Phe Tyr Ser
            100                 105                 110

Leu Arg His Ile Ala Ser Asp Val Gly Arg Gly Arg Ala Trp Leu Arg
        115                 120                 125

Cys Ala Leu Asn Glu His Ser Leu Glu Arg Tyr Leu His Met Leu Leu
130                 135                 140

Ala Asp Arg Cys Arg Leu Ser Thr Phe Tyr Glu Asp Trp Ser Phe Val
145                 150                 155                 160

Met Asp Glu Glu Arg Ser Ser Met Leu Pro Thr Met Ala Ala Gly Leu
                165                 170                 175

Asn Ser Ile Leu Phe Ala Ile Asn Ile Asp Asn Lys Asp Leu Asn Gly
            180                 185                 190
```

```
Gln Ser Lys Phe Ala Pro Thr Val Ser Asp Leu Leu Lys Glu Ser Thr
            195                 200                 205
Gln Asn Val Thr Ser Leu Leu Lys Glu Ser Thr Gln Gly Val Ser Ser
            210                 215                 220
Leu Phe Arg Glu Ile Thr Ala Ser Ser Ala Val Ser Ile Leu Ile Lys
225                 230                 235                 240
Pro Glu Gln Glu Thr Asp Pro Cys Leu Ser Cys Pro Gly Met Ser Val
                245                 250                 255
Leu Met Pro Asn Ala Lys Arg Ser Gly Arg Arg Lys Arg Lys Xaa Pro
            260                 265                 270
Thr Xaa Ser His Leu Met Met Arg Lys Met Ser Arg Thr Leu Gly Thr
            275                 280                 285
Cys Leu Lys Arg His Leu Gly Gln Gly Arg Ala Gln Arg Thr Thr Pro
            290                 295                 300
Thr Ala Pro Leu Ser Ile Ser Cys Pro Pro Leu Lys Ala Pro Ser Gly
305                 310                 315                 320
Leu Thr Pro Met Glu Ser Glu Gln Gln Leu Met Glu Asn Xaa Phe Pro
                325                 330                 335
Val Phe Glu Arg Gly Val Trp Val Pro Glu Ala Xaa Cys Glu Lys His
            340                 345                 350
Arg Xaa Xaa Arg Cys Gly Xaa Lys Arg Arg Xaa Arg Val Trp Lys Leu
            355                 360                 365
Ile Arg Lys Glu Ala Gln Gly Pro Leu Gly Val Ala Arg Glu Ala Thr
            370                 375                 380
Gly Arg Glu His Leu Pro Leu Pro Asp Ala Gln Leu Gly Ser Ala Glu
385                 390                 395                 400
Gly Ala Ala Gln Xaa Leu Arg His Pro Leu Pro Cys Gln Trp Arg Gly
                405                 410                 415
Leu Leu Gln Pro Ser Arg Cys Pro Pro Arg Lys Pro Gly Glu Arg Asp
            420                 425                 430
Arg Thr Arg Gly Pro Arg Ser Pro Gly Ser Trp Thr Ser Val Gln Cys
            435                 440                 445
Gly Ser Gln Leu Ser Arg Pro Arg Lys Ser Ser Glu Gln Pro Val Thr
            450                 455                 460
Ser Ala Ser Val Pro Glu Ser Met Thr Ile Ser Glu Leu Arg Gln Ala
465                 470                 475                 480
Thr Val Ala Met Met Asn Arg Lys Asp Glu Leu Glu Glu Glu Asn Arg
                485                 490                 495
Ser Leu Arg Asn Leu Leu Asp Gly Glu Met Glu His Ser Ala Ala Leu
            500                 505                 510
Arg Gln Glu Val Asp Thr Leu Lys Arg Lys Val Ala Gln Glu Gln Glu
            515                 520                 525
Arg Gln Gly Met Lys Val Gln Ala Leu Ala Ser Tyr Leu Cys Tyr Phe
            530                 535                 540
Val Arg Arg Phe Xaa Pro His Val Arg Thr Met Trp Trp Arg Asn Gly
545                 550                 555                 560
Gly Arg Glu Lys Ser Asn Ser Ser Xaa Xaa Ser His Leu Ser Ser Trp
                565                 570                 575
Ile Gln Ser Phe Leu Lys Leu Cys Phe Leu Trp Thr Phe His Val Cys
            580                 585                 590
Glu Pro Ile Asn Cys Phe His Ser Leu Lys Lys Lys
            595                 600
```

```
<210> SEQ ID NO 3
<211> LENGTH: 2631
<212> TYPE: DNA
<213> ORGANISM: Homo sapiens
<220> FEATURE:
<221> NAME/KEY: misc_feature
<222> LOCATION: (1081)..(1081)
<223> OTHER INFORMATION: n is a, c, g, or t
<220> FEATURE:
<221> NAME/KEY: misc_feature
<222> LOCATION: (1102)..(1102)
<223> OTHER INFORMATION: n is a, c, g, or t
<220> FEATURE:
<221> NAME/KEY: misc_feature
<222> LOCATION: (1120)..(1120)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1129)..(1129)
<223> OTHER INFORMATION: n is a, c, g, or t
<220> FEATURE:
<221> NAME/KEY: misc_feature
<222> LOCATION: (1135)..(1135)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1248)..(1249)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1297)..(1297)
<223> OTHER INFORMATION: n is a, c, g, or t
<220> FEATURE:
<221> NAME/KEY: misc_feature
<222> LOCATION: (1310)..(1310)
<223> OTHER INFORMATION: n is a, c, g, or t
<220> FEATURE:
<221> NAME/KEY: misc_feature
<222> LOCATION: (1322)..(1322)
<223> OTHER INFORMATION: n is a, c, g, or t
<220> FEATURE:
<221> NAME/KEY: misc_feature
<222> LOCATION: (1345)..(1345)
<223> OTHER INFORMATION: n is a, c, g, or t
<220> FEATURE:
<221> NAME/KEY: misc_feature
<222> LOCATION: (1409)..(1409)
<223> OTHER INFORMATION: n is a, c, g, or t
```

```
<220> FEATURE:
<221> NAME/KEY: misc_feature
<222> LOCATION: (1423)..(1423)
<223> OTHER INFORMATION: n is a, c, g, or t
<220> FEATURE:
<221> NAME/KEY: misc_feature
<222> LOCATION: (1445)..(1445)
<223> OTHER INFORMATION: n is a, c, g, or t
<220> FEATURE:
<221> NAME/KEY: misc_feature
<222> LOCATION: (1452)..(1452)
<223> OTHER INFORMATION: n is a, c, g, or t
<220> FEATURE:
<221> NAME/KEY: misc_feature
<222> LOCATION: (1459)..(1459)
<223> OTHER INFORMATION: n is a, c, g, or t
<220> FEATURE:
<221> NAME/KEY: misc_feature
<222> LOCATION: (1478)..(1478)
<223> OTHER INFORMATION: n is a, c, g, or t
<220> FEATURE:
<221> NAME/KEY: misc_feature
<222> LOCATION: (1498)..(1498)
<223> OTHER INFORMATION: n is a, c, g, or t
<220> FEATURE:
<221> NAME/KEY: misc_feature
<222> LOCATION: (1507)..(1508)
<223> OTHER INFORMATION: n is a, c, g, or t
<220> FEATURE:
<221> NAME/KEY: misc_feature
<222> LOCATION: (1520)..(1520)
<223> OTHER INFORMATION: n is a, c, g, or t
<220> FEATURE:
<221> NAME/KEY: misc_feature
<222> LOCATION: (1534)..(1534)
<223> OTHER INFORMATION: n is a, c, g, or t
<220> FEATURE:
<221> NAME/KEY: misc_feature
<222> LOCATION: (1540)..(1540)
<223> OTHER INFORMATION: n is a, c, g, or t
<220> FEATURE:
<221> NAME/KEY: misc_feature
<222> LOCATION: (1546)..(1546)
<223> OTHER INFORMATION: n is a, c, g, or t
<220> FEATURE:
<221> NAME/KEY: misc_feature
<222> LOCATION: (1557)..(1557)
<223> OTHER INFORMATION: n is a, c, g, or t
<220> FEATURE:
<221> NAME/KEY: misc_feature
<222> LOCATION: (1713)..(1713)
<223> OTHER INFORMATION: n is a, c, g, or t
<220> FEATURE:
<221> NAME/KEY: misc_feature
<222> LOCATION: (1895)..(1895)
<223> OTHER INFORMATION: n is a, c, g, or t
<220> FEATURE:
<221> NAME/KEY: misc_feature
<222> LOCATION: (1900)..(1900)
<223> OTHER INFORMATION: n is a, c, g, or t
<220> FEATURE:
<221> NAME/KEY: misc_feature
<222> LOCATION: (1934)..(1934)
<223> OTHER INFORMATION: n is a, c, g, or t
<220> FEATURE:
<221> NAME/KEY: misc_feature
<222> LOCATION: (1942)..(1942)
<223> OTHER INFORMATION: n is a, c, g, or t
<220> FEATURE:
<221> NAME/KEY: misc_feature
<222> LOCATION: (1951)..(1951)
<223> OTHER INFORMATION: n is a, c, g, or t
<220> FEATURE:
<221> NAME/KEY: misc_feature
<222> LOCATION: (1962)..(1962)
<223> OTHER INFORMATION: n is a, c, g, or t
<220> FEATURE:
<221> NAME/KEY: misc_feature
<222> LOCATION: (1967)..(1967)
<223> OTHER INFORMATION: n is a, c, g, or t
```

-continued

```
<220> FEATURE:
<221> NAME/KEY: misc_feature
<222> LOCATION: (1974)..(1974)
<223> OTHER INFORMATION: n is a, c, g, or t
<220> FEATURE:
<221> NAME/KEY: misc_feature
<222> LOCATION: (1984)..(1984)
<223> OTHER INFORMATION: n is a, c, g, or t
<220> FEATURE:
<221> NAME/KEY: misc_feature
<222> LOCATION: (1988)..(1988)
<223> OTHER INFORMATION: n is a, c, g, or t
<220> FEATURE:
<221> NAME/KEY: misc_feature
<222> LOCATION: (1994)..(1994)
<223> OTHER INFORMATION: n is a, c, g, or t
<220> FEATURE:
<221> NAME/KEY: misc_feature
<222> LOCATION: (2005)..(2005)
<223> OTHER INFORMATION: n is a, c, g, or t
<220> FEATURE:
<221> NAME/KEY: misc_feature
<222> LOCATION: (2012)..(2012)
<223> OTHER INFORMATION: n is a, c, g, or t
<220> FEATURE:
<221> NAME/KEY: misc_feature
<222> LOCATION: (2024)..(2024)
<223> OTHER INFORMATION: n is a, c, g, or t
<220> FEATURE:
<221> NAME/KEY: misc_feature
<222> LOCATION: (2030)..(2030)
<223> OTHER INFORMATION: n is a, c, g, or t
<220> FEATURE:
<221> NAME/KEY: misc_feature
<222> LOCATION: (2044)..(2044)
<223> OTHER INFORMATION: n is a, c, g, or t
<220> FEATURE:
<221> NAME/KEY: misc_feature
<222> LOCATION: (2059)..(2059)
<223> OTHER INFORMATION: n is a, c, g, or t
<220> FEATURE:
<221> NAME/KEY: misc_feature
<222> LOCATION: (2067)..(2067)
<223> OTHER INFORMATION: n is a, c, g, or t
<220> FEATURE:
<221> NAME/KEY: misc_feature
<222> LOCATION: (2090)..(2090)
<223> OTHER INFORMATION: n is a, c, g, or t
<220> FEATURE:
<221> NAME/KEY: misc_feature
<222> LOCATION: (2098)..(2099)
<223> OTHER INFORMATION: n is a, c, g, or t
<220> FEATURE:
<221> NAME/KEY: misc_feature
<222> LOCATION: (2107)..(2107)
<223> OTHER INFORMATION: n is a, c, g, or t
<220> FEATURE:
<221> NAME/KEY: misc_feature
<222> LOCATION: (2113)..(2113)
<223> OTHER INFORMATION: n is a, c, g, or t
<220> FEATURE:
<221> NAME/KEY: misc_feature
<222> LOCATION: (2119)..(2119)
<223> OTHER INFORMATION: n is a, c, g, or t
<220> FEATURE:
<221> NAME/KEY: misc_feature
<222> LOCATION: (2128)..(2128)
<223> OTHER INFORMATION: n is a, c, g, or t
<220> FEATURE:
<221> NAME/KEY: misc_feature
<222> LOCATION: (2136)..(2136)
<223> OTHER INFORMATION: n is a, c, g, or t
<220> FEATURE:
<221> NAME/KEY: misc_feature
<222> LOCATION: (2143)..(2143)
<223> OTHER INFORMATION: n is a, c, g, or t
<220> FEATURE:
<221> NAME/KEY: misc_feature
<222> LOCATION: (2148)..(2148)
<223> OTHER INFORMATION: n is a, c, g, or t
```

```
<220> FEATURE:
<221> NAME/KEY: misc_feature
<222> LOCATION: (2165)..(2165)
<223> OTHER INFORMATION: n is a, c, g, or t
<220> FEATURE:
<221> NAME/KEY: misc_feature
<222> LOCATION: (2172)..(2172)
<223> OTHER INFORMATION: n is a, c, g, or t
<220> FEATURE:
<221> NAME/KEY: misc_feature
<222> LOCATION: (2192)..(2192)
<223> OTHER INFORMATION: n is a, c, g, or t
<220> FEATURE:
<221> NAME/KEY: misc_feature
<222> LOCATION: (2206)..(2206)
<223> OTHER INFORMATION: n is a, c, g, or t
<220> FEATURE:
<221> NAME/KEY: misc_feature
<222> LOCATION: (2220)..(2221)
<223> OTHER INFORMATION: n is a, c, g, or t
<220> FEATURE:
<221> NAME/KEY: misc_feature
<222> LOCATION: (2226)..(2226)
<223> OTHER INFORMATION: n is a, c, g, or t
<220> FEATURE:
<221> NAME/KEY: misc_feature
<222> LOCATION: (2245)..(2245)
<223> OTHER INFORMATION: n is a, c, g, or t
<220> FEATURE:
<221> NAME/KEY: misc_feature
<222> LOCATION: (2253)..(2253)
<223> OTHER INFORMATION: n is a, c, g, or t
<220> FEATURE:
<221> NAME/KEY: misc_feature
<222> LOCATION: (2294)..(2294)
<223> OTHER INFORMATION: n is a, c, g, or t
<220> FEATURE:
<221> NAME/KEY: misc_feature
<222> LOCATION: (2327)..(2327)
<223> OTHER INFORMATION: n is a, c, g, or t
<220> FEATURE:
<221> NAME/KEY: misc_feature
<222> LOCATION: (2427)..(2427)
<223> OTHER INFORMATION: n is a, c, g, or t

<400> SEQUENCE: 3
cccctctcac agcccaggcc atccaagagg ggctgaggaa agagcccatc caccgcgtgt    60
ctgcagcgga gctgggaggg aaggtgaacc gggcactaca gcaagtggga ggtctgaaga   120
gcccttggag gggagaatat aaagaaccaa gacatccacc gccaaatcaa gccaattacc   180
accagaccct ccatgcccag ccgagagagc tttcgccaag ggccccaggg ccccggccag   240
ctgaggagac aacaggcaga gcccctaagc tccagcctcc tctcccacca gagccccag    300 agccaaacaa gtcctctccc ttgactttga gcaaggagga gtctgggatg tgggaaccct   360
tacctctgtc ctccctggag ccagcccctg ccagaaaccc cagctcacca gagcggaaag   420
caaccgtccc ggagcaggaa ctgcagcagc tggaaataga attattcctc aacagcctgt   480
cccagccatt ttctctggag gagcaggagc aaattctctc gtgcctcagc atcgacagcc   540
tctccctgtc ggatgacagt gagaagaacc catcaaaggc ctctcaaagc tcgcgggaca   600
ccctgagctc aggcgtacac tcctggagca gccaggccga ggctcgaagc tccagctgga   660
acatggtgct ggcccggggg cggccccaccg acaccccaag ctatttcaat ggtgtgaaag   720
tccaaataca gtctcttaat ggtgaacacc tgcacatccg ggagttccac cgggtcaaag   780
tgggagacat cgccactggc atcagcagcc agatcccagc tgcagccttc agcttggtca   840
ccaaagacgg gcagcctgtt cgctacgaca tggaggtgcc agactcgggc atcgacctgc   900
agtgcacact ggcccctgat ggcagcttcg cctggagctg gagggtcaag catgccagc   960 tggagaacag gccctaaccc tgccctccac cgccggctcc acactgccgg aaagcagcct  1020
```

```
tcctgctcgg tgcacgatgc tgccctgaaa acacaggctc agccgttccc agggatytg    1080 nccagccccc cggctcarca gntgggaacc agggcctcgn cagcnagcna aggtnggggg    1140
caagcnagaa tgcctcccag gatttcacan cctgagcccn tgccccancc ctgctgaada    1200
aaacaytncc gccacgtgaa gagacagaag gaggatggnc aggagttnna cctygggaa     1260 acaaaacagg gatcttntt ctgccctgc tccagtncga gttggcctgn acccgcttgg     1320
antcagtgac catttgttgg cagancaggg gagagcagct tccagcctgg gtcagaaggg    1380
gtgggcgagc ccttcggccc ctcacctnc caggctgctg tgnagagtgt caagtgtgta    1440
agggncccaa anctcaggnt tcagtgcaga accaggtnca gcaggtatgc ccgcccgnta    1500
ggttaanngg gggccctctn aaacccttg cctnggcctn cacctnggcc agctcanccc    1560
cttttgggtg taggggaaaaa gaatgcctga ccctgggaag gctwccctgg tagaatacac    1620 cacactttc aggttgttgc aacacaggtc ctgagttgac ctctggttca gccaaggacc    1680
aaagaaggtg tgtaagtgaa gtggttctca gtnccccaga catgtgcccc tttgctgctg    1740
gctaccactc ttccccagag cagcaggccc cgagccctt caggcccagc actgccccag    1800
actcgctggc actcagttcc ctcatctgta aaggtgaagg gtgatgcagg atatgcctga    1860
caggaacagt ctgtggatgg acatgatcag tgctnaaggn aaagcagcag agagagacgy    1920
tccggcgccc cagnccccac tnatcagtgt nccagcgtgc tnggttnccc cagnagcaca    1980
gctncagnca tcancactga cactncaccc tngccctgcc cctnggccan gagggtactg    2040
ccgnacggca ctttgcacnt ctgatgnacc tcaaagcact ttcatggctn gccctctnng    2100
gcagggncag ggncagggnc agtgacancnt gtaggnagca tangcaangc caggagatgg    2160
ggtgnaaggg ancacagtct tgagctgtcc ancatgcatg tgactnccc aaacctcttn    2220 nccagnattt ctctaagaat agcancccc ttnccccatt gccccagctt agcctcttct    2280
cccaggggag ctanctcagg actcacgtag cattaaatca gctgtgnaat cgtcaggggg    2340
tgtctgctag cctcaacctc ctggggcagg ggacgccgag actccgtggg agaagctcat    2400
tcccacatct tgccaagaca gccttngtc cagctgtcca cattgagtca gactgctccc    2460
ggggagagag ccccggcccc cagcacataa agaactgcag ccttggtact gcagagtctg    2520
ggttgtagag aactcttgt aagcaataaa gtttggggtg atgacaaatg ttaaaaaaag    2580
gccttcgtgg cctcgaatca agcttatcga taccgtcgac ctcgaggggg g           2631
```

<210> SEQ ID NO 4
<211> LENGTH: 1253
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, or t

<400> SEQUENCE: 4

```
cattggagtc acgcggtggc ggcgctctag aatagtggat ccccgggctg canggaattc    60
gattcgagcc cacgaaggcc ccttcttctg tggtcgcggc acgtttacag ccgcaagcac   120
ccagcggcag ctgaaggagg cttttgagag gctcctgccc caggtggagg cggcccgcaa   180
ggccatccgc gccgctcagg tggagcgcta tgtcccgaa cacgagcgat gctgctggtg    240
cctgtgctgc ggctgtgagg tgcgggaaca cctgagccat ggaaacctga cggtgctgta    300 cgggggggctg ctggagcatc tggccagccc agagcacaag aaagcaacca acaaattctg    360
gtgggagaac aaagctgagg tccagatgaa agagaagttt ctggtcactc cccaggatta    420
```

```
tgcgcgattc aagaaatcca tggtgaaagg tttggattcc tatgaagaaa aggaggataa      480
agtgatcaag gagatggcag ctcagatccg tgaggtggag cagagccgac aggaggtggt      540
tcggtctgtc ttagagcctc aggcagtgcc agacccagaa gagggctctt cagcacctag      600
aagctggaaa gggatgaaca gccaagtagc ttccagctta cagcagccct caaatttgga      660
cctgccacca gctccagagc ttgactggat ggagacagga ccatctctga cattcattgg      720
ccatcaggat ataccaggag ttggtaacat ccactcaggt gccacacctc cctggatgat      780
ccaagatgaa gaatacattg ctgggaacca agaaatagga ccatcctatg aagaatttct      840
taaagaaaag gaaaaacaga agttgaaaaa actccccccca gaccgagttg gggccaactt      900
tgatcacagc tccaggacca gtgcaggctg gctgccctct tttgggccgc gtctggaata      960
atggacgccg ctggcagtcc agacatcaac tccaaaactg aagctgcagc aatgaagaag     1020
cagtcacata cagaaaaaag ctaatcatgc tctctaccaa ctaccatgag gctaaaagcc     1080
aaagtcaacc aaaccccctat tataccttcc acccaaattc tttatcattg tctttcttag     1140
gaaacagaca tactcattca tttgatttaa taaagtttta ttttcggcc ttcgtggcct      1200 cgaatcaagc ttatcgatac cgtcgacctc gaggggggggc cgtacccact ttt            1253
```

<210> SEQ ID NO 5
<211> LENGTH: 417
<212> TYPE: PRT
<213> ORGANISM: Homo sapiens
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (388)..(388)
<223> OTHER INFORMATION: Xaa can be any naturally occurring amino acid

<400> SEQUENCE: 5

Ile Gly Val Thr Arg Trp Arg Arg Ser Arg Ile Val Asp Pro Arg Ala
1               5                   10                  15

Ala Xaa Asn Ser Ile Arg Ala His Glu Gly Pro Phe Phe Cys Gly Arg
            20                  25                  30

Gly Thr Phe Thr Ala Ala Ser Thr Gln Arg Gln Leu Lys Glu Ala Phe
        35                  40                  45

Glu Arg Leu Leu Pro Gln Val Glu Ala Ala Arg Lys Ala Ile Arg Ala
    50                  55                  60

Ala Gln Val Glu Arg Tyr Val Pro Glu His Glu Arg Cys Cys Trp Cys
65                  70                  75                  80

Leu Cys Cys Gly Cys Glu Val Arg Glu His Leu Ser His Gly Asn Leu
                85                  90                  95

Thr Val Leu Tyr Gly Gly Leu Leu Glu His Leu Ala Ser Pro Glu His

-continued

```
                          100                 105                 110
Lys Lys Ala Thr Asn Lys Phe Trp Trp Glu Asn Lys Ala Glu Val Gln
            115                 120                 125

Met Lys Glu Lys Phe Leu Val Thr Pro Gln Asp Tyr Ala Arg Phe Lys
130                 135                 140

Lys Ser Met Val Lys Gly Leu Asp Ser Tyr Glu Lys Glu Asp Lys
145                 150                 155                 160

Val Ile Lys Glu Met Ala Ala Gln Ile Arg Glu Val Glu Gln Ser Arg
            165                 170                 175

Gln Glu Val Val Arg Ser Val Leu Glu Pro Gln Ala Val Pro Asp Pro
            180                 185                 190

Glu Glu Gly Ser Ser Ala Pro Arg Ser Trp Lys Gly Met Asn Ser Gln
            195                 200                 205

Val Ala Ser Ser Leu Gln Gln Pro Ser Asn Leu Asp Leu Pro Pro Ala
            210                 215                 220

Pro Glu Leu Asp Trp Met Glu Thr Gly Pro Ser Leu Thr Phe Ile Gly
225                 230                 235                 240

His Gln Asp Ile Pro Gly Val Gly Asn Ile His Ser Gly Ala Thr Pro
            245                 250                 255

Pro Trp Met Ile Gln Asp Glu Glu Tyr Ile Ala Gly Asn Gln Glu Ile
            260                 265                 270

Gly Pro Ser Tyr Glu Glu Phe Leu Lys Glu Lys Glu Lys Gln Lys Leu
            275                 280                 285

Lys Lys Leu Pro Pro Asp Arg Val Gly Ala Asn Phe Asp His Ser Ser
            290                 295                 300

Arg Thr Ser Ala Gly Trp Leu Pro Ser Phe Gly Pro Arg Leu Glu Xaa
305                 310                 315                 320

Trp Thr Pro Leu Ala Val Gln Thr Ser Thr Pro Lys Leu Lys Leu Gln
            325                 330                 335

Gln Xaa Arg Ser Ser His Ile Lys Lys Ala Asn His Ala Leu Tyr
            340                 345                 350

Gln Leu Pro Xaa Gly Xaa Lys Pro Lys Ser Thr Lys Pro Leu Leu Tyr
            355                 360                 365

Leu Pro Pro Lys Phe Phe Ile Ile Val Phe Leu Arg Lys Gln Thr Tyr
370                 375                 380

Ser Phe Ile Xaa Phe Asn Lys Val Leu Phe Gly Leu Arg Gly Leu
385                 390                 395                 400

Glu Ser Ser Leu Ser Ile Pro Ser Thr Ser Arg Gly Gly Arg Thr His
            405                 410                 415

Phe
```

<210> SEQ ID NO 6
<211> LENGTH: 4596
<212> TYPE: DNA
<213> ORGANISM: Homo sapiens

<400> SEQUENCE: 6

| | | | | | |
|---|---|---|---|---|---|
| agcgggggga | ctgtgccgtg | tggaacgtgt | agctgttgaa | ggtggactct | gttaccattg | 60 |
| aggatgtttg | gaggatgagt | atgtgtggca | gaggcacaca | taaacaggca | gagacccttt | 120 |
| gcccctgcct | ttctccccca | acccaaggct | gacctgtgtt | ctcccaggtc | tgggattcta | 180 |
| agtgacctgc | tctgtgtttg | gtctctctca | ggatgagcac | aagcctggga | gatggcagtg | 240 |
| atggaaatgg | cctgcccagg | tgccctggc | tcagcagtgg | ggcagcagaa | ggaactcccc | 300 |
| aagccaaagg | agaagacgcc | gccactgggg | aagaaacaga | gctccgtcta | caagcttgag | 360 |

-continued

```
gccgtggaga agagccctgt gttctgcgga aagtgggaga tcctgaatga cgtgattacc      420
aagggcacag ccaaggaagg ctccgaggca gggccagctg ccatctctat catcgcccag      480
gctgagtgtg agaatagcca agagttcagc cccaccttt cagaacgcat tttcatcgct       540
gggtccaaac agtacagcca gtccgagagt cttgatcaga tccccaacaa tgtggcccat     600
gctacagagg gcaaaatggc ccgtgtgtgt tggaagggaa agcgtcgcag caaagcccgg      660
aagaaacgga agaagaagag ctcaaagtcc ctggctcatg caggagtggc cttggccaaa      720
cccctcccca ggacccctga gcaggagagc tgcaccatcc cagtgcagga ggatgagtct      780
ccactcggcg ccccatatgt tagaaacacc ccgcagttca ccaagcctct gaaggaacca      840
ggccttgggc aactctgttt taagcagctt ggcgagggcc tacggccggc tctgcctcga      900
tcagaactcc acaaactgat cagccccttg caatgtctga accacgtgtg gaaactgcac      960 caccccagg acggaggccc cctgcccctg cccacgcacc ccttcccta tagcagactg       1020 cctcatccct tccattcca ccctctccag ccctggaaac ctcaccctct ggagtccttc       1080
ctgggcaaac tggcctgtgt agacagccag aaaccttgc ctgacccaca cctgagcaaa      1140
ctggcctgtg tagacagtcc aaagcccctg cctggcccac acctggagcc cagctgcctg     1200
tctcgtggtg cccatgagaa gttttctgtg gaggaatacc tagtgcatgc tctgcaaggc     1260
agcgtgagct caagccaggc ccacagcctg accagcctgg ccaagacctg gcagcacgg      1320 ggctccagat cccgggagcc cagccccaaa actgaggaca cgagggtgt cctgctcact      1380 gagaaactca agccagtgga ttatgagtac cgagaagaag tccactgggc cacgcaccag     1440
ctccgcctgg gcagaggctc cttcggagag gtgcacagga tggaggacaa gcagactggc     1500
ttccagtgcg ctgtcaaaaa ggtgcgcctg gaagtatttc gggcagagga gctgatggca     1560
tgtgcaggat tgacctcacc cagaattgtc cctttgtatg gagctgtgag agaagggcct     1620
tgggtcaaca tcttcatgga gctgctgaa ggtggctccc tgggccagct ggtcaaggag      1680
cagggctgtc tcccagagga ccgggccctg tactacctgg gccaggccct ggagggtctg     1740
gaatacctcc actcacgaag gattctgcat ggggacgtca agctgacaa cgtgctcctg      1800 tccagcgatg ggagccacgc agccctctgt gactttggcc atgctgtgtg tcttcaacct     1860
gatggcctgg gaaagtcctt gctcacaggg gactacatcc ctggcacaga gacccacatg     1920
gctccggagg tggtgctggg caggagctgc gacgccaagg tggatgtctg gagcagctgc     1980
tgtatgatgc tgcacatgct caacggctgc caccccgga ctcagttctt ccgagggccg      2040
ctctgcctca agattgccag cgagcctccg cctgtgaggg agatcccacc ctcctgcgcc     2100
cctctcacag cccaggccat ccaagagggg ctgaggaaag agcccatcca ccgcgtgtct     2160
gcagcggagc tgggagggaa ggtgaaccgg gcactacagc aagtgggagg tctgaagagc     2220
ccttggaggg gagaatataa agaaccaaga catccaccgc caaatcaagc caattaccac     2280
cagaccctcc atgcccagcc gagagagctt tcgccaaggg ccccagggcc ccggccagct    2340
gaggagacaa caggcagagc ccctaagctc cagcctcctc tcccaccaga gcccccagag    2400
ccaaacaagt ctcctccctt gactttgagc aaggaggagt ctgggatgtg gaaccctta     2460 cctctgtcct ccctggagcc agccctgcc agaaacccca gctcaccaga gcggaaagca     2520
accgtcccgg agcaggaact gcagcagctg gaaatagaat tattcctcaa cagcctgtcc    2580
cagccatttt ctctggagga gcaggagcaa attctctcgt gcctcagcat cgacagcctc    2640
tccctgtcga tgacagtga aagaaccca tcaaaggcct ctcaaagctc gcgggacacc      2700
ctgagctcag gcgtacactc ctggagcagc caggccgagg ctcgaagctc cagctggaac    2760
```

```
atggtgctgg cccggggcg gcccaccgac accccaagct atttcaatgg tgtgaaagtc    2820
caaatacagt ctcttaatgg tgaacacctg cacatccggg agttccaccg ggtcaaagtg    2880
ggagacatcg ccactggcat cagcagccag atcccagctg cagccttcag cttggtcacc    2940
aaagacgggc agcctgttcg ctacgacatg gaggtgccag actcgggcat cgacctgcag    3000
tgcacactgg cccctgatgg cagcttcgcc tggagctgga gggtcaagca tggccagctg    3060
gagaacaggc cctaaccctg ccctccaccg ccggctccac actgccggaa agcagccttc    3120
ctgctcggtg cacgatgctg ccctgaaaac acaggctcag ccgttcccag gggattgcca    3180
gccccccggc tcacagtggg aaccagggcc tcgcagcagc aaggtggggg caagcagaat    3240
gcctcccagg atttcacacc tgagccctgc ccacccctgc tgaaaaaaca tccgccacgt    3300
gaagagacag aaggaggatg gcaggagtta cctggggaaa caaaacaggg atctttttct    3360
gccctgctc cagtcgagtt ggcctgaccc gcttggatca gtgaccattt gttggcagac    3420
aggggagagc agcttccagc ctgggtcaga aggggtgggc gagcccttcg gcccctcacc    3480
ctccaggctg ctgtgagagt gtcaagtgtg taagggccca aactcaggtt cagtgcagaa    3540
ccaggtcagc aggtatgccc gcccgtaggt taagggggcc ctctaaaccc cttgcctggc    3600
ctcacctggc cagctcaccc cttttgggtg taggggaaaa gaatgcctga ccctgggaag    3660
gctccctggt agaatacacc acactttttca ggttgttgca acacaggtcc tgagttgacc    3720
tctggttcag ccaaggacca agaaggtgt gtaagtgaag tggttctcag tccccagaca    3780
tgtgccccctt tgctgctggc taccactctt ccccagagca gcaggccccg agccccttca    3840
ggcccagcac tgccccagac tcgctggcac tcagttccct catctgtaaa ggtgaagggt    3900
gatgcaggat atgcctgaca ggaacagtct gtggatggac atgatcagtg ctaaggaaag    3960
cagcagagag agacgtccgg cgccccagcc ccactatcag tgtccagcgt gctggttccc    4020
cagagcacag ctcagcatca cactgacact caccctgccc tgcccctggc cagagggtac    4080
tgccgacggc actttgcact ctgatgacct caaagcactt tcatggctgc cctctggcag    4140
ggcagggcag ggcagtgaca ctgtaggagc atagcaagcc aggagatggg gtgaagggac    4200
acagtcttga gctgtccaca tgcatgtgac tcctcaaacc tcttccagat ttctctaaga    4260
atagcacccc cttccccatt gccccagctt agcctcttct cccaggggag ctactcagga    4320
ctcacgtagc attaaatcag ctgtgaatcg tcaggggtg tctgctagcc tcaacctcct    4380
ggggcagggg acgccgagac tccgtgggag aagctcattc ccacatcttg ccaagacagc    4440
cttttgtccag ctgtccacat tgagtcagac tgctcccggg gagagagccc cggcccccag    4500
cacataaaga actgcagcct tggtactgca gagtctgggt tgtagagaac tctttgtaag    4560
caataaagtt tgggggtgatg acaaatgtta aaaaaa    4596
```

<210> SEQ ID NO 7
<211> LENGTH: 947
<212> TYPE: PRT
<213> ORGANISM: Homo sapiens

<400> SEQUENCE: 7

Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
            20                  25                  30

Gly Lys Lys Gln Ser Ser Val Tyr Lys Leu Glu Ala Val Glu Lys Ser
        35                  40                  45

```
Pro Val Phe Cys Gly Lys Trp Glu Ile Leu Asn Asp Val Ile Thr Lys
 50                  55                  60

Gly Thr Ala Lys Glu Gly Ser Glu Ala Gly Pro Ala Ala Ile Ser Ile
 65                  70                  75                  80

Ile Ala Gln Ala Glu Cys Glu Asn Ser Gln Glu Phe Ser Pro Thr Phe
                 85                  90                  95

Ser Glu Arg Ile Phe Ile Ala Gly Ser Lys Gln Tyr Ser Gln Ser Glu
                100                 105                 110

Ser Leu Asp Gln Ile Pro Asn Asn Val Ala His Ala Thr Glu Gly Lys
            115                 120                 125

Met Ala Arg Val Cys Trp Lys Gly Lys Arg Ser Lys Ala Arg Lys
130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Ser Cys Thr Ile
                165                 170                 175

Pro Val Gln Glu Asp Glu Ser Pro Leu Gly Ala Pro Tyr Val Arg Asn
                180                 185                 190

Thr Pro Gln Phe Thr Lys Pro Leu Lys Glu Pro Gly Leu Gly Gln Leu
                195                 200                 205

Cys Phe Lys Gln Leu Gly Glu Gly Leu Arg Pro Ala Leu Pro Arg Ser
                210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
                260                 265                 270

Gln Pro Trp Lys Pro His Pro Leu Glu Ser Phe Leu Gly Lys Leu Ala
                275                 280                 285

Cys Val Asp Ser Gln Lys Pro Leu Pro Asp Pro His Leu Ser Lys Leu
                290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Tyr
                325                 330                 335

Leu Val His Ala Leu Gln Gly Ser Val Ser Ser Gln Ala His Ser
                340                 345                 350

Leu Thr Ser Leu Ala Lys Thr Trp Ala Ala Arg Gly Ser Arg Ser Arg
                355                 360                 365

Glu Pro Ser Pro Lys Thr Glu Asp Asn Glu Gly Val Leu Leu Thr Glu
                370                 375                 380

Lys Leu Lys Pro Val Asp Tyr Glu Tyr Arg Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
                420                 425                 430

Leu Glu Val Phe Arg Ala Glu Glu Leu Met Ala Cys Ala Gly Leu Thr
                435                 440                 445

Ser Pro Arg Ile Val Pro Leu Tyr Gly Ala Val Arg Glu Gly Pro Trp
                450                 455                 460

Val Asn Ile Phe Met Glu Leu Leu Glu Gly Gly Ser Leu Gly Gln Leu
465                 470                 475                 480
```

-continued

Val Lys Glu Gln Gly Cys Leu Pro Glu Asp Arg Ala Leu Tyr Tyr Leu
            485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
            515                 520                 525

His Ala Ala Leu Cys Asp Phe Gly His Ala Val Cys Leu Gln Pro Asp
            530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                    565                 570                 575

Val Asp Val Trp Ser Ser Cys Cys Met Met Leu His Met Leu Asn Gly
            580                 585                 590

Cys His Pro Trp Thr Gln Phe Phe Arg Gly Pro Leu Cys Leu Lys Ile
            595                 600                 605

Ala Ser Glu Pro Pro Pro Val Arg Glu Ile Pro Pro Ser Cys Ala Pro
610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                    645                 650                 655

Gln Val Gly Gly Leu Lys Ser Pro Trp Arg Gly Glu Tyr Lys Glu Pro
                660                 665                 670

Arg His Pro Pro Asn Gln Ala Asn Tyr His Gln Thr Leu His Ala
            675                 680                 685

Gln Pro Arg Glu Leu Ser Pro Arg Ala Pro Gly Pro Arg Pro Ala Glu
            690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                    725                 730                 735

Ser Gly Met Trp Glu Pro Leu Pro Leu Ser Ser Leu Glu Pro Ala Pro
            740                 745                 750

Ala Arg Asn Pro Ser Ser Pro Glu Arg Lys Ala Thr Val Pro Glu Gln
            755                 760                 765

Glu Leu Gln Gln Leu Glu Ile Glu Leu Phe Leu Asn Ser Leu Ser Gln
            770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                    805                 810                 815

Ser Gln Ser Ser Arg Asp Thr Leu Ser Ser Gly Val His Ser Trp Ser
            820                 825                 830

Ser Gln Ala Glu Ala Arg Ser Ser Trp Asn Met Val Leu Ala Arg
            835                 840                 845

Gly Arg Pro Thr Asp Thr Pro Ser Tyr Phe Asn Gly Val Lys Val Gln
            850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                    885                 890                 895

Ala Ala Phe Ser Leu Val Thr Lys Asp Gly Gln Pro Val Arg Tyr Asp

```
                        900                 905                 910
Met Glu Val Pro Asp Ser Gly Ile Asp Leu Gln Cys Thr Leu Ala Pro
            915                 920                 925

Asp Gly Ser Phe Ala Trp Ser Trp Arg Val Lys His Gly Gln Leu Glu
    930                 935                 940

Asn Arg Pro
945

<210> SEQ ID NO 8
<211> LENGTH: 30
<212> TYPE: DNA
<213> ORGANISM: Artificial
<220> FEATURE:
<223> OTHER INFORMATION: oligonucleotide PCR primer

<400> SEQUENCE: 8
caggatcctc atggctgcag ctagcgtgac                                          30

<210> SEQ ID NO 9
<211> LENGTH: 32
<212> TYPE: DNA
<213> ORGANISM: Artificial
<220> FEATURE:
<223> OTHER INFORMATION: oligonucleotide PCR primer

<400> SEQUENCE: 9
ggtcgactta gagccctgtc aggtccacaa tg                                       32

<210> SEQ ID NO 10
<211> LENGTH: 24
<212> TYPE: DNA
<213> ORGANISM: Artificial
<220> FEATURE:
<223> OTHER INFORMATION: oligonucleotide probe

<400> SEQUENCE: 10
gatgccattg gggatttcct cttt                                                24

<210> SEQ ID NO 11
<211> LENGTH: 24
<212> TYPE: DNA
<213> ORGANISM: Artificial
<220> FEATURE:
<223> OTHER INFORMATION: oligonucleotide probe

<400> SEQUENCE: 11
cagtaaagag gaaatcccca atgg                                                24

<210> SEQ ID NO 12
<211> LENGTH: 467
<212> TYPE: PRT
<213> ORGANISM: Homo sapiens

<400> SEQUENCE: 12

Met Glu Tyr Met Ser Thr Gly Ser Asp Glu Lys Glu Glu Ile Asp Leu
1               5                   10                  15

Leu Ile Asn His Leu Asn Val Ser Glu Val Leu Asp Ile Met Glu Asn
            20                  25                  30

Leu Tyr Ala Ser Glu Glu Pro Ala Val Tyr Glu Pro Ser Leu Met Thr
        35                  40                  45

Met Cys Pro Asp Ser Asn Gln Asn Lys Glu His Ser Glu Ser Leu Leu
    50                  55                  60

Arg Ser Gly Gln Glu Val Pro Trp Leu Ser Ser Val Arg Tyr Gly Thr
```

```
            65                  70                  75                  80
Val Glu Asp Leu Leu Ala Phe Ala Asn His Ile Ser Asn Thr Thr Lys
                85                  90                  95

His Phe Tyr Arg Cys Arg Pro Gln Glu Ser Gly Ile Leu Leu Asn Met
                100                 105                 110

Val Ile Ser Pro Gln Asn Gly Arg Tyr Gln Ile Asp Ser Asp Val Leu
                115                 120                 125

Leu Val Pro Trp Lys Leu Thr Tyr Arg Ser Ile Gly Ser Gly Phe Val
        130                 135                 140

Pro Arg Gly Ala Phe Gly Lys Val Tyr Leu Ala Gln Asp Met Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
                180                 185                 190

Leu Tyr Gly Ala Val Leu Trp Gly Asp Thr Val His Leu Phe Met Glu
            195                 200                 205

Ala Gly Glu Gly Gly Ser Val Leu Glu Lys Leu Glu Ser Cys Gly Pro
        210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
                260                 265                 270

Leu Ser Val Gln Met Thr Glu Asp Val Tyr Leu Pro Lys Asp Leu Arg
            275                 280                 285

Gly Thr Glu Ile Tyr Met Ser Pro Glu Val Ile Leu Cys Arg Gly His
        290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
                340                 345                 350

Ile Ala Gly Asp Cys Ser Pro Gly Met Arg Glu Leu Ile Glu Ala Ala
            355                 360                 365

Leu Glu Arg Asn Pro Asn His Arg Pro Lys Ala Ala Asp Leu Leu Lys
        370                 375                 380

His Glu Ala Leu Asn Pro Pro Arg Glu Asp Gln Pro Arg Cys Gln Ser
385                 390                 395                 400

Leu Asp Ser Ala Leu Phe Asp Arg Lys Arg Leu Leu Ser Arg Lys Glu
                405                 410                 415

Leu Glu Leu Pro Glu Asn Ile Ala Asp Ser Ser Cys Thr Gly Ser Thr
                420                 425                 430

Glu Glu Ser Glu Val Leu Arg Arg Gln Arg Ser Leu Tyr Ile Asp Leu
            435                 440                 445

Gly Ala Leu Ala Gly Tyr Phe Asn Ile Val Arg Gly Pro Pro Thr Leu
        450                 455                 460

Glu Tyr Gly
465

<210> SEQ ID NO 13
<211> LENGTH: 467
```

-continued

<212> TYPE: PRT
<213> ORGANISM: Homo sapiens

<400> SEQUENCE: 13

```
Met Glu Tyr Met Ser Thr Gly Ser Asp Asn Lys Glu Ile Asp Leu
1               5                   10                  15

Leu Ile Lys His Leu Asn Val Ser Asp Val Ile Asp Ile Met Glu Asn
                20                  25                  30

Leu Tyr Ala Ser Glu Pro Ala Val Tyr Glu Pro Ser Leu Met Thr
            35                  40                  45

Met Cys Gln Asp Ser Asn Gln Asn Asp Glu Arg Ser Lys Ser Leu Leu
50                  55                  60

Leu Ser Gly Gln Glu Val Pro Trp Leu Ser Ser Val Arg Tyr Gly Thr
65                  70                  75                  80

Val Glu Asp Leu Leu Ala Phe Ala Asn His Ile Ser Asn Thr Ala Lys
                85                  90                  95

His Phe Tyr Gly Gln Arg Pro Gln Glu Ser Gly Ile Leu Leu Asn Met
            100                 105                 110

Val Ile Thr Pro Gln Asn Gly Arg Tyr Gln Ile Asp Ser Asp Val Leu
        115                 120                 125

Leu Ile Pro Trp Lys Leu Thr Tyr Arg Asn Ile Gly Ser Asp Phe Ile
130                 135                 140

Pro Arg Gly Ala Phe Gly Lys Val Tyr Leu Ala Gln Asp Ile Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
            180                 185                 190

Leu Tyr Gly Ala Val Leu Trp Gly Glu Thr Val His Leu Phe Met Glu
        195                 200                 205

Ala Gly Glu Gly Gly Ser Val Leu Glu Lys Leu Glu Ser Cys Gly Pro
210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
            260                 265                 270

Leu Ser Val Gln Met Thr Glu Asp Val Tyr Pro Phe Lys Asp Leu Arg
        275                 280                 285

Gly Thr Glu Ile Tyr Met Ser Pro Glu Val Ile Leu Cys Arg Gly His
290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
            340                 345                 350

Ile Ala Asp Asp Cys Ser Pro Gly Met Arg Glu Leu Ile Glu Ala Ser
        355                 360                 365

Leu Glu Arg Asn Pro Asn His Arg Pro Arg Ala Ala Asp Leu Leu Lys
370                 375                 380

His Glu Ala Leu Asn Pro Pro Arg Glu Asp Gln Pro Arg Cys Gln Ser
385                 390                 395                 400
```

```
Leu Asp Ser Ala Leu Leu Glu Arg Lys Arg Leu Leu Ser Arg Lys Glu
                405                 410                 415
Leu Glu Leu Pro Glu Asn Ile Ala Asp Ser Ser Cys Thr Gly Ser Thr
            420                 425                 430
Glu Glu Ser Glu Met Leu Lys Arg Gln Arg Ser Leu Tyr Ile Asp Leu
        435                 440                 445
Gly Ala Leu Ala Gly Tyr Phe Asn Leu Val Arg Gly Pro Pro Thr Leu
    450                 455                 460
Glu Tyr Gly
465

<210> SEQ ID NO 14
<211> LENGTH: 947
<212> TYPE: PRT
<213> ORGANISM: Homo sapiens

<400> SEQUENCE: 14

Met Ala Val Met Glu Met Ala Cys Pro Gly Ala Pro Gly Ser Ala Val
1               5                   10                  15
Gly Gln Gln Lys Glu Leu Pro Lys Pro Lys Glu Lys Thr Pro Pro Leu
            20                  25                  30
Gly Lys Lys Gln Ser Ser Val Tyr Lys Leu Glu Ala Val Glu Lys Ser
        35                  40                  45
Pro Val Phe Cys Gly Lys Trp Glu Ile Leu Asn Asp Val Ile Thr Lys
    50                  55                  60
Gly Thr Ala Lys Glu Gly Ser Glu Ala Gly Pro Ala Ala Ile Ser Ile
65                  70                  75                  80
Ile Ala Gln Ala Glu Cys Glu Asn Ser Gln Glu Phe Ser Pro Thr Phe
                85                  90                  95
Ser Glu Arg Ile Phe Ile Ala Gly Ser Lys Gln Tyr Ser Gln Ser Glu
            100                 105                 110
Ser Leu Asp Gln Ile Pro Asn Asn Val Ala His Ala Thr Glu Gly Lys
        115                 120                 125
Met Ala Arg Val Cys Trp Lys Gly Lys Arg Arg Ser Lys Ala Arg Lys
    130                 135                 140
Lys Arg Lys Lys Lys Ser Ser Lys Ser Leu Ala His Ala Gly Val Ala
145                 150                 155                 160
Leu Ala Lys Pro Leu Pro Arg Thr Pro Glu Gln Glu Ser Cys Thr Ile
                165                 170                 175
Pro Val Gln Glu Asp Glu Ser Pro Leu Gly Ala Pro Tyr Val Arg Asn
            180                 185                 190
Thr Pro Gln Phe Thr Lys Pro Leu Lys Glu Pro Gly Leu Gly Gln Leu
        195                 200                 205
Cys Phe Lys Gln Leu Gly Glu Gly Leu Arg Pro Ala Leu Pro Arg Ser
    210                 215                 220
Glu Leu His Lys Leu Ile Ser Pro Leu Gln Cys Leu Asn His Val Trp
225                 230                 235                 240
Lys Leu His His Pro Gln Asp Gly Gly Pro Leu Pro Leu Pro Thr His
                245                 250                 255
Pro Phe Pro Tyr Ser Arg Leu Pro His Pro Phe Pro Phe His Pro Leu
            260                 265                 270
Gln Pro Trp Lys Pro His Pro Leu Glu Ser Phe Leu Gly Lys Leu Ala
        275                 280                 285
Cys Val Asp Ser Gln Lys Pro Leu Pro Asp Pro His Leu Ser Lys Leu
    290                 295                 300
```

```
Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gln Ala His Ser
            340                 345                 350

Leu Thr Ser Leu Ala Lys Thr Trp Ala Ala Arg Gly Ser Arg Ser Arg
            355                 360                 365

Glu Pro Ser Pro Lys Thr Glu Asp Asn Glu Gly Val Leu Leu Thr Glu
370                 375                 380

Lys Leu Lys Pro Val Asp Tyr Glu Tyr Arg Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
            420                 425                 430

Leu Glu Val Phe Arg Ala Glu Glu Leu Met Ala Cys Ala Gly Leu Thr
            435                 440                 445

Ser Pro Arg Ile Val Pro Leu Tyr Gly Ala Val Arg Glu Gly Pro Trp
450                 455                 460

Val Asn Ile Phe Met Glu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
            515                 520                 525

His Ala Ala Leu Cys Asp Phe Gly His Ala Val Cys Leu Gln Pro Asp
            530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
            580                 585                 590

Cys His Pro Trp Thr Gln Phe Phe Arg Gly Pro Leu Cys Leu Lys Ile
            595                 600                 605

Ala Ser Glu Pro Pro Val Arg Glu Ile Pro Ser Cys Ala Pro
610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
            660                 665                 670

Arg His Pro Pro Asn Gln Ala Asn Tyr His Gln Thr Leu His Ala
            675                 680                 685

Gln Pro Arg Glu Leu Ser Pro Arg Ala Pro Gly Pro Arg Pro Ala Glu
            690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                725                 730                 735
```

Ser Gly Met Trp Glu Pro Leu Pro Leu Ser Ser Leu Glu Pro Ala Pro
                740                 745                 750

Ala Arg Asn Pro Ser Ser Pro Glu Arg Lys Ala Thr Val Pro Glu Gln
            755                 760                 765

Glu Leu Gln Gln Leu Glu Ile Glu Leu Phe Leu Asn Ser Leu Ser Gln
    770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Trp Asn Met Val Leu Ala Arg
    835                 840                 845

Gly Arg Pro Thr Asp Thr Pro Ser Tyr Phe Asn Gly Val Lys Val Gln
850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
            900                 905                 910

Met Glu Val Pro Asp Ser Gly Ile Asp Leu Gln Cys Thr Leu Ala Pro
    915                 920                 925

Asp Gly Ser Phe Ala Trp Ser Trp Arg Val Lys His Gly Gln Leu Glu
930                 935                 940

Asn Arg Pro
945

<210> SEQ ID NO 15
<211> LENGTH: 688
<212> TYPE: PRT
<213> ORGANISM: Homo sapiens

<400> SEQUENCE: 15

Thr Leu Thr His Thr Thr Ser Leu Phe Ala Pro Pro Asn Leu Ser Pro
1               5                   10                  15

Met Gln Asp Phe Ile Gly Ser Val Arg Arg Ser Leu Val Phe Lys Gln
            20                  25                  30

Ser Gly Asp Phe Asp Thr Gly Ala Ala Gly Val Gly Ser Gly Phe Gly
        35                  40                  45

Gly Phe Val Glu Lys Leu Gly Ser Ser Ile Arg Lys Ser Ser Ile Gly
    50                  55                  60

Ile Phe Ser Lys Ala His Val Pro Ala Leu Pro Ser Ile Ser Lys Ala
65                  70                  75                  80

Glu Leu Pro Ala Lys Ala Arg Lys Asp Asp Thr Pro Pro Ile Arg Trp
                85                  90                  95

Arg Lys Gly Glu Met Ile Gly Cys Gly Ala Phe Gly Arg Val Tyr Met
            100                 105                 110

Gly Met Asn Val Asp Ser Gly Glu Leu Leu Ala Ile Lys Glu Val Ser
        115                 120                 125

Ile Ala Met Asn Gly Ala Ser Arg Glu Arg Ala Gln Ala His Val Arg
    130                 135                 140

Glu Leu Glu Glu Glu Val Asn Leu Leu Lys Asn Leu Ser His Pro Asn
145                 150                 155                 160

```
Ile Val Arg Tyr Leu Gly Thr Ala Arg Glu Ala Gly Ser Leu Asn Ile
                165                 170                 175

Leu Leu Glu Phe Val Pro Gly Ser Ile Ser Ser Leu Leu Gly Lys
            180                 185                 190

Phe Gly Ser Phe Pro Glu Ser Val Ile Arg Met Tyr Thr Lys Gln Leu
            195                 200                 205

Leu Leu Gly Leu Glu Tyr Leu His Lys Asn Gly Ile Met His Arg Asp
210                 215                 220

Ile Lys Gly Ala Asn Ile Leu Val Asp Asn Lys Gly Cys Ile Lys Leu
225                 230                 235                 240

Ala Asp Phe Gly Ala Ser Lys Lys Val Val Glu Leu Ala Thr Met Thr
                245                 250                 255

Gly Ala Lys Ser Met Lys Gly Thr Pro Tyr Trp Met Ala Pro Glu Val
            260                 265                 270

Ile Leu Gln Thr Gly His Ser Phe Ser Ala Asp Ile Trp Ser Val Gly
            275                 280                 285

Cys Thr Ile Ile Glu Met Ala Thr Gly Lys Pro Pro Trp Ser Gln Gln
290                 295                 300

Tyr Gln Glu Val Ala Ala Leu Phe His Ile Gly Thr Thr Lys Ser His
305                 310                 315                 320

Pro Pro Ile Pro Glu His Leu Ser Ala Glu Ser Lys Asp Phe Leu Leu
                325                 330                 335

Lys Cys Leu Gln Lys Glu Pro His Leu Arg His Ser Ala Ser Asn Leu
            340                 345                 350

Leu Gln His Pro Phe Val Thr Ala Glu His Gln Glu Ala Arg Pro Phe
            355                 360                 365

Leu Arg Ser Ser Phe Met Gly Asn Pro Glu Asn Met Ala Ala Gln Arg
370                 375                 380

Met Asp Val Arg Thr Ser Ile Ile Pro Asp Met Arg Ala Ser Cys Asn
385                 390                 395                 400

Gly Leu Lys Asp Val Cys Gly Val Ser Ala Val Arg Cys Ser Thr Val
                405                 410                 415

Tyr Pro Glu Asn Ser Leu Gly Lys Glu Ser Leu Trp Lys Leu Gly Asn
            420                 425                 430

Ser Asp Asp Met Cys Gln Met Asp Asn Asp Phe Met Phe Gly
            435                 440                 445

Ala Ser Val Lys Cys Ser Ser Asp Leu His Ser Pro Ala Asn Tyr Lys
450                 455                 460

Ser Phe Asn Pro Met Cys Glu Pro Asp Asn Asp Trp Pro Cys Lys Phe
465                 470                 475                 480

Asp Glu Ser Pro Glu Leu Thr Lys Ser Gln Ala Asn Leu His Tyr Asp
                485                 490                 495

Gln Ala Thr Ile Lys Pro Thr Asn Asn Pro Ile Met Ser Tyr Lys Glu
            500                 505                 510

Asp Leu Ala Phe Thr Phe Pro Ser Gly Gln Ser Ala Ala Glu Asp Asp
            515                 520                 525

Asp Glu Leu Thr Glu Ser Lys Ile Arg Ala Phe Leu Asp Glu Lys Ala
530                 535                 540

Met Asp Leu Lys Lys Leu Gln Thr Pro Leu Tyr Glu Gly Phe Tyr Asn
545                 550                 555                 560

Ser Leu Asn Val Ser Ser Thr Pro Ser Pro Val Gly Thr Gly Asn Lys
                565                 570                 575

Glu Asn Val Pro Ser Asn Ile Asn Leu Pro Pro Lys Ser Arg Ser Pro
```

```
                    580                 585                 590
Lys Arg Met Leu Ser Arg Arg Leu Ser Thr Ala Ile Glu Gly Ala Cys
                595                 600                 605

Ala Pro Ser Pro Val Thr His Ser Lys Arg Ile Ser Asn Ile Gly Gly
            610                 615                 620

Leu Asn Gly Glu Ala Ile Gln Glu Ala Gln Leu Pro Arg His Asn Glu
625                 630                 635                 640

Trp Lys Asp Leu Leu Gly Ser Gln Arg Glu Ala Val Asn Ser Ser Phe
                645                 650                 655

Ser Glu Arg Gln Arg Arg Trp Lys Glu Glu Leu Asp Glu Glu Leu Gln
            660                 665                 670

Arg Lys Arg Glu Ile Met Arg Gln Ala Val Asn Leu Ser Pro Pro Lys
        675                 680                 685

<210> SEQ ID NO 16
<211> LENGTH: 659
<212> TYPE: PRT
<213> ORGANISM: Homo sapiens

<400> SEQUENCE: 16

Met Glu Tyr Tyr Thr Ser Lys Glu Val Ala Glu Trp Leu Lys Ser Ile
1               5                   10                  15

Gly Leu Glu Lys Tyr Ile Glu Gln Phe Ser Gln Asn Asn Ile Glu Gly
            20                  25                  30

Arg His Leu Asn His Leu Thr Leu Pro Leu Leu Lys Asp Leu Gly Ile
        35                  40                  45

Glu Asn Thr Ala Lys Gly Lys Gln Phe Leu Lys Gln Arg Asp Tyr Leu
    50                  55                  60

Arg Glu Phe Pro Arg Pro Cys Ile Leu Arg Phe Ile Ala Cys Asn Gly
65                  70                  75                  80

Gln Thr Arg Ala Val Gln Ser Arg Gly Asp Tyr Gln Lys Thr Leu Ala
                85                  90                  95

Ile Ala Leu Lys Lys Phe Ser Leu Glu Asp Ala Ser Lys Phe Ile Val
            100                 105                 110

Cys Val Ser Gln Ser Ser Arg Ile Lys Leu Ile Thr Glu Glu Phe
        115                 120                 125

Lys Gln Ile Cys Phe Asn Ser Ser Pro Glu Arg Asp Arg Leu Ile
    130                 135                 140

Ile Val Pro Lys Glu Lys Pro Cys Pro Ser Phe Glu Asp Leu Arg Arg
145                 150                 155                 160

Ser Trp Glu Ile Glu Leu Ala Gln Pro Ala Ala Leu Ser Ser Gln Ser
                165                 170                 175

Ser Leu Ser Pro Lys Leu Ser Ser Val Leu Pro Thr Ser Thr Gln Lys
            180                 185                 190

Arg Ser Val Arg Ser Asn Asn Ala Lys Pro Phe Glu Ser Tyr Gln Arg
        195                 200                 205

Pro Pro Ser Glu Leu Ile Asn Ser Arg Ile Ser Asp Phe Phe Pro Asp
    210                 215                 220

His Gln Pro Lys Leu Leu Glu Lys Thr Ile Ser Asn Ser Leu Arg Arg
225                 230                 235                 240

Asn Leu Ser Ile Arg Thr Ser Gln Gly His Asn Leu Gly Asn Phe Gly
                245                 250                 255

Gln Glu Ile Leu Pro Arg Ser Arg Arg Ala Arg Pro Ser Glu Leu
            260                 265                 270

Val Cys Pro Leu Ser Ser Leu Arg Ile Ser Val Ala Glu Asp Val Asn
```

```
                    275                 280                 285
Arg Leu Pro Arg Ile Asp Arg Gly Phe Asp Pro Pro Leu Thr Val Ser
290                 295                 300

Ser Thr Gln Arg Ile Ser Arg Pro Pro Ser Leu Gln Lys Ser Ile Thr
305                 310                 315                 320

Met Val Gly Val Glu Pro Leu Tyr Gln Ser Asn Gly Asn Glu Lys Ser
                325                 330                 335

Ser Lys Tyr Asn Val Phe Ser Glu Ser Ala His Gly Asn His Gln Val
                340                 345                 350

Leu Ser Phe Ser Pro Gly Ser Ser Pro Ser Phe Ile Glu Gln Pro Ser
            355                 360                 365

Pro Ile Ser Pro Thr Ser Thr Thr Ser Glu Asp Thr Asn Thr Leu Glu
        370                 375                 380

Glu Asp Thr Asp Asp Gln Ser Ile Lys Trp Ile Arg Gly Ala Leu Ile
385                 390                 395                 400

Gly Ser Gly Ser Phe Gly Gln Val Tyr Leu Gly Met Asn Ala Ser Ser
                405                 410                 415

Gly Glu Leu Met Ala Val Lys Gln Val Ile Leu Asp Ser Val Ser Glu
            420                 425                 430

Ser Lys Asp Arg His Ala Lys Leu Leu Asp Ala Leu Ala Gly Glu Ile
        435                 440                 445

Ala Leu Leu Gln Glu Leu Ser His Glu His Ile Val Gln Tyr Leu Gly
    450                 455                 460

Ser Asn Leu Asn Ser Asp His Leu Asn Ile Phe Leu Glu Tyr Val Pro
465                 470                 475                 480

Gly Gly Ser Val Ala Gly Leu Leu Thr Met Tyr Gly Ser Phe Glu Glu
                485                 490                 495

Thr Leu Val Lys Asn Phe Ile Lys Gln Thr Leu Lys Gly Leu Glu Tyr
            500                 505                 510

Leu His Ser Arg Gly Ile Val His Arg Asp Ile Lys Gly Ala Asn Ile
        515                 520                 525

Leu Val Asp Asn Lys Gly Lys Ile Lys Ile Ser Asp Phe Gly Ile Ser
    530                 535                 540

Lys Lys Leu Glu Leu Asn Ser Thr Ser Thr Lys Thr Gly Gly Ala Arg
545                 550                 555                 560

Pro Ser Phe Gln Gly Ser Ser Phe Trp Met Ala Pro Glu Val Val Lys
                565                 570                 575

Gln Thr Met His Thr Glu Lys Thr Asp Ile Trp Ser Leu Gly Cys Leu
            580                 585                 590

Val Ile Glu Met Leu Thr Ser Lys His Pro Tyr Pro Asn Cys Asp Gln
        595                 600                 605

Met Gln Ala Ile Phe Arg Ile Gly Glu Asn Ile Leu Pro Glu Phe Pro
    610                 615                 620

Ser Asn Ile Ser Ser Ala Ile Asp Phe Leu Glu Lys Thr Phe Ala
625                 630                 635                 640

Ile Asp Cys Asn Leu Arg Pro Thr Ala Ser Glu Leu Leu Ser His Pro
                645                 650                 655

Phe Val Ser

<210> SEQ ID NO 17
<211> LENGTH: 717
<212> TYPE: PRT
<213> ORGANISM: Homo sapiens

<400> SEQUENCE: 17
```

```
Met Glu Gln Thr Gln Thr Ala Glu Gly Thr Asp Leu Leu Ile Gly Asp
1               5                   10                  15

Glu Lys Thr Asn Asp Leu Pro Phe Val Gln Leu Phe Leu Glu Glu Ile
            20                  25                  30

Gly Cys Thr Gln Tyr Leu Asp Ser Phe Ile Gln Cys Asn Leu Val Thr
        35                  40                  45

Glu Glu Glu Ile Lys Tyr Leu Asp Lys Asp Ile Leu Ile Ala Leu Gly
50                  55                  60

Val Asn Lys Ile Gly Asp Arg Leu Lys Ile Leu Arg Lys Ser Lys Ser
65                  70                  75                  80

Phe Gln Arg Asp Lys Arg Ile Glu Gln Val Asn Arg Leu Lys Asn Leu
                85                  90                  95

Met Glu Lys Val Ser Ser Leu Ser Thr Ala Thr Leu Ser Met Asn Ser
                100                 105                 110

Glu Leu Ile Pro Glu Lys His Cys Val Ile Phe Ile Leu Asn Asp Gly
            115                 120                 125

Ser Ala Lys Lys Val Asn Val Asn Gly Cys Phe Asn Ala Asp Ser Ile
        130                 135                 140

Lys Lys Arg Leu Ile Arg Arg Leu Pro His Glu Leu Leu Ala Thr Asn
145                 150                 155                 160

Ser Asn Gly Glu Val Thr Lys Met Val Gln Asp Tyr Asp Val Phe Val
                165                 170                 175

Leu Asp Tyr Thr Lys Asn Val Leu His Leu Leu Tyr Asp Val Glu Leu
                180                 185                 190

Val Thr Ile Cys His Ala Asn Asp Arg Val Glu Lys Asn Arg Leu Ile
        195                 200                 205

Phe Val Ser Lys Asp Gln Thr Pro Ser Asp Lys Ala Ile Ser Thr Ser
210                 215                 220

Lys Lys Leu Tyr Leu Arg Thr Leu Ser Ala Leu Ser Gln Val Gly Pro
225                 230                 235                 240

Ser Ser Ser Asn Leu Leu Ala Gln Asn Lys Gly Ile Ser His Asn Asn
                245                 250                 255

Ala Glu Gly Lys Leu Arg Ile Asp Asn Thr Glu Lys Asp Arg Ile Arg
                260                 265                 270

Gln Ile Phe Asn Gln Arg Pro Pro Ser Glu Phe Ile Ser Thr Asn Leu
            275                 280                 285

Ala Gly Tyr Phe Pro His Thr Asp Met Lys Arg Leu Gln Lys Thr Met
        290                 295                 300

Arg Glu Ser Phe Arg His Ser Ala Arg Leu Ser Ile Ala Gln Arg Arg
305                 310                 315                 320

Pro Leu Ser Ala Glu Ser Asn Asn Ile Gly Asp Ile Leu Leu Lys His
                325                 330                 335

Ser Asn Ala Val Asp Met Ala Leu Leu Gln Gly Leu Asp Gln Thr Arg
                340                 345                 350

Leu Ser Ser Lys Leu Asp Thr Thr Lys Ile Pro Lys Leu Ala His Lys
            355                 360                 365

Arg Pro Glu Asp Asn Asp Ala Ile Ser Asn Gln Leu Glu Leu Leu Ser
        370                 375                 380

Val Glu Ser Gly Glu Glu Glu Asp His Asp Phe Phe Gly Glu Asp Ser
385                 390                 395                 400

Asp Ile Val Ser Leu Pro Thr Lys Ile Ala Thr Pro Lys Asn Trp Leu
                405                 410                 415

Lys Gly Ala Cys Ile Gly Ser Gly Ser Phe Gly Ser Val Tyr Leu Gly
```

```
                     420                 425                 430
Met Asn Ala His Thr Gly Glu Leu Met Ala Val Lys Gln Val Glu Ile
                435                 440                 445
Lys Asn Asn Asn Ile Gly Val Pro Thr Asp Asn Asn Lys Gln Ala Asn
            450                 455                 460
Ser Asp Glu Asn Asn Glu Gln Glu Gln Gln Lys Ile Glu Asp
465                 470                 475                 480
Val Gly Ala Val Ser His Pro Lys Thr Asn Gln Asn Ile His Arg Lys
                485                 490                 495
Met Val Asp Ala Leu Gln His Glu Met Asn Leu Leu Lys Glu Leu His
            500                 505                 510
His Glu Asn Ile Val Thr Tyr Tyr Gly Ala Ser Gln Glu Gly Gly Asn
                515                 520                 525
Leu Asn Ile Phe Leu Glu Tyr Val Pro Gly Gly Ser Val Ser Ser Met
            530                 535                 540
Leu Asn Asn Tyr Gly Pro Phe Glu Glu Ser Leu Ile Thr Asn Phe Thr
545                 550                 555                 560
Arg Gln Ile Leu Ile Gly Val Ala Tyr Leu His Lys Lys Asn Ile Ile
                565                 570                 575
His Arg Asp Ile Lys Gly Ala Asn Ile Leu Ile Asp Ile Lys Gly Cys
            580                 585                 590
Val Lys Ile Thr Asp Phe Gly Ile Ser Lys Lys Leu Ser Pro Leu Asn
                595                 600                 605
Lys Lys Gln Asn Lys Arg Ala Ser Leu Gln Gly Ser Val Phe Trp Met
            610                 615                 620
Ser Pro Glu Val Val Lys Gln Thr Ala Thr Ala Lys Ala Asp Ile
625                 630                 635                 640
Trp Ser Thr Gly Cys Val Val Ile Glu Met Phe Thr Gly Lys His Pro
                645                 650                 655
Phe Pro Asp Phe Ser Gln Met Gln Ala Ile Phe Lys Ile Gly Thr Asn
            660                 665                 670
Thr Thr Pro Glu Ile Pro Ser Trp Ala Thr Ser Glu Gly Lys Asn Phe
            675                 680                 685
Leu Arg Lys Ala Phe Glu Leu Asp Tyr Gln Tyr Arg Pro Ser Ala Leu
            690                 695                 700
Glu Leu Leu Gln His Pro Trp Leu Asp Ala His Ile Ile
705                 710                 715

<210> SEQ ID NO 18
<211> LENGTH: 1478
<212> TYPE: PRT
<213> ORGANISM: Homo sapiens

<400> SEQUENCE: 18

Met Pro Phe Leu Arg Lys Ile Ala Gly Thr Ala His Thr His Ser Arg
1               5                   10                  15
Ser Asp Ser Asn Ser Ser Val Lys Phe Gly His Gln Pro Thr Ser Ser
                20                  25                  30
Val Ala Ser Thr Lys Ser Ser Lys Ser Pro Arg Ala Thr Ser Arg
            35                  40                  45
Lys Ser Ile Tyr Asp Asp Ile Arg Ser Gln Phe Pro Asn Leu Thr Pro
            50                  55                  60
Asn Ser Thr Ser Ser Gln Phe Tyr Glu Ser Thr Pro Val Ile Glu Gln
65                  70                  75                  80
Ser Phe Asn Trp Thr Thr Asp Asp His Ile Ser Ala Gly Thr Leu Glu
```

```
                 85                  90                  95
Asn Pro Thr Ser Glu Thr Asn Ser Ser Tyr Lys Asn Asp Asn Gly Pro
                100                 105                 110

Ser Ser Leu Ser Asp Ser Arg Lys Ser Gly Gly Asn Ser Val Asn
            115                 120                 125

Ser Leu Ser Phe Asp Lys Leu Ile Leu Ser Trp Asp Pro Thr Asp Pro
130                 135                 140

Asp Glu Trp Thr Met His Arg Val Thr Ser Trp Phe Lys Phe His Asp
145                 150                 155                 160

Phe Pro Glu Ser Trp Ile Leu Phe Phe Lys Lys His Gln Leu Phe Gly
                165                 170                 175

His Arg Phe Ile Lys Leu Leu Ala Tyr Asp Asn Phe Ala Val Tyr Glu
                180                 185                 190

Lys Tyr Leu Pro Gln Thr Lys Thr Ala Ser Tyr Thr Arg Phe Gln Gln
                195                 200                 205

Leu Leu Lys Lys Thr Met Thr Lys Asn Val Thr Asn Ser His Ile Arg
            210                 215                 220

Gln Lys Ser Ala Ser Lys Leu Lys Ser Ser Arg Ser Ser Ser Glu Ser
225                 230                 235                 240

Ile Lys Ser Lys Leu Lys Asn Ser Lys Ser Gln Glu Asp Ile Ser Asn
                245                 250                 255

Ser Arg Ser Thr Ser Glu Ser Ala Leu Ser Pro Thr Lys Ser Gly Pro
            260                 265                 270

Ser Lys Thr Asp Glu Lys Asn Phe Leu His Ser Thr Ser Thr His Gln
            275                 280                 285

Lys Thr Lys Ser Ala Ser Ser Leu Tyr Arg Arg Ser Phe Ile Ser Leu
290                 295                 300

Arg Gly Ser Ser Ser Asn Ala Ser Ser Ala Lys Ser Pro Ser Asn
305                 310                 315                 320

Ile Lys Leu Ser Ile Pro Ala Arg Pro His Ser Ile Ile Glu Ser Asn
                325                 330                 335

Ser Thr Leu Thr Lys Ser Ala Ser Pro Pro Ala Ser Pro Ser Tyr Pro
            340                 345                 350

Ser Ile Phe Arg Arg His His Lys Ser Ser Ser Glu Ser Ser Leu
            355                 360                 365

Ile Asn Ser Leu Phe Gly Ser Gly Ile Gly Glu Glu Ala Pro Thr Lys
            370                 375                 380

Pro Asn Pro Gln Gly His Ser Leu Ser Ser Glu Asn Leu Ala Lys Gly
385                 390                 395                 400

Lys Ser Lys His Tyr Glu Thr Asn Val Ser Ser Pro Leu Lys Gln Ser
                405                 410                 415

Ser Leu Pro Thr Ser Asp Asp Lys Gly Asn Leu Trp Asn Lys Phe Lys
            420                 425                 430

Arg Lys Ser Gln Ile Gly Val Pro Ser Pro Asn Thr Val Ala Tyr Val
            435                 440                 445

Thr Ser Gln Glu Thr Pro Ser Leu Lys Ser Asn Ser Ser Thr Ala Thr
450                 455                 460

Leu Thr Val Gln Thr Ala Asp Val Asn Ile Pro Ser Pro Ser Ser Ser
465                 470                 475                 480

Pro Pro Pro Ile Pro Lys Thr Ala Asn Arg Ser Leu Glu Val Ile Ser
                485                 490                 495

Thr Glu Asp Thr Pro Lys Ile Ser Ser Thr Thr Ala Ser Phe Lys Glu
            500                 505                 510
```

```
Thr Tyr Pro Asp Cys Ile Asn Pro Asp Lys Thr Val Pro Val
        515                 520                 525

Asn Asn Gln Lys Tyr Ser Val Lys Asn Phe Leu Leu Asp Gln Lys Phe
        530                 535                 540

Tyr Pro Leu Lys Lys Thr Gly Leu Asn Asp Ser Glu Asn Lys Tyr Ile
545                 550                 555                 560

Leu Val Thr Lys Asp Asn Val Ser Phe Val Pro Leu Asn Leu Lys Ser
                565                 570                 575

Val Ala Lys Leu Ser Ser Phe Lys Glu Ser Ala Leu Thr Lys Leu Gly
                580                 585                 590

Ile Asn His Lys Asn Val Thr Phe His Met Thr Asp Phe Asp Cys Asp
                595                 600                 605

Ile Gly Ala Ala Ile Pro Asp Asp Thr Leu Glu Phe Leu Lys Lys Ser
        610                 615                 620

Leu Phe Leu Asn Thr Ser Gly Lys Ile Tyr Ile Lys Asp Gln Met Lys
625                 630                 635                 640

Leu Gln Gln Lys Pro Lys Pro Ala Pro Leu Thr Ser Glu Asn Asn Val
                645                 650                 655

Pro Leu Lys Ser Val Lys Ser Lys Ser Ser Met Arg Ser Gly Thr Ser
                660                 665                 670

Ser Leu Ile Ala Ser Thr Asp Asp Val Ser Ile Val Thr Ser Ser Ser
                675                 680                 685

Asp Ile Thr Ser Phe Asp Glu His Ala Ser Gly Ser Gly Arg Arg Tyr
        690                 695                 700

Pro Gln Thr Pro Ser Tyr Tyr Tyr Asp Arg Val Ser Asn Thr Asn Pro
705                 710                 715                 720

Thr Glu Glu Leu Asn Tyr Trp Asn Ile Lys Glu Val Leu Ser His Glu
                725                 730                 735

Glu Asn Ala Pro Lys Met Val Phe Lys Thr Ser Pro Lys Leu Glu Leu
                740                 745                 750

Asn Ile Pro Asp Lys Gly Ser Lys Leu Asn Ile Pro Thr Pro Ile Thr
        755                 760                 765

Glu Asn Glu Ser Lys Ser Ser Phe Gln Val Leu Arg Lys Asp Glu Gly
        770                 775                 780

Thr Glu Ile Asp Phe Asn His Arg Arg Glu Ser Pro Tyr Thr Lys Pro
785                 790                 795                 800

Glu Leu Ala Pro Lys Arg Glu Ala Pro Lys Pro Pro Ala Asn Thr Ser
                805                 810                 815

Pro Gln Arg Thr Leu Ser Thr Ser Lys Gln Asn Lys Pro Ile Arg Leu
                820                 825                 830

Val Arg Ala Ser Thr Lys Ile Ser Arg Ser Lys Arg Ser Lys Pro Leu
                835                 840                 845

Pro Pro Gln Leu Leu Ser Ser Pro Ile Glu Ala Ser Ser Ser Ser Pro
        850                 855                 860

Asp Ser Leu Thr Ser Ser Tyr Thr Pro Ala Ser Thr His Val Leu Ile
865                 870                 875                 880

Pro Gln Pro Tyr Lys Gly Ala Asn Asp Val Met Arg Arg Leu Lys Thr
                885                 890                 895

Asp Gln Asp Ser Thr Ser Thr Ser Pro Ser Leu Lys Met Lys Gln Lys
                900                 905                 910

Val Asn Arg Ser Asn Ser Thr Val Ser Thr Ser Asn Ser Ile Phe Tyr
                915                 920                 925

Ser Pro Ser Pro Leu Leu Lys Arg Gly Asn Ser Lys Arg Val Val Ser
        930                 935                 940
```

```
Ser Thr Ser Ala Ala Asp Ile Phe Glu Glu Asn Asp Ile Thr Phe Ala
945                 950                 955                 960

Asp Ala Pro Pro Met Phe Asp Ser Asp Ser Asp Asp Ser Ser
            965                 970                 975

Ser Ser Asp Ile Ile Trp Ser Lys Lys Thr Ala Pro Glu Thr
        980                 985                 990

Asn Asn Glu Asn Lys Lys Asp Glu Lys Ser Asp Asn Ser Ser Thr His
            995                 1000                1005

Ser Asp Glu Ile Phe Tyr Asp Ser Gln Thr Gln Asp Lys Met Glu
    1010                1015                1020

Arg Lys Met Thr Phe Arg Pro Ser Pro Glu Val Val Tyr Gln Asn
    1025                1030                1035

Leu Glu Lys Phe Phe Pro Arg Ala Asn Leu Asp Lys Pro Ile Thr
    1040                1045                1050

Glu Gly Ile Ala Ser Pro Thr Ser Pro Lys Ser Leu Asp Ser Leu
    1055                1060                1065

Leu Ser Pro Lys Asn Val Ala Ser Ser Arg Thr Glu Pro Ser Thr
    1070                1075                1080

Pro Ser Arg Pro Val Pro Pro Asp Ser Ser Tyr Glu Phe Ile Gln
    1085                1090                1095

Asp Gly Leu Asn Gly Lys Asn Lys Pro Leu Asn Gln Ala Lys Thr
    1100                1105                1110

Pro Lys Arg Thr Lys Thr Ile Arg Thr Ile Ala His Glu Ala Ser
    1115                1120                1125

Leu Ala Arg Lys Asn Ser Val Lys Leu Lys Arg Gln Asn Thr Lys
    1130                1135                1140

Met Trp Gly Thr Arg Met Val Glu Val Thr Glu Asn His Met Val
    1145                1150                1155

Ser Ile Asn Lys Ala Lys Asn Ser Lys Gly Glu Tyr Lys Glu Phe
    1160                1165                1170

Ala Trp Met Lys Gly Glu Met Ile Gly Lys Gly Ser Phe Gly Ala
    1175                1180                1185

Val Tyr Leu Cys Leu Asn Val Thr Thr Gly Glu Met Met Ala Val
    1190                1195                1200

Lys Gln Val Glu Val Pro Lys Tyr Ser Ser Gln Asn Glu Ala Ile
    1205                1210                1215

Leu Ser Thr Val Glu Ala Leu Arg Ser Glu Val Ser Thr Leu Lys
    1220                1225                1230

Asp Leu Asp His Leu Asn Ile Val Gln Tyr Leu Gly Phe Glu Asn
    1235                1240                1245

Lys Asn Asn Ile Tyr Ser Leu Phe Leu Glu Tyr Val Ala Gly Gly
    1250                1255                1260

Ser Val Gly Ser Leu Ile Arg Met Tyr Gly Arg Phe Asp Glu Pro
    1265                1270                1275

Leu Ile Lys His Leu Thr Thr Gln Val Leu Lys Gly Leu Ala Tyr
    1280                1285                1290

Leu His Ser Lys Gly Ile Leu His Arg Asp Met Lys Ala Asp Asn
    1295                1300                1305

Leu Leu Leu Asp Gln Asp Gly Ile Cys Lys Ile Ser Asp Phe Gly
    1310                1315                1320

Ile Ser Arg Lys Ser Lys Asp Ile Tyr Ser Asn Ser Asp Met Thr
    1325                1330                1335

Met Arg Gly Thr Val Phe Trp Met Ala Pro Glu Met Val Asp Thr
```

```
                1340                1345                1350

Lys Gln Gly Tyr Ser Ala Lys Val Asp Ile Trp Ser Leu Gly Cys
    1355                1360                1365

Ile Val Leu Glu Met Phe Ala Gly Lys Arg Pro Trp Ser Asn Leu
    1370                1375                1380

Glu Val Val Ala Ala Met Phe Lys Ile Gly Lys Ser Lys Ser Ala
    1385                1390                1395

Pro Pro Ile Pro Glu Asp Thr Leu Pro Leu Ile Ser Gln Ile Gly
    1400                1405                1410

Arg Asn Phe Leu Asp Ala Cys Phe Glu Ile Asn Pro Glu Lys Arg
    1415                1420                1425

Pro Thr Ala Asn Glu Leu Leu Ser His Pro Phe Ser Glu Val Asn
    1430                1435                1440

Glu Thr Phe Asn Phe Lys Ser Thr Arg Leu Ala Lys Phe Ile Lys
    1445                1450                1455

Ser Asn Asp Lys Leu Asn Ser Ser Lys Leu Arg Ile Thr Ser Gln
    1460                1465                1470

Glu Asn Lys Thr Glu
    1475

<210> SEQ ID NO 19
<211> LENGTH: 672
<212> TYPE: PRT
<213> ORGANISM: Mus sp.

<400> SEQUENCE: 19

Met Val Thr Ala Val Pro Ala Val Phe Ser Lys Leu Val Thr Met Leu
1               5                   10                  15

Asn Ala Ser Gly Ser Thr His Phe Thr Arg Met Arg Arg Arg Leu Met
            20                  25                  30

Ala Ile Ala Asp Glu Val Glu Ile Ala Glu Val Ile Gln Leu Gly Val
        35                  40                  45

Glu Asp Thr Val Asp Gly His Gln Asp Ser Leu Gln Ala Val Ala Pro
    50                  55                  60

Thr Ser Cys Leu Glu Asn Ser Ser Leu Glu His Thr Val His Arg Glu
65                  70                  75                  80

Lys Thr Gly Lys Gly Leu Ser Ala Thr Arg Leu Ser Ala Ser Ser Glu
                85                  90                  95

Asp Ile Ser Asp Arg Leu Ala Gly Val Ser Val Gly Leu Pro Ser Ser
            100                 105                 110

Thr Thr Thr Glu Gln Pro Lys Pro Ala Val Gln Thr Lys Gly Arg Pro
        115                 120                 125

His Ser Gln Cys Leu Asn Ser Ser Pro Leu Ser His Ala Gln Leu Met
    130                 135                 140

Phe Pro Ala Pro Ser Ala Pro Cys Ser Ser Ala Pro Ser Val Pro Asp
145                 150                 155                 160

Ile Ser Lys His Arg Pro Gln Ala Phe Val Pro Cys Lys Ile Pro Ser
                165                 170                 175

Ala Ser Pro Gln Thr Gln Arg Lys Phe Ser Leu Gln Phe Gln Arg Asn
            180                 185                 190

Cys Ser Glu His Arg Asp Ser Asp Gln Leu Ser Pro Val Phe Thr Gln
        195                 200                 205

Ser Arg Pro Pro Pro Ser Ser Asn Ile His Arg Pro Lys Pro Ser Arg
    210                 215                 220

Pro Val Pro Gly Ser Thr Ser Lys Leu Gly Asp Ala Thr Lys Ser Ser
```

```
              225                 230                 235                 240
        Met Thr Leu Asp Leu Gly Ser Ala Ser Arg Cys Asp Asp Ser Phe Gly
                        245                 250                 255

Gly Gly Gly Asn Ser Gly Asn Ala Val Ile Pro Ser Asp Glu Thr Val
                        260                 265                 270

Phe Thr Pro Val Glu Asp Lys Cys Arg Leu Asp Val Asn Thr Glu Leu
                        275                 280                 285

Asn Ser Ser Ile Glu Asp Leu Leu Glu Ala Ser Met Pro Ser Ser Asp
                290                 295                 300

Thr Thr Val Thr Phe Lys Ser Glu Val Ala Val Leu Ser Pro Glu Lys
        305                 310                 315                 320

Ala Glu Asn Asp Asp Thr Tyr Lys Asp Asp Val Asn His Asn Gln Lys
                        325                 330                 335

Cys Lys Glu Lys Met Glu Ala Glu Glu Glu Ala Leu Ala Ile Ala
                        340                 345                 350

Met Ala Met Ser Ala Ser Gln Asp Ala Leu Pro Ile Val Pro Gln Leu
                        355                 360                 365

Gln Val Glu Asn Gly Glu Asp Ile Ile Ile Gln Gln Asp Thr Pro
                370                 375                 380

Glu Thr Leu Pro Gly His Thr Lys Ala Lys Gln Pro Tyr Arg Glu Asp
        385                 390                 395                 400

Ala Glu Trp Leu Lys Gly Gln Gln Ile Gly Leu Gly Ala Phe Ser Ser
                        405                 410                 415

Cys Tyr Gln Ala Gln Asp Val Gly Thr Gly Thr Leu Met Ala Val Lys
                        420                 425                 430

Gln Val Thr Tyr Val Arg Asn Thr Ser Ser Glu Gln Glu Glu Val Val
                        435                 440                 445

Glu Ala Leu Arg Glu Glu Ile Arg Met Met Gly His Leu Asn His Pro
                450                 455                 460

Asn Ile Ile Arg Met Leu Gly Ala Thr Cys Glu Lys Ser Asn Tyr Asn
        465                 470                 475                 480

Leu Phe Ile Glu Trp Met Ala Gly Gly Ser Val Ala His Leu Leu Ser
                        485                 490                 495

Lys Tyr Gly Ala Phe Lys Glu Ser Val Val Ile Asn Tyr Thr Glu Gln
                        500                 505                 510

Leu Leu Arg Gly Leu Ser Tyr Leu His Glu Asn Gln Ile Ile His Arg
                        515                 520                 525

Asp Val Lys Gly Ala Asn Leu Leu Ile Asp Ser Thr Gly Gln Arg Leu
                530                 535                 540

Arg Ile Ala Asp Phe Gly Ala Ala Ala Arg Leu Ala Ser Lys Gly Thr
        545                 550                 555                 560

Gly Ala Gly Glu Phe Gln Gly Gln Leu Leu Gly Thr Ile Ala Phe Met
                        565                 570                 575

Ala Pro Glu Val Leu Arg Gly Gln Tyr Gly Arg Ser Cys Asp Val
                        580                 585                 590

Trp Ser Val Gly Cys Ala Ile Ile Glu Met Ala Cys Ala Lys Pro Pro
                        595                 600                 605

Trp Asn Ala Glu Lys His Ser Asn His Leu Ala Leu Ile Phe Lys Ile
                610                 615                 620

Ala Ser Ala Thr Thr Ala Pro Ser Ile Pro Ser His Leu Ser Pro Gly
        625                 630                 635                 640

Leu Arg Asp Val Ala Val Arg Cys Leu Glu Leu Gln Pro Gln Asp Arg
                        645                 650                 655
```

Pro Pro Ser Arg Glu Leu Leu Lys His Pro Val Phe Arg Thr Thr Trp
            660                 665                 670

<210> SEQ ID NO 20
<211> LENGTH: 1314
<212> TYPE: PRT
<213> ORGANISM: Homo sapiens

<400> SEQUENCE: 20

Met Met Met Asp Ile Leu Asn Thr Gln Gln Lys Ala Ala Glu Gly
1               5                   10                  15

Gly Arg Val Leu Ala Pro His Thr Ile Ser Ser Lys Leu Val Lys Arg
            20                  25                  30

Leu Ser Ser His Ser Ser His Lys Leu Ser Arg Ser Asp Leu Lys Ala
            35                  40                  45

Leu Gly Gly Ser Glu Thr Ile Ser Asp Gly Pro Ser Gln Leu Thr Phe
        50                  55                  60

Lys Asp Arg Tyr Val Phe Asn Glu Ser Leu Tyr Leu Lys Lys Leu Lys
65                  70                  75                  80

Lys Thr Ala Leu Asp Asp Tyr Tyr Thr Arg Gly Ile Lys Leu Thr Asn
                85                  90                  95

Arg Tyr Glu Glu Asp Asp Gly Asp Glu Ile Ile Arg Leu Ser Asn
            100                 105                 110

Gly Asp Arg Ile Asp Glu Asp Leu His Ser Gly Val Lys Phe Phe Ser
            115                 120                 125

Thr Thr Pro Tyr Cys Arg Lys Met Arg Ser Asp Ser Asp Glu Leu Ala
            130                 135                 140

Trp Asn Glu Ile Ala Thr Glu Arg Phe Lys Trp Gln Ser Met Leu Ala
145                 150                 155                 160

Arg Val Leu Lys Gly Asp Ile Val Lys Gly Glu Lys Thr Arg Ile Ala
                165                 170                 175

Asn Gln Val Lys Lys Pro Gly Leu Asn Lys Glu Leu Ser Asp Glu Ile
                180                 185                 190

Trp Leu Glu Leu Lys Ala Trp Leu Asn Gly Arg Thr Met Gln Glu Met
            195                 200                 205

Glu Gln Ser Leu Thr Tyr Leu Arg Asp Ser Ser Asp Ser Val Phe Glu
            210                 215                 220

Glu Ile Met Lys Phe Gln Ile Pro Gln Gly Lys Ile Leu Ser Leu Asp
225                 230                 235                 240

Ala Leu Glu Ala Ile Leu Gln Asp Leu Met Asn Arg Tyr His Ser Val
                245                 250                 255

Val Ser Tyr Trp Pro Asn Leu Lys Lys Met Tyr Lys Asp Lys Pro Ile
                260                 265                 270

Thr Asn Thr Ala Glu Phe Thr Ala Arg Ile Asp Val Met Asn Ser Trp
            275                 280                 285

Leu Asn Phe Lys Thr Asn Leu Thr Leu Arg Arg Gln Glu Leu Asp Asp
            290                 295                 300

Trp Ile Asn Arg Phe Ser Pro Ile Ser Ser Asp Asn Cys Gln Glu
305                 310                 315                 320

Asp Phe Asp Gly Val Pro Gln Trp Asn Cys Lys Met Lys Ile Leu Ala
                325                 330                 335

Glu Gln Leu Met Lys Glu Lys Asn Ile Glu Ser Ile Phe Gln Lys Lys
            340                 345                 350

Ile Phe Tyr Pro Leu Ser Pro Trp Met Phe Lys Leu Lys Leu His Phe
            355                 360                 365

```
Ile Val Tyr Arg Glu Thr Leu Thr Lys Met Asn Ile Lys Tyr Pro Tyr
            370                 375                 380

Glu Arg Leu Arg Ser Leu Leu Ala Phe Pro Val Tyr Leu Ile Lys Glu
385                 390                 395                 400

Val Ile Leu Thr Arg Leu Ser Tyr Ala Arg Lys Leu Lys Asn Pro Thr
                405                 410                 415

Met Met Met Ile Asp Gln Met Ile Asp Asp Phe Asn Ala Phe Ile Arg
            420                 425                 430

Leu Ser Val Gln Leu Lys Tyr Thr Leu Thr Lys Tyr Cys Ser Asn Leu
        435                 440                 445

Pro Phe Asp Val Asp Phe Asp Pro Thr Phe Glu Asn Thr Val Ile Glu
    450                 455                 460

Ala Ile Arg Tyr Leu Phe Phe Leu Leu Asn Leu Lys Leu Ile Asp Ser
465                 470                 475                 480

Ser Lys Gln Asn Phe Lys Ala Pro Asp Leu Leu Leu Lys Tyr Trp Asp
                485                 490                 495

His Leu Lys Asn Thr Gly His Tyr Ile Asn Gly Ala Glu Thr Val Ile
            500                 505                 510

Pro Asn Glu Phe Leu Lys Leu Thr Leu Arg Leu Val His Lys Leu Gln
        515                 520                 525

Phe Tyr Leu Leu Lys Gln Gln Asn Phe Pro Pro Thr Phe Ala Asn Ala
    530                 535                 540

Ser Glu Ala Glu Lys Trp Leu Ser Ser Ile Phe Glu Asn Leu Gly Ala
545                 550                 555                 560

Met Lys Arg Lys Leu Asn Arg Phe Ser Asn Ile Leu Val Lys Ala Phe
                565                 570                 575

Gln Asn Ser Ala Val Tyr Gln Ile Asn His Asn Ala Gln Leu Val Lys
            580                 585                 590

Lys Leu Lys Asp Ala His Tyr Phe Leu Val Tyr Ser Gly Asn Thr Phe
        595                 600                 605

Glu Ser Ser Gly Val Tyr Met Phe Ala Ala Pro Glu Leu Leu Gly Cys
    610                 615                 620

Asp Asn Asp Thr Ile Leu Arg Ile Leu Arg Asn Lys Ser Ile Gly Cys
625                 630                 635                 640

Asp Leu Val Pro Lys Leu Asp Ile Gly Asn Asn Leu Asn Val Tyr Asp
                645                 650                 655

Ile Thr Thr Lys Glu Thr Asp Leu Asn Ile Leu Val Ser Lys Gly Glu
            660                 665                 670

Asp Ser Lys Gly Ile Pro Tyr Tyr Arg Val Val Ala Asn Ser Ser Ser
        675                 680                 685

Asp Leu Asp Arg His Ala His Gln Ser Lys Lys Asn Phe Ser Thr
    690                 695                 700

Asp Pro Phe Asp Gln His Leu Asp Glu Lys Asn Asn Glu Val Phe Glu
705                 710                 715                 720

Leu Glu Val Ala Leu Ser Ser Leu Gly Ala Leu Val Val Leu Tyr Pro
                725                 730                 735

Gly Glu Pro Val Val Trp Asp Gly Pro Val Tyr Lys Leu Pro Gly Asn
            740                 745                 750

Asn Leu Phe Ala Ser Asn Glu Met Asp Leu Gly Lys Ile Gly Asn Pro
        755                 760                 765

Asn Thr Leu Ile Leu Leu Asn Gln Gly Ser Asn Tyr Ala Leu Thr Tyr
    770                 775                 780

Gln Ile Asp Lys Phe Asn Gln Thr Val Gly Asp Ser Val Ser Phe Ile
785                 790                 795                 800
```

```
Glu Lys Arg Cys Ser Leu Asn Ser Ile Glu Ser Ser Leu Gln Lys Ile
            805                 810                 815
Asn Lys Ala Tyr Tyr Lys Leu Thr Tyr Thr Val Leu Asn Asn Tyr Lys
            820                 825                 830
Gly Ile Leu Gly Ser Phe Met Lys Gln Cys Pro Gly Asn Glu Leu Leu
            835                 840                 845
Asn Ser Ile Phe Met Phe Gly Arg Asp Phe Gly Arg Ser Phe Leu Lys
            850                 855                 860
Tyr Asn Ala Phe Ser Ser Lys Arg Lys Tyr Val Ile Ile Phe Leu Met
865                 870                 875                 880
Val Lys Leu Gly Met Asn Trp Leu Lys Phe Leu Val Glu Glu Cys Asp
            885                 890                 895
Pro Thr Asp Gln Arg Thr Phe Arg Trp Cys Val Leu Ala Met Asp Phe
            900                 905                 910
Ala Met Gln Met Thr Ser Gly Tyr Asn Ile Leu Ala Leu Asn Val Lys
            915                 920                 925
Gln Phe Gln Glu Leu Lys Glu Arg Val Ser Val Cys Met Ser Leu Leu
            930                 935                 940
Ile Ser His Phe Asp Val Met Gly Ala Arg Ala Thr Glu Ala Glu Asn
945                 950                 955                 960
Gly Met Gln Gln Ala Arg Leu Asn Ile Asp Thr Glu Glu Asn Ile Asp
            965                 970                 975
Glu Glu Ala Thr Leu Glu Ile Asn Ser Arg Leu Arg Leu Glu Ala Ile
            980                 985                 990
Lys Thr Leu Glu Lys Thr Met Lys Arg Asn Pro Arg Gln Met Gly Lys
            995                 1000                1005
Val Leu Asp Ala Thr Asp Gln Gly Asn Lys Tyr Leu Leu Ser Leu
            1010                1015                1020
Ala Ser Ser Leu Ser Asn Val Ser Met Arg Trp Gln Lys Arg Ser
            1025                1030                1035
Phe Ile Gly Gly Gly Thr Phe Gly Gln Val Tyr Ser Ala Ile Asn
            1040                1045                1050
Leu Glu Asn Gly Glu Ile Leu Ala Val Lys Glu Ile Lys Ile His
            1055                1060                1065
Asp Thr Thr Thr Met Lys Lys Ile Phe Pro Leu Ile Lys Glu Glu
            1070                1075                1080
Met Thr Val Leu Glu Met Leu Asn His Pro Asn Ile Val Gln Tyr
            1085                1090                1095
Tyr Gly Val Glu Val His Arg Asp Lys Val Asn Ile Phe Met Glu
            1100                1105                1110
Tyr Cys Glu Gly Gly Ser Leu Ala Ser Leu Leu Asp His Gly Arg
            1115                1120                1125
Ile Glu Asp Glu Met Val Thr Gln Val Tyr Thr Phe Glu Leu Leu
            1130                1135                1140
Glu Gly Leu Ala Tyr Leu His Gln Ser Gly Val Val His Arg Asp
            1145                1150                1155
Ile Lys Pro Glu Asn Ile Leu Leu Asp Phe Asn Gly Ile Ile Lys
            1160                1165                1170
Tyr Val Asp Phe Gly Thr Ala Arg Thr Val Val Gly Ser Arg Thr
            1175                1180                1185
Arg Thr Val Arg Asn Ala Ala Val Gln Asp Phe Gly Val Glu Thr
            1190                1195                1200
Lys Ser Leu Asn Glu Met Met Gly Thr Pro Met Tyr Met Ala Pro
```

```
                  1205                1210                1215

Glu Thr Ile Ser Gly Ser Ala Val Lys Gly Lys Leu Gly Ala Asp
    1220                1225                1230

Asp Val Trp Ala Leu Gly Cys Val Val Leu Glu Met Ala Thr Gly
    1235                1240                1245

Arg Arg Pro Trp Ser Asn Leu Asp Asn Glu Trp Ala Ile Met Tyr
    1250                1255                1260

His Val Ala Ala Gly Arg Ile Pro Gln Leu Pro Asn Arg Asp Glu
    1265                1270                1275

Met Thr Ala Ala Gly Arg Ala Leu Leu Gly Lys Val Phe Gly Ser
    1280                1285                1290

Arg Pro His Tyr Glu Gly Tyr Cys Cys Gly Thr Thr Asp Arg Pro
    1295                1300                1305

Leu Asp Asp Thr Asn Pro
    1310

<210> SEQ ID NO 21
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue at postion 1 is modified by a N-
      terminal acetyl group.
<220> FEATURE:
<221> NAME/KEY: misc_feature
<222> LOCATION: (4)..(4)
<223> OTHER INFORMATION: Residue at postion 4 is modified by a C-
      terminal 4-methyl-coumaryl-7-amide group.

<400> SEQUENCE: 21

Asp Glu Val Asp
1

<210> SEQ ID NO 22
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue at postion 1 is modified by a N-
      terminal acetyl group.
<220> FEATURE:
<221> NAME/KEY: misc_feature
<222> LOCATION: (4)..(4)
<223> OTHER INFORMATION: Residue at postion 1 is modified by a C-
      terminal chloromethylketone group.

<400> SEQUENCE: 22

Tyr Val Ala Asp
1

<210> SEQ ID NO 23
<211> LENGTH: 501
<212> TYPE: PRT
<213> ORGANISM: Homo sapiens

<400> SEQUENCE: 23

Met Ala Ala Ala Ser Val Thr Pro Pro Gly Ser Leu Glu Leu Leu Gln
1               5                   10                  15
```

```
Pro Gly Phe Ser Lys Thr Leu Leu Gly Thr Lys Leu Glu Ala Lys Tyr
            20                  25                  30

Leu Cys Ser Ala Cys Arg Asn Val Leu Arg Arg Pro Phe Gln Ala Gln
        35                  40                  45

Cys Gly His Arg Tyr Cys Ser Phe Cys Leu Ala Ser Ile Leu Ser Ser
    50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
        130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
            180                 185                 190

Gly Lys Lys Lys Ile Pro Arg Glu Lys Phe Gln Asp His Val Lys Thr
        195                 200                 205

Cys Gly Lys Cys Arg Val Pro Cys Arg Phe His Ala Ile Gly Cys Leu
    210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
        275                 280                 285

Leu Asn Arg Glu Val Glu Arg Val Ala Met Thr Ala Glu Ala Cys Ser
    290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
            340                 345                 350

Val Phe Ile Trp Lys Ile Ser Asp Phe Ala Arg Lys Arg Gln Glu Ala
        355                 360                 365

Val Ala Gly Arg Ile Pro Ala Ile Phe Ser Pro Ala Phe Tyr Thr Ser
    370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
            420                 425                 430

Met Leu Leu Asp Gln Asn Asn Arg Glu His Val Ile Asp Ala Phe Arg
        435                 440                 445
```

```
Pro Asp Val Thr Ser Ser Ser Phe Gln Arg Pro Val Asn Asp Met Asn
    450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
            500
```

MODULATORS OF TNF RECEPTOR ASSOCIATED FACTOR (TRAF), THEIR PREPARATION AND USE

FIELD OF THE INVENTION

The present invention concerns DNA sequences encoding proteins capable of binding to TRAF2, the proteins encoded thereby, and the use of said proteins and DNA sequences in the treatment or prevention of a pathological condition associated with NF-κB induction or with any other activity mediated by TRAF2 or by other molecules to which said proteins bind.

BACKGROUND OF THE INVENTION

The Tumor Necrosis Factor/Nerve Growth Factor (TNF/NGF) receptor superfamily is defined by structural homology between the extracellular domains of its members (Bazan, 1993; Beutler and van Huffel, 1994; Smith et al., 1994). Except for two receptors, the p55 TNF receptor and Fas/APO1, the various members of this receptor family do not exhibit clear similarity of structure in their intracellular domains. Nevertheless, there is much similarity of function between the receptors, indicating that they share common signaling pathways. One example for this similarity is the ability of several receptors of the TNF/NGF family to activate the transcription factor NF-κB This common ability was ascribed to a capability of a cytoplasmic protein that activates NF-κB, TNF Receptor Associated Factor 2 (TRAF2) to bind to the structurally-dissimilar intracellular domains of several of the receptors of the TNF/NGF family. By what mechanisms does TRAF2 act and how is its responsiveness to the different receptors to which it binds coordinated is not known.

TRAF2 is a member of a recently described family of proteins called TRAF that includes several proteins identified as, for example, TRAF1, TRAF2 (Rothe, M., Wong, S. C., Henzel, W. J. and Goeddel, D (1994) Cell 78:681-692; PCT published application WO 95/33051), TRAF3 (Cheng, G. et al. (1995)), and TRAF6 (see Cao et al., 1996a).

All proteins belonging to the TRAF family share high degree of amino acid identity in their C-terminal domains, while their N-terminal domains may be unrelated. As shown in a schematic illustration of TRAF2 (FIG. 1), the molecule contains a ring finger motif and two TFIIIA-like zinc finger motifs at its C-terminal area. The C-terminal half of the molecule includes a region known as the "TRAF domain" containing a potential leucine zipper region extending between amino acids 264-358 (called N-TRAF), and another part towards the carboxy end of the domain between amino acids 359-501 (called C-TRAF) which is responsible for TRAF binding to the receptors and to other TRAF molecules to form homo- or heterodimers.

Activation of the transcription factor NF-κB is one manifestation of the signaling cascade initiated by some of the TNF/NGF receptors and mediated by TRAF2. NF-κB comprises members of a family of dimer-forming proteins with homology to the Rel oncogene which, in their dimeric form, act as transcription factors. These factors are ubiquitous and participate in regulation of the expression of multiple genes. Although initially identified as a factor that is constitutively present in B cells at the stage of Igκ light chain expression, NF-κB is known primarily for its action as an inducible transcriptional activator. In most known cases NF-κB behaves as a primary factor, namely the induction of its activity is by activation of pre-existing molecules present in the cell in their inactive form, rather than its de-novo synthesis which in turn relies on inducible transcription factors that turn-on the NF-κB gene. The effects of NF-κB are highly pleiotropic. Most of these numerous effects share the common features of being quickly induced in response to an extracellular stimulus. The majority of the NF-κB-activating agents are inducers of immune defense, including components of viruses and bacteria, cytokines that regulate immune response, UV light and others. Accordingly, many of the genes regulated by NF-κB contribute to immune defense (see Blank et al., 1992; Grilli et al., 1993; Baeuerle and Henkel, 1994, for reviews).

One major feature of NF-κB-regulation is that this factor can exist in a cytoplasmic non-DNA binding form which can be induced to translocate to the nucleus, bind DNA and activate transcription. This dual form of the NF-κB proteins is regulated by I-κB—a family of proteins that contain repeats of a domain that has initially been discerned in the erythrocyte protein ankyrin (Gilmore and Morin, 1993). In the unstimulated form, the NF-κB dimer occurs in association with an I-κB molecule which imposes on it cytoplasmic location and prevents its interaction with the NF-κB-binding DNA sequence and activation of transcription. The dissociation of I-κB from the NF-κB dimer constitutes the critical step of its activation by many of its inducing agents (DiDonato et al., 1995). Knowledge of the mechanisms that are involved in this regulation is still limited. There is also just little understanding of the way in which cell specificity in terms of responsiveness to the various NF-κB-inducing agents is determined.

One of the most potent inducing agents of NF-κB is the cytokine tumor necrosis factor (TNF). There are two different TNF receptors, the p55 and p75 receptors. Their expression levels vary independently among different cells (Vandenabeele et al. 1995). The p75 receptor responds preferentially to the cell-bound form of TNF (TNF is expressed both as a beta-transmembrane protein and as a soluble protein) while the p55 receptor responds just as effectively to soluble TNF molecules (Grell et. al., 1995). The intracellular domains of the two receptors are structurally unrelated and bind different cytoplasmic proteins. Nevertheless, at least part of the effects of TNF, including the cytocidal effect of TNF and the induction of NF-κB. can be induced by both receptors. This feature is cell specific. The p55 receptor is capable of inducing a cytocidal effect or activation of NF-κB in all cells that exhibit such effects in response to TNF. The p75-R can have such effects only in some cells. Others, although expressing the p75-R at high levels, show induction of the effects only in response to stimulation of the p55-R (Vandenabeele et al., 1995). Apart from the TNF receptors, various other receptors of the TNF/NGF receptor family; CD30 McDonald et al., 1995). CD40 (Berberich et al., 1994; Lalmanach-Girard et al., 1993), the lymphotoxin beta receptor and, in a few types of cells, Fas/APO1 (Rensing-Ehl et al., 1995), are also capable of inducing activation of NF-βB. The IL-1 type I receptor, also effectively triggering NF-βB.

The activation of NF-κB upon triggering of these various receptors results from induced phosphorylation of its associated I-κB molecules. This phosphorylation tags I-κB to degradation, which most likely occurs in the proteasome. The nature of the kinase that phosphorylates I-κB, and its mechanism of activation upon receptor triggering is still unknown. However, in the recent two years some knowledge has been gained as to the identity of three receptor-associated proteins that appear to take part in initiation of the phosphorylation (see diagrammatic illustration in FIGS. 2A and 6A-G). A protein called TRAF2, initially cloned by D. Goeddel and his colleagues (Rothe et al., 1994), seems to play a central role in NF-κB-activation by the various receptors of the TNF/NGF family. The protein, which when expressed at high levels can by itself trigger NF-κB activation, binds to activated p75 TNF-R (Rothe et al., 1994), lymphotoxin beta receptor (Mosialos et al., 1995), CD40 (Rothe et al., 1995a) and CD-30 (unpublished data) and mediates the induction of NF-κB by them. TRAF2 does not bind to the p55 TNF receptor nor to Fas/APO1, however, it can bind to a p55 receptor-associated protein called TRADD and TRADD has the ability to bind to a Fas/APO1-associated protein called MORT1 (or FADD—see Boldin et al. 1995b and 1996). Another receptor-interacting protein, called RIP (see Stanger et al., 1995) is also capable of interacting with TRAF2 as well as with FAS/APO1, TRADD, the p55 TNF receptor and MORT-1. Thus, while RIP has been associated with cell cytotoxicity induction (cell death), its ability to interact with TRAF2 also implicates it in NF-κB activation and it also may serve in addition to augment the interaction between FAS/APO1, MORT-1, p55 TNF receptor and TRADD with TRAF2 in the pathway leading to NF-κB activation. These associations apparently allow the p55 TNF receptor and Fas/APO1 to trigger NF-κB activation (Hsu et al., 1995; Boldin et al., 1995; Chinnalyan et al., 1995; Varfolomeev et al., 1996; Hsu et al., 1996). The triggering of NF-κB activation by the IL-1 receptor occurs independently of TRAF2 and may involve a recently-cloned IL-1 receptor-associated protein-kinase called IRAK (Croston et al., 1995).

By what mechanism TRAF2 acts is not clear. Several cytoplasmic molecules that bind to TRAF2 have been identified (Rothe et al., 1994; Rothe et al., 1995b). However, the information on these molecules does not provide any clue as to the way by which TRAF2, which by itself does not possess any enzymatic activity, triggers the phosphorylation of I-κB. There is also no information yet of mechanisms that dictate cell-specific pattern of activation of TRAF2 by different receptors, such as observed for the induction of NF-κB by the two TNF receptors.

In addition to the above mentioned, of the various TRAF proteins, it should also be noted that TRAF2 binds to the p55 (CD120a) and p75 (CD120b) TNF receptors, as well as to several other receptors of the TNF/NGF receptor family, either directly or indirectly via other adaptor proteins as noted above, for example with reference to the FAS/APO1 receptor, and the adaptor proteins MORT-1, TRADD and RIP. As such, TRAF2 is crucial for the activation of NF-κB (see also Wallach, 1996). However, TRAF3 actually inhibits activation of NF-κB by some receptors of the TNF/NGF family (see Rothe et al., 1995a), whilst TRAF6 is required for induction of NF-κB by IL-1 (see Cao et al., 1996a).

Accordingly, as regards NF-κB activation and its importance in maintaining cell viability, the various intracellular pathways involved in this activation have heretofore not been clearly elucidated, for example, how the various TRAF proteins, are involved directly or indirectly.

Furthermore, as is now known regarding various members of the TNF/NGF receptor family and their associated intracellular signaling pathways inclusive of various adaptor, mediator/modulator proteins (see brief reviews and references in, for example, co-pending co-owned Israel Patent Application Nos. 114615, 114986, 115319, 116588), TNF and the FAS/APO1 ligand, for example, can have both beneficial and deleterious effects on cells. TNF, for example, contributes to the defense of the organism against tumors and infectious agents and contributes to recovery from injury by inducing the killing of tumor cells and virus-infected cells, augmenting antibacterial activities of granulocytes, and thus in these cases the TNF-induced cell killing is desirable. However, excess TNF can be deleterious and as such TNF is known to play a major pathogenic role in a number of diseases such as septic shock, anorexia, rheumatic diseases, inflammation and graft-vs-host reactions. In such cases TNF-induced cell killing is not desirable. The FAS/APO1 ligand, for example, also has desirable and deleterious effects. This FAS/APO1 ligand induces via its receptor the killing of autoreactive T cells during maturation of T cells, i.e., the killing of T cells which recognize self-antigens, during their development and thereby preventing autoimmune diseases. Further, various malignant cells and HIV-infected cells carry the FAS/APO1 receptor on their surface and can thus be destroyed by activation of this receptor by its ligand or by antibodies specific thereto, and thereby activation of cell death (apoptosis) intracellular pathways mediated by this receptor. However, the FAS/APO1 receptor may mediate deleterious effects, for example, uncontrolled killing of tissue which is observed in certain diseases such as acute hepatitis that is accompanied by the destruction of liver cells.

In view of the above, namely, that receptors of the TNF/NGF family can induce cell death pathways on the one hand and can induce cell survival pathways (via NF-κB induction) on the other hand, there apparently exists a fine balance, intracellularly between these two opposing pathways. For example, when it is desired to achieve maximal destruction of cancer cells or other infected or diseased cells, it would be desired to have TNF and/or the FAS/APO1 ligand inducing only the cell death pathway without inducing NF-κB. Conversely, when it is desired to protect cells such as in, for example, inflammation, graft-vs-host reactions, acute hepatitis, it would be desirable to block the cell killing induction of TNF and/or FAS/APO1 ligand and enhance, instead, their induction of NF-κB. Likewise, in certain pathological circumstances it would be desirable to block the intracellular signaling pathways mediated by the p75 TNF receptor and the IL-1 receptor, while in others it would be desirable to enhance these intracellular pathways.

SUMMARY OF THE INVENTION

It is an object of the invention to provide novel proteins, including all isoforms, analogs, fragments or derivatives thereof which are capable of binding to the tumor necrosis factor receptor-associated (TRAF) proteins. As the TRAF proteins are involved in the modulation or mediation of the activation of the transcription factor NF-κB, which is initiated by some of the TNF/NGF receptors, as well as others as noted above, the novel proteins of the present invention by binding to TRAF proteins are therefore capable of affecting (modulating or mediating) the intracellular signaling processes initiated by various ligands (e.g., TNF, FAS ligand and others) binding to their receptors such as, for example, their modulation/mediation of NF-κB activation, via interaction directly or indirectly with TRAF proteins.

The novel proteins of the present invention are therefore direct modulators/mediators of the intracellular biological activity of TRAF proteins (e.g., induction of NF-κB activation by TRAF2 and TRAF6 and inhibition of NF-κB activation, by TRAF3).

The novel proteins of the invention are likewise indirect modulators/mediators of the intracellular biological activity of a variety of other proteins which are capable of interacting with TRAF proteins directly or indirectly (e.g., FAS/APO1 receptor, p55 TNF receptor, p75 TNF receptor, IL-1 receptor and their associated proteins, such as, for example, MORT-1, TRADD, RIP).

Another object of the invention is to provide antagonists (e.g., antibodies, peptides, organic compounds, or even some isoforms) to the above novel TRAF-binding proteins, including isoforms, analogs, fragments and derivatives thereof, which may be used to inhibit the signaling process, or, more specifically, to inhibit the activation of NF-κB and its associated involvement in cell-survival processes, when desired. Likewise, when the TRAF-binding proteins of the invention or the TRAF protein to which they bind (e.g., TRAF3) are themselves inhibitory for NF-κB activation, then it is an object to provide antagonists to these TRAF-binding proteins to activate the signaling process or more specifically, to block the inhibition of NF-κB activation and hence bring about enhanced NF-κB activation, when desired.

A further object of the invention is to use the above novel TRAF-binding proteins, isoforms, analogs, fragments and derivatives thereof, to isolate and characterize additional proteins or factors, which may be involved in regulation of TRAF protein activity and/or the above noted receptor activity, e.g., other proteins which may bind to TRAF proteins and influence their activity, and/or to isolate and identify other receptors or other cellular proteins further upstream or downstream in the signaling process(es) to which these novel proteins, analogs, fragments and derivatives bind, and hence, in whose function they are also involved.

A still further object of the invention is to provide inhibitors which can be introduced into cells to bind or interact with the novel TRAF-binding proteins and possible isoforms thereof, which inhibitors may act to inhibit TRAF protein-associated activity in, for example, NF-κB activation and hence, when desired, to inhibit NF-κB activation; or which may act to inhibit inhibitory TRAF-associated activity (e.g., TRAF3) in NF-κB activation and hence, when desired, to enhance NF-κB activation.

Moreover, it is an object of the present invention to use the above-mentioned novel TRAF-binding proteins, isoforms and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g., for identifying disorders related to abnormal functioning of cellular effects mediated directly by TRAF proteins or mediated by the p55 TNF receptor, FAS/APO1 receptor, or other related receptors and their associated cellular proteins (e.g., MORT-1, TRADD, RIP), which act directly or indirectly to modulate/mediate intracellular processes via interaction with TRAF proteins.

A further object of the invention is to provide pharmaceutical compositions comprising the above novel TRAF proteins, isoforms, or analogs, fragments or derivatives thereof, as well as pharmaceutical compositions comprising the above noted antibodies or other antagonists.

In accordance with the present invention, a number of novel TRAF-binding proteins, in particular, TRAF2-binding proteins, have been isolated. These TRAF2-binding proteins have high specificity of binding to TRAF2 (see Examples below) and hence are modulators or mediators of TRAF2 intracellular activity. TRAF2 is involved in the modulation or mediation of at least one intracellular signaling pathway being the cell survival- or viability-related pathway in which TRAF2 is directly involved in activation of NF-κB which plays a central role in cell survival. In fact, one of these new proteins, called NIK (for 'NF-κB inducing kinase') binds to TRAF2 and stimulates NF-κB activity. NIK is a kinase sharing sequence similarity with several MAPKK kinases (see below). Further, TRAF2 by being capable of interaction directly or indirectly with the above noted p55 TNF receptor, p75 TNF receptor, FAS/APO1 receptors and their associated proteins MORT-1, TRADD and RIP, also is a mediator or modulator of the NF-κB induction or activation activity attributed to these receptors. TRAF2 is therefore a modulator/mediator of the cell survival pathways (as opposed to the cell death pathways) mediated by these receptors and their associated proteins and as such the extent of interaction between these receptors and/or proteins with TRAF2 is an important factor in the outcome of the activity of these receptors (once activated by their ligands), namely, whether the cells will survive or die. Accordingly, the proteins of the invention, for example, NIK, play a key role in this interaction between TRAF2 and the other proteins/receptors with which TRAF2 interacts, as proteins such as NIK by binding specifically to TRAF2 will modulate its activity and/or will have their activity modulated by interaction with TRAF2.

The TRAF-binding proteins, such as, for example, the TRAF2-binding proteins, including NIK, have been isolated and cloned using the two-hybrid system, partially and fully sequenced, and characterized, and as is detailed herein below appear to be highly specific TRAF2-binding proteins, and hence specific TRAF2 modulators/mediators.

As will be used herein throughout, TRAF protein activity, for example TRAF2 activity, is meant to include its activity in modulation/mediation in the cell survival pathway, especially as concerns NF-κB induction/activation. Likewise, as used herein throughout TRAF-binding protein, in particular TRAF2-binding protein, activity is meant to include their modulation/mediation of TRAF-, in particular, TRAF2-activity by virtue of their specific binding to TRAF, especially TRAF2 proteins, this modulation/mediation including modulation/mediation of cell survival pathways, in particular, those relating to NF-κB activation/induction in which TRAF proteins, especially TRAF2 is involved directly or indirectly and as such TRAF or TRAF2-binding protein may be considered as indirect modulator/mediators of all the above mentioned proteins and possibly a number of others which are involved in cell survival, especially NF-κB activation/induction and to which TRAF2 (or other TRAF proteins) binds, or with which TRAF2 (or other TRAF proteins) interacts in a direct or indirect fashion.

Accordingly, the present invention provides a DNA sequence encoding a protein capable of binding to a tumor necrosis factor receptor-associated (TRAF) molecule.

One embodiment of the DNA sequence of the invention is a sequence encoding a protein capable of binding to TRAF2.

Another embodiment of the DNA sequence of the invention is a sequence encoding a protein capable of binding to at least the amino acid residues 222-501 of the amino acid sequence of TRAF2.

Other embodiments of the DNA sequence of the invention include:
(a) a cDNA sequence of the herein designated clone 9 comprising the nucleotide sequence depicted in FIGS. 3A-C;
(b) a cDNA sequence of the herein designated clone 10 comprising the nucleotide sequence depicted in FIGS. 4A-B;
(c) a cDNA sequence of the herein designated clone 15 comprising the nucleotide sequence depicted in FIG. 5A;
(d) a fragment of a sequence (a)-(c) which encodes a biologically active protein capable of binding to least the 222-501 amino acid sequence of TRAF2;
(e) a DNA sequence capable of hybridization to a sequence of (a)-(d) under moderately stringent conditions and which encodes a biologically active protein capable of binding to at least the 222-501 amino acid sequence of TRAF2; and (f) a DNA sequence which is degenerate as a result of the genetic code to the DNA sequences defined in (a)-(e) and which encodes a biologically active protein capable of binding to at least the 222-501 amino acid sequence of TRAF2.

Yet other embodiments of the DNA sequence of the invention noted above include:

A DNA sequence selected from the sequences contained in the herein designated cDNA clones 9 and 15;

A DNA sequence which encodes a protein that also modulates NF-κB activity; and

A DNA sequence selected from the sequences contained in the herein designated cDNA clone 10.

An additional preferred embodiment of the above DNA sequences of the invention is a DNA sequence comprising the DNA sequence encoding the protein NIK (for 'NF-κB inducing kinase').

Embodiments of the above DNA sequence of the invention encoding the protein NIK include:

(i) A DNA sequence encoding the protein NIK, isoforms, fragments or analogs thereof, said NIK, isoforms, fragments or analogs thereof being capable of binding to TRAF2 and which is capable of modulating the activity of NF-κB;

(ii) A DNA sequence as in (i) above, selected from the group consisting of:
 a) a cDNA sequence derived from the coding region of a native NIK protein;
 b) DNA sequences capable of hybridization to a sequence of (a) under moderately stringent conditions and which encode a biologically active NIK; and
 c) DNA sequences which are degenerate as a result of the genetic code to the sequences defined in (a) and (b) and which encode a biologically active NIK protein;

(iii) A DNA sequence as in (i) or (ii) above comprising at least part of the sequence depicted in FIGS. 6A-G and encoding at least one active NIK protein, isoform, analog or fragment;

(iv) A DNA sequence as in (iii) above encoding a NIK protein, isoform, analog or fragment having at least part of the amino acid sequence depicted in FIGS. 6A-G.

In another aspect, the invention provides proteins or polypeptides encoded by the above noted DNA coding sequences of the invention, the isoforms, analogs, fragments and derivatives of said proteins and polypeptides, provided that they are capable of binding to TRAF2, preferably to at least the 222-501 amino acid sequenced of TRAF2. Embodiments of these proteins/polypeptides, and their isoforms, analogs, fragments and derivatives according to the invention include:

(a) a protein being the protein encoded by herein designated clone 10;

(b) a protein, isoforms, fragments, analogs and derivatives thereof, being the NIK protein, isoforms, analogs, fragments and derivatives thereof encoded by the above noted DNA sequences encoding said NIK protein, isoforms, analogs, fragments and derivatives; and (c) a NIK protein, isoforms, analogs, fragments and derivatives thereof being the NIK protein, isoforms, analogs, fragments and derivatives thereof encoded by the above noted DNA sequences encoding said NIK protein, isoforms, analogs, fragments and derivatives, wherein said protein, isoforms, fragments and derivatives have at least part of the amino acid sequence depicted in FIGS. 6A-G.

In yet another aspect, the invention provides a vector comprising any of the above DNA sequences according to the invention which are capable of being expressed in host cells selected from prokaryotic and eukaryotic cells; and the transformed prokaryotic and eukaryotic cells containing said vector.

The invention also provides a method for producing a protein, isoform, analog, fragment or derivative encoded by any of the above DNA sequences according to the invention which comprises growing the above mentioned transformed host cells under conditions suitable for the expression of said protein, isoforms, analogs, fragments or derivatives, effecting post-translational modification, as necessary, for obtaining said protein, isoform, analogs, fragments or derivatives and isolating said expressed protein, isoforms, analogs, fragments or derivatives.

In a further aspect, the invention provides antibodies or active fragments or derivatives thereof, specific for the above TRAF-binding proteins, analogs, isoforms, fragments or derivatives thereof or specific for the NIK protein, isoform, analog, fragment or derivative thereof noted above.

In a different aspect, the invention provides the following screening methods:

(i) A method for screening of a ligand capable of binding to a protein according to the invention, as noted above, including isoforms, analogs, fragments or derivatives thereof, comprising contacting an affinity chromatography matrix to which said protein, isoform, analog, fragment or derivative is attached with a cell extract whereby the ligand is bound to said matrix, and eluting, isolating and analyzing said ligand.

(ii) A method for screening of a DNA sequence coding for a ligand capable of binding to a protein, isoform, analog, fragment or derivative according to the invention as noted above, comprising applying the yeast two-hybrid procedure in which a sequence encoding said protein, isoform analog, derivative or fragment is carried by one hybrid vector and sequences from a cDNA or genomic DNA library are carried by the second hybrid vector, transforming yeast host cells with said vectors, isolating the positively transformed cells, and extracting said second hybrid vector to obtain a sequence encoding said ligand.

Similarly, there is also provided a method for isolating and identifying proteins, isoforms, analogs, fragments according to the invention noted above, capable of binding directly to TRAF2, comprising applying the yeast two-hybrid procedure in which a sequence encoding said TRAF2 is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said TRAF2.

In yet another aspect of the invention there is provided a method for the modulation or mediation in cells of the activity of NF-κB or any other intracellular signaling activity modulated or mediated by TRAF2 or by other molecules to which a protein, isoform, analog, fragment or derivative thereof of the invention as noted above, said method comprising treating said cells by introducing into said cells one or more of said protein, isoform, analog, fragment or derivative thereof in a form suitable for intracellular introduction thereof, or introducing into said cells a DNA sequence encoding said one or more protein, isoform, analog, fragment or derivative thereof in the form of a suitable vector carrying said sequence, said vector being capable of effecting the insertion of said sequence into said cells in a way that said sequence is expressed in said cells.

Embodiments of this above method for modulation/mediation in cells of the activity of NF-κB or any other intracellular signaling activity modulated or mediated by TRAF2 or other molecules include:

(i) A method as above, wherein said treating of cells comprises introducing into said cells a DNA sequence encoding said protein, isoform, fragment, analog or derivative in the form of a suitable vector carrying said sequence, said vector being capable of effecting the insertion of said sequence into said cells in a way that said sequence is expressed in said cells.

(ii) A method as above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of said cells to be treated and a second sequence encoding a protein selected from the said protein, isoforms, analogs, fragments and derivatives according to the invention, that when expressed in said cells is capable of modulating/mediating the activity of NF-κB or any other intracellular signaling activity modulated/mediated by TRAF2 or other said molecules; and (b) infecting said cells with said vector of (a).

Likewise, the present invention also provides a method for modulating TRAF2 modulated/mediated effect on cells comprising treating said cells with the antibodies or active fragments or derivatives thereof, according to the invention as noted above, said treating being by application of a suitable composition containing said antibodies, active fragments or derivatives thereof to said cells, wherein when the TRAF2-binding protein or portions thereof of said cells are exposed on the extracellular surface, said composition is formulated for extracellular application, and when said TRAF2-binding proteins are intracellular said composition is formulated for intracellular application.

Other methods of the invention for modulating the TRAF2 modulated/mediated effect on cells include:

(i) A method comprising treating said cells with an oligonucleotide sequence encoding an antisense sequence for at least part of the DNA sequence encoding a TRAF2-binding protein, this DNA sequence being any of the above mentioned ones of the invention, said oligonucleotide sequence being capable of blocking the expression of the TRAF2-binding protein.

(ii) A method as in (i) above wherein said oligonucleotide sequence is introduced to said cells via a recombinant virus as noted above, wherein said second sequence of said virus encodes said oligonucleotide sequence.

(iii) A method comprising applying the ribozyme procedure in which a vector encoding a ribozyme sequence capable of interacting with a cellular mRNA sequence encoding a TRAF2-binding protein, isoform, analog, fragment or derivative of the invention noted above, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said TRAF2-binding protein in said cells.

It should be noted that for all the above methods of the invention the protein of the invention as indicated, can be specifically NIK or at least one of the NIK isoforms, analogs, fragments and derivatives thereof.

In the above methods and embodiments thereof of the invention there is included also a method for the prevention or treatment of a pathological condition associated with NF-κB induction or with any other activity mediated by TRAF2 or by other molecules to which a protein, isoform, analog, fragment or derivative, according to the invention, binds, said method comprising administering to a patient in need an effective amount of a protein, isoform, analog, fragment or derivative, according to the invention, or a DNA molecule coding therefor, or a molecule capable of disrupting the interaction of said protein, isoform, analog, fragment or derivative, with TRAF2 or any other molecule to which said protein, isoform, analog, fragment or derivative binds. In this method of the invention, said protein of the invention administered to the patient in need can be specifically the protein encoded by clone 10, NIK, an isoform, analog, derivative or fragment of NIK, or a DNA molecule coding therefor. The protein encoded by clone 10 acts to inhibit NF-κB induction, as do other fragments of NIK, while NIK induces NF-κB activation.

In an additional aspect of the invention there is provided a pharmaceutical composition for the modulation of the TRAF2 modulated/mediated effect on cells comprising, as active ingredient at least one of the TRAF2-binding proteins, according to the invention, its biologically active fragments, analogs, derivatives or mixtures thereof.

Other pharmaceutical compositions or embodiments thereof according to the invention include:

(i) A pharmaceutical composition for modulating the TRAF2 modulated/mediated effect on cells comprising, as active ingredient, a recombinant animal virus vector encoding a protein capable of binding a cell surface receptor and encoding at least one TRAF2-binding protein, isoform, active fragments or analogs, according to the invention.

(ii) A pharmaceutical composition for modulating the TRAF2 modulated/mediated effect on cells comprising as active ingredient, an oligonucleotide sequence encoding an anti-sense sequence of the TRAF2-binding protein mRNA sequence according to the invention.

A further embodiment of the above pharmaceutical composition is specifically a pharmaceutical composition for the prevention or treatment of a pathological condition associated with NF-κB induction or with any other activity mediated by TRAF2 or by other molecules to which a protein, analog, isoform, fragment or derivative, according to the invention binds, said composition comprising an effective amount of a protein, analog, isoform, fragment or derivative, according to the invention or a DNA molecule coding therefor, or a molecule capable of disrupting the interaction of said protein, analog, isoform, fragment or derivative, with TRAF2 or any other molecule to which said protein, analog, isoform, fragment or derivative, binds. In a yet further specific embodiment said pharmaceutical composition comprising an effective amount of the protein encoded by clone 10, NIK, an isoform, analog, derivative or fragment of NIK, or a DNA molecule coding therefor.

In yet another specific embodiment, the invention provides a pharmaceutical composition for the prevention or treatment of a pathological condition associated with NF-κB induction or with any other activity mediated by TRAF2 or by other molecules to which the protein NIK binds, said composition comprising a molecule capable of interfering with the protein kinase activity of NIK. In this composition, the interfering molecule may be an effective amount of NIK mutated in active site residues, thus mutated NIK serving to interfere with native NIK, in particular, the kinase activity of NIK.

One known condition associated with NF-κB induction (abnormal) is AIDS, others are e.g., autoimmune diseases, as well as tumors.

Still further aspects and embodiments of the invention are:
(i) A method for identifying and producing a ligand capable of modulating the cellular activity modulated/mediated by TRAF2 comprising:
 a) screening for a ligand capable of binding to a polypeptide comprising at least a portion of TRAF2 having the amino acid residues 221-501 of TRAF2;
 b) identifying and characterizing a ligand, other than TRAF2 or portions of a receptor of the TNF/NGF receptor family, found by said screening step to be capable of said binding; and
 c) producing said ligand in substantially isolated and purified form.
(ii) A method for identifying and producing a ligand capable of modulating the cellular activity modulated/mediated by a protein, isoform, analog, fragment or derivative, according to the invention, comprising:
 a) screening for a ligand capable of binding to a polypeptide comprising at least a portion of the NIK sequence depicted in FIGS. 6A-G;
 b) identifying and characterizing a ligand, other than TRAF2 or portions of a receptor of the TNF/NGF receptor family, found by said screening step to be capable of said binding; and
 c) producing said ligand in substantially isolated and purified form.
(iii) A method for identifying and producing a ligand capable of modulating the cellular activity modulated/mediated by NIK comprising:
 a) screening for a ligand capable of binding to a polypeptide comprising at least a portion of the NIK sequence depicted in FIGS. 6A-G;
 b) identifying and characterizing a ligand, other than TRAF2 or portions of a receptor of the TNF/NGF receptor family, found by said screening step to be capable of said binding; and
 c) producing said ligand in substantially isolated and purified form.
(iv) A method for identifying and producing a ligand capable of directly or indirectly modulating the cellular activity modulated/mediated by NIK comprising:
 a) screening for a molecule capable of modulating activities modulated/mediated by NIK;
 b) identifying and characterizing said molecule; and
 c) producing said molecule in substantially isolated and purified form.
(v) A method for identifying and producing a molecule capable of directly or indirectly modulating the cellular activity modulated/mediated by a protein, isoform, analog, fragment or derivative of the invention, comprising:
 a) screening for a molecule capable of modulating activities modulated/mediated by a protein, isoform, analog, fragment or derivative according to the invention;
 b) identifying and characterizing said molecule; and
 c) producing said molecule in substantially isolated and purified form.

Other aspects and embodiments of the present invention are also provided as arising from the following detailed description of the invention.

It should be noted that, where used throughout, the following terms: "modulation/mediation of the TRAF (or TRAF2) effect on cells" and any other such "modulation/mediation" mentioned in the specification are understood to encompass in vitro as well as in vivo treatment and, in addition, also to encompass inhibition or enhancement/augmentation.

BRIEF DESCRIPTION OF THE DRAWINGS

FIGS. 2A-B show schematic diagrams illustrating some of the proteins involved in NF-κB activation, including the new TRAF-binding proteins of the present invention (e.g., NIK), in which FIG. 2A is a partial scheme and FIG. 2B is a more complete scheme.

FIGS. 3A-B show the nucleotide sequence (SEQ ID NO:1) of the 5' end of clone 9 (FIG. 3A (FIGS. 3A-1 through 3A-3)) and the deduced amino acid sequence (SEQ ID NO:2) encoded thereby (FIG. 3B).

FIG. 4 (FIGS. 4-1 through 4-2) show the nucleotide sequence (SEQ ID NO:3) of clone 10.

FIGS. 5A-B show the nucleotide sequence (SEQ ID NO:4) of clone 15 (FIG. 5A) and the deduced amino acid sequence (SEQ ID NO:5) encoded thereby (FIG. 5B).

FIG. 6 (FIGS. 6-1 through 6-7) show the nucleotide sequence (SEQ ID NO:6) and the deduced amino acid sequence (SEQ ID NO:7) of NIK.

FIG. 7 (FIGS. 7-1 through 7-28) shows an alignment of the sequence of protein NIK (s9, SEQ ID NO:14) with the sequence of the mouse protein kinase mMEKK (mouse MAPK or ERK Kinase Kinase) (s1, SEQ ID NO:19) and a number of other kinases, i.e., BYR2 (s2, SEQ ID NO:16), Tpl-2 (s3, SEQ ID NO:12), Ewing's sarcoma oncogene (s4, SEQ ID NO:13), SSC3 (s5, SEQ ID NO:20), STE11 (s6, SEQ ID NO:17), NPK1 (s7, SEQ ID NO:15), and BCK1 (s8, SEQ ID NO:18). The regions corresponding to the conserved motifs I to XI in protein kinases are marked.

DETAILED DESCRIPTION OF THE INVENTION

The present invention relates to DNA sequences encoding proteins capable of binding to a tumor necrosis factor receptor-associated factor (TRAF) molecule, and the proteins encoded thereby.

In a preferred embodiment, the present invention concerns cDNA sequences herein designated clone 9, clone 10 and clone 15 (depicted in FIGS. 3A-C, 4A-B and 5A, respectively), which encode for proteins capable of binding to TRAF2, and the proteins encoded by those DNA sequences.

In a further preferred embodiment the invention relates to the DNA sequence encoding the NIK protein, and the NIK protein itself.

The DNA and the deduced amino acid sequences mentioned above represent new sequences; they do not appear in the 'GENEBANK' or 'PROTEIN BANK' data banks of DNA or amino acid sequences.

Within the scope of the present invention are also fragments of the above mentioned DNA sequences and DNA sequences capable of hybridization to those sequences or part of them, under moderately stringent conditions, provided they encode a biologically active protein or polypeptide capable of binding to at least the 222-501 amino acid sequence of TRAF2.

The present invention also concerns a DNA sequence which is degenerate as a result of the genetic code to the above mentioned DNA sequences and which encodes a biologically active protein or polypeptide capable of binding to at least the 222-501 amino acid sequence of TRAF2.

Figure 1:
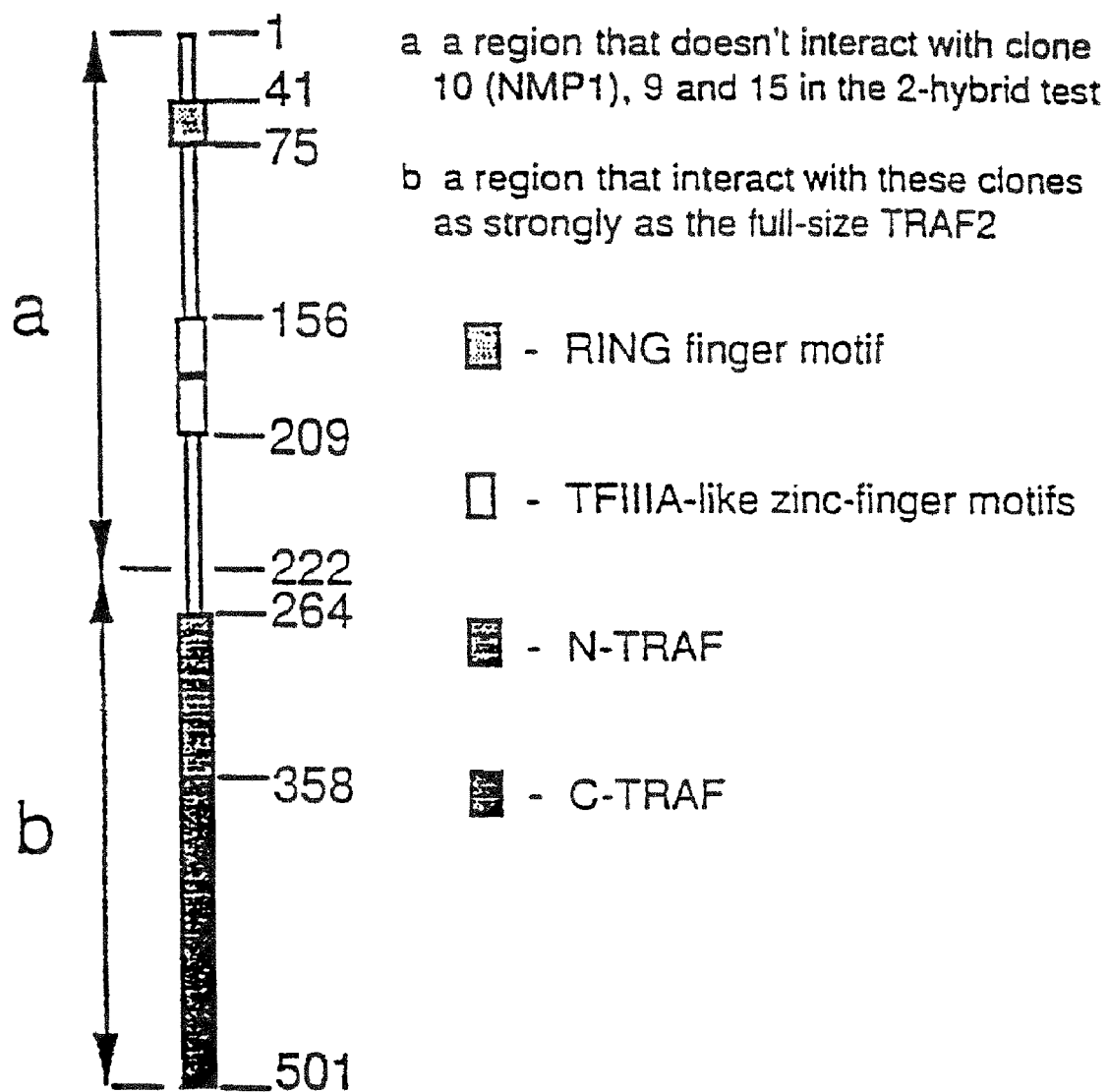
FIG. 1 shows a diagrammatic illustration of the structure of the TRAF2 molecule.
Figure 2A:
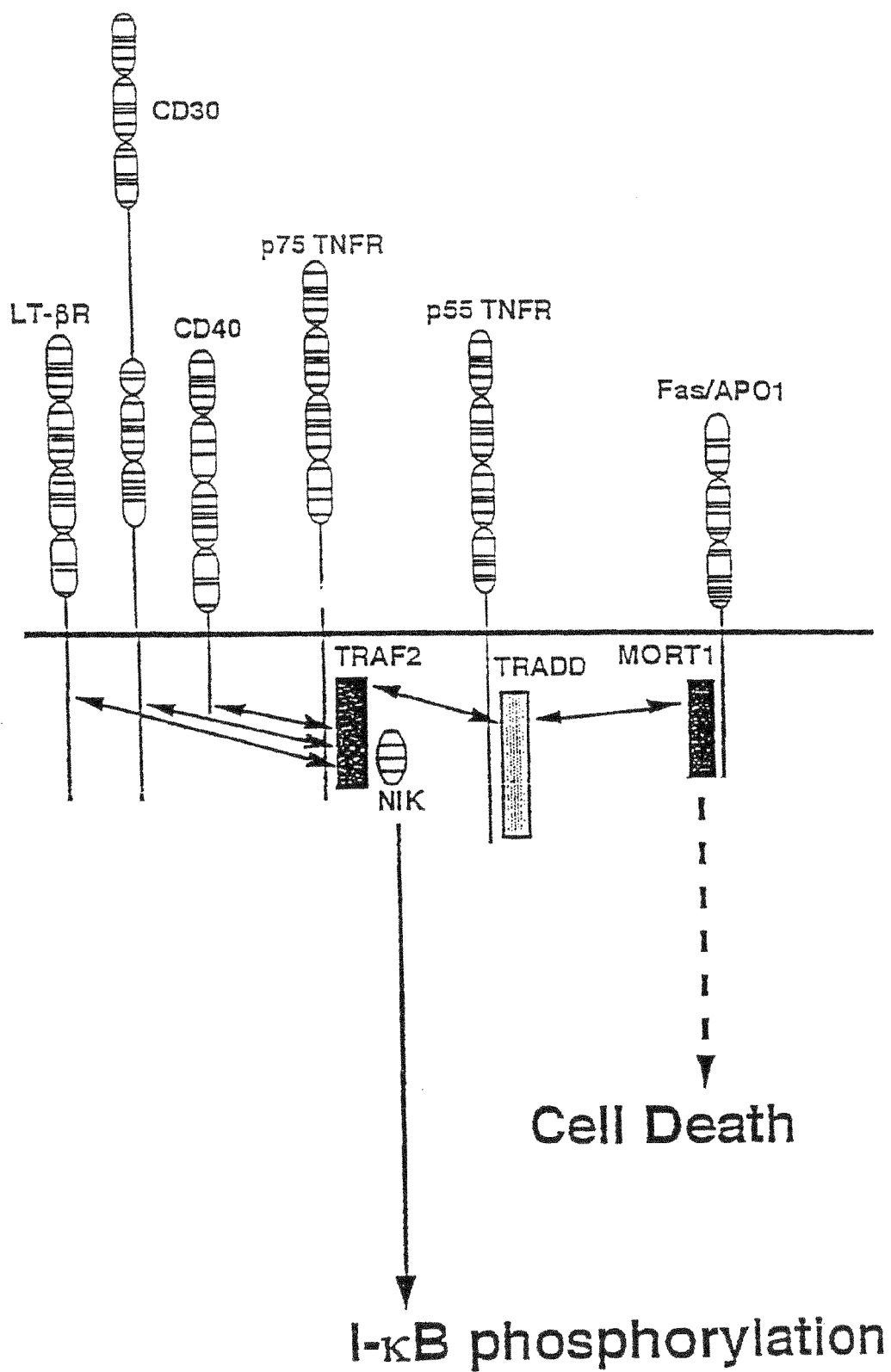
Figure 2B:
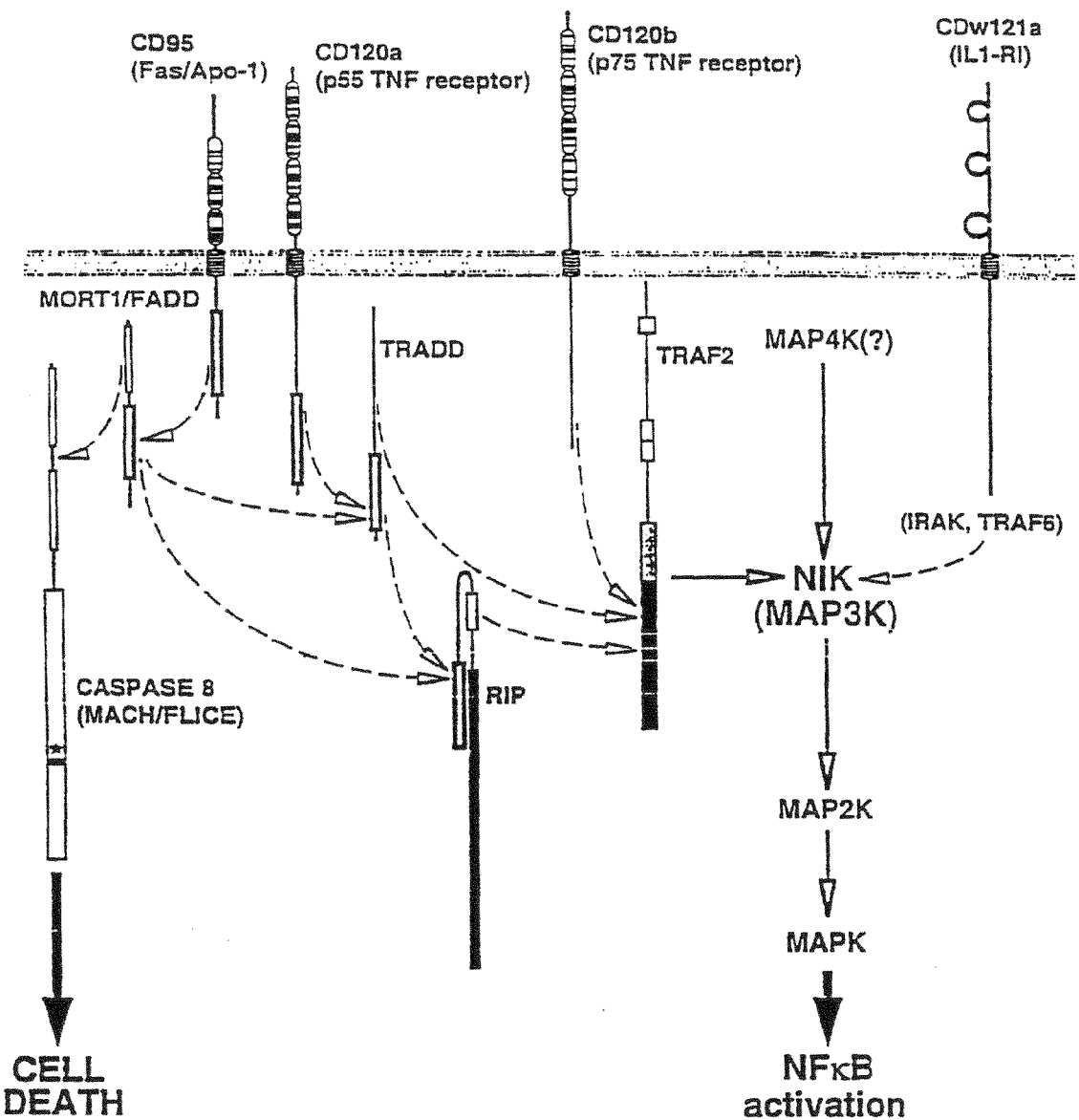

As regards TRAF2, it should be noted that several members of the TNF/NGF receptor family activate the transcription factor NF-κB by direct or indirect association with TRAF2, which is thus an adaptor protein for these receptors and may thus also be considered as a modulator/mediator of the induction of NF-κB activation activity of these TNF/NGF receptors (see the scheme in FIG. 2B). Another receptor, the IL-1 receptor activates NF-κB independently of TRAF2. One of the embodiments of a preferred TRAF2-binding protein in accordance with the present invention is the NIK protein, which binds NIK in a very specific way and stimulates NF-κB activity. NIK is a serine/threonine kinase having sequence similarity with several MAPKK kinases (see Examples below). NIK analogs or muteins produced in accordance with the present invention (see Examples) which lack the kinase activity of NIK fail to stimulate NF-κB activation, when these analogs/muteins are expressed in cells. Further, such NIK analogs/muteins when expressed in cells also block NF-κB induction by TNF as well as by other inducing agents such as the bacterial endotoxin LPS, forbol myristate acetate (a protein kinase C activator), and the HTLV-1 protein TAX. TNF induction of NF-κB activity is via either of the two TNF receptors (p55 and p75 TNF receptors) and hence it appears that the NIK mutein/analogs block induction of NF-κB activation via these receptors. Likewise, TNF and the FAS/APO1 receptor ligand may also induce NF-κB activity via a related receptor, the FAS/APO1 receptor, which induction is also blocked by NIK muteins/analogs. Moreover, the above receptors have adaptor proteins TRADD, RIP and MORT1 which can all also induce NF-κB activity, but which induction is also blocked by NIK muteins/analogs. In addition, such NIK muteins/analogs also blocked NF-κB induction by IL-1 (functioning via the IL-1 receptor). Accordingly, it arises that NIK participates in an NF-κB-inducing cascade that is common to receptors of the TNF/NGF family and to the IL-1 receptor. NIK also appears to act in a direct way in inducing NF-κB activation possibly by enhancing I-κB phosphorylation directly. This arises from the present observations that the above NIK analogs/muteins lacking kinase activity (also called dominant-negative mutants) when expressed in cells did not effect in any manner the TNF-induced activation of Jun kinase, indicating that NIK acts specifically to enhance phosphorylation of I-κB without affecting the MAP kinase involved in Jun phosphorylation.

Thus, the present invention concerns the DNA sequences encoding biologically active TRAF-binding proteins, e.g., TRAF2-binding proteins, such as, for example, NIK, as well as analogs, fragments and derivatives thereof, and the analogs, fragments and derivatives of the proteins encoded thereby. The preparation of such analogs, fragments and derivatives is by standard procedures (see for example, Sambrook et al., 1989) in which in the DNA encoding sequences, one or more codons may be deleted, added or substituted by another, to yield encoded analogs having at least a one amino acid residue change with respect to the native protein. Acceptable analogs are those which retain at least the capability of binding to TRAF2 with or without mediating any other binding or enzymatic activity, e.g., analogs which bind TRAF2 but do not signal, i.e., do not bind to a further downstream protein or other factor, or do not catalyze a signal-dependent reaction. In such a way analogs can be produced which have a so-called dominant-negative effect, namely, an analog which is defective either in binding to TRAF2, or in subsequent signaling following such binding as noted above. Such analogs can be used, for example, to inhibit the CD40, p55 TNF and p75 TNF (FAS/APO1 and other related receptor effects, as well as effected mediated by various receptor associated proteins (adaptors) as noted above, by competing with the natural TRAF2-binding proteins. Likewise, so-called dominant-positive analogs may be produced which would serve to enhance the TRAF2 effect. These would have the same or better TRAF2-binding properties and the same or better signaling properties of the natural TRAF2-binding proteins. In an analogous fashion, biologically active fragments of the clones of the invention may be prepared as noted above with respect to the preparation of the analogs. Suitable fragments of the DNA sequences of the invention are those which encode a protein or polypeptide retaining the TRAF2 binding capability or which can mediate any other binding or enzymatic activity as noted above. Accordingly, fragments of the encoded proteins of the invention can be prepared which have a dominant-negative or a dominant-positive effect as noted above with respect to the analogs. Similarly, derivatives may be prepared by standard modifications of the side groups of one or more amino acid residues of the proteins, their analogs or fragments, or by conjugation of the proteins, their analogs or fragments, to another molecule e.g., an antibody, enzyme, receptor, etc., as are well known in the art.

Of the above DNA sequences of the invention which encode a TRAF-binding protein, (e.g., TRAF2-binding protein, such as for example, NIK) isoform, analog, fragment or derivative, there is also included, as an embodiment of the invention, DNA sequences capable of hybridizing with a cDNA sequence derived from the coding region of a native TRAF-binding protein, in which such hybridization is performed under moderately stringent conditions, and which hybridizable DNA sequences encode a biologically active TRAF-binding protein. These hybridizable DNA sequences therefore include DNA sequences which have a relatively high homology to the native TRAF-binding proteins cDNA sequence, (e.g., TRAF2-binding protein cDNA sequence, such as, for example the NIK cDNA sequence) and as such represent TRAF-binding protein-like sequences which may be, for example, naturally-derived sequences encoding the various TRAF-binding protein isoforms, or naturally-occurring sequences encoding proteins belonging to a group of TRAF-binding protein-like sequences encoding a protein having the activity of TRAF-binding proteins (e.g., TRAF2-binding proteins, such as, for example, NIK). Further, these sequences may also, for example, include non-naturally-occurring, synthetically produced sequences, that are similar to the native TRAF-binding protein cDNA sequence but incorporate a number of desired modifications. Such synthetic sequences therefore include all of the possible sequences encoding analogs, fragments and derivatives of TRAF-binding proteins (e.g., TRAF2-binding proteins, such as, for example NIK), all of which have the activity of TRAF-binding proteins.

To obtain the various above noted naturally-occurring TRAF-binding protein-like sequences, standard procedures of screening and isolation of naturally-derived DNA or RNA samples from various tissues may be employed using the natural TRAF-binding protein cDNA or portion thereof as probe (see for example standard procedures set forth in Sambrook et al., 1989).

Likewise, to prepare the above noted various synthetic TRAF-binding protein-like sequences encoding analogs, fragments or derivatives of TRAF-binding proteins (e.g., TRAF2-binding proteins, such as, for example NIK), a number of standard procedures may be used as are detailed herein below concerning the preparation of such analogs, fragments and derivatives.

A polypeptide or protein "substantially corresponding" to TRAF-binding protein includes not only TRAF-binding protein but also polypeptides or proteins that are analogs of TRAF-binding protein.

Analogs that substantially correspond to TRAF-binding protein are those polypeptides in which one or more amino acid of the TRAF-binding protein's amino acid sequence has been replaced with another amino acid, deleted and/or inserted, provided that the resulting protein exhibits substantially the same or higher biological activity as the TRAF-binding protein to which it corresponds.

In order to substantially correspond to TRAF-binding protein, the changes in the sequence of TRAF-binding proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to TRAF-binding proteins, one such technique is the use of conventional mutagenesis techniques on the DNA encoding the protein, resulting in a few modifications. The proteins expressed by such clones can then be screened for their ability to bind to TRAF proteins (e.g., TRAF2) and to modulate TRAF protein (e.g., TRAF2) activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of TRAF-binding proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of TRAF-binding protein.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of TRAF-binding protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3-9 of Creighton, T. E., Proteins: Structure and Molecular Properties, W.H. Freeman & Co., San Francisco, Calif. 1983. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues: His, Arg, Lys;
4. Large aliphatic nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain and generally tends to promote β-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g., α-helix or β-sheet, as well as changes in biological activity, e.g., binding to TRAF proteins and/or mediation of TRAF proteins' effect on cell death.

Examples of production of amino acid substitutions in proteins which can be used for obtaining analogs of TRAF-binding proteins for use in the present invention include any known method steps, such as presented in U.S. Pat. RE 33,653, U.S. Pat. Nos. 4,959,314, 4,588,585 and 4,737,462, to Mark et al.; 5,116,943 to Koths et al., 4,965,195 to Namen et al.; 4,879,111 to Chong et al.; and 5,017,691 to Lee et al.; and lysine substituted proteins presented in U.S. Pat. No. 4,904,584 (Shaw et al.).

Besides conservative substitutions discussed above which would not significantly change the activity of TRAF-binding protein, either conservative substitutions or less conservative and more random changes, which lead to an increase in biological activity of the analogs of TRAF-binding proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

At the genetic level, these analogs are generally prepared by site-directed mutagenesis of nucleotides in the DNA encoding the TRAF-binding protein, thereby producing DNA encoding the analog, and thereafter synthesizing the DNA and expressing the polypeptide in recombinant cell culture. The analogs typically exhibit the same or increased qualitative biological activity as the naturally-occurring protein, Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preparation of a TRAF-Binding Protein in Accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a TRAF-binding protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., DNA 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phages are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated TRAF-binding protein sequence may be removed and placed in an appropriate vector, generally a transfer or expression vector of the type that may be employed for transfection of an appropriate host.

Accordingly, gene or nucleic acid encoding for a TRAF-binding protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding TRAF-binding protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al.; 5,142,033 to Innis; 5,122,464 to Wilson et al.; 5,091,310 to Innis; 5,066,584 to Gyllensten et al.; 4,889,818 to Gelfand et al.; 4,994,370 to Silver et al.; 4,766,067 to Biswas; 4,656,134 to Ringold; and Innis et al., eds., *PCR Protocols: A Guide to Method and Applications*) and RNA mediated amplification which uses anti-sense RNA to the target sequence as a template for double stranded DNA 5 synthesis (U.S. Pat. No. 5,130,238 Malek at al., with the trade name NASBA); and immuno-PCR which combines the use of DNA amplification with antibody labeling (Ruzicka et al., *Science* 260:487 (1993); Sano et al., *Science* 258:120 (1992); Sane et al., *Biotechniques* 9:1378 (1991)), the entire contents of which patents and reference are entirely incorporated herein by reference.

In an analogous fashion, biologically active fragments of TRAF-binding proteins (e.g., those of any of the TRAF2-binding proteins, such as, for example NIK) or its isoforms) may be prepared as noted above with respect to the analogs of TRAF-binding proteins. Suitable fragments of TRAF-binding proteins are those which retain the TRAF-binding protein capability and which can mediate the biological activity of TRAF proteins or other proteins associated with TRAF proteins directly or indirectly. Accordingly, TRAF-binding protein fragments can be prepared which have a dominant-negative or a dominant-positive effect as noted above with respect to the analogs. It should be noted that these fragments represent a special class of the analogs of the invention, namely, they are defined portions of TRAF-binding proteins derived from the full TRAF-binding protein sequence (e.g., from that of any one of the TRAF2-binding proteins, such as, for example NIK or its isoforms), each such portion or fragment having any of the above-noted desired activities. Such fragment may be, e.g., a peptide.

Similarly, derivatives may be prepared by standard modifications of the side groups of one or more amino acid residues of the TRAF-binding protein, its analogs or fragments, or by conjugation of the TRAF-binding protein, its analogs or fragments, to another molecule, e.g., an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as TRAF-binding proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

A TRAF-binding protein is a protein or polypeptide, i.e., a sequence of amino acid residues. A polypeptide consisting of a larger sequence which includes the entire sequence of a TRAF-binding protein, in accordance with the definitions herein, is intended to be included within the scope of such a polypeptide as long as the additions do not affect the basic and novel characteristics of the invention, i.e., if they either retain or increase the biological activity of TRAF-binding protein or can be cleaved to leave a protein or polypeptide having the biological activity of TRAF-binding protein. Thus, for example, the present invention is intended to include fusion proteins of TRAF-binding protein with other amino acids or peptides.

As mentioned above, it should be understood that the above 'TRAF-binding' proteins of the invention are any proteins which may bind and mediate/modulate the activity of any TRAF protein intracellularly. Particular examples are the TRAF2-binding proteins which can modulate or mediate the TRAF2-associated intracellular signaling activity, as mentioned above, especially as concerns TRAF2's involvement in inducing NF-κB activity, in particular, following the interaction between TRAF2 and various members of the TNF/NGF receptor family and/or their associated adaptor proteins as detailed above and below. A specific example of such TRAF2-binding proteins is the NIK protein and its various analogs, fragments, etc. (see Examples) which appears to bind TRAF2 very specifically and to have a direct action in inducing NF-κB activity, with various NIK dominant-negative analogs/muteins blocking this activity.

All the above mentioned modifications are in the scope of the invention provided they preserved the ability of the encoded proteins or polypeptides or their analogs and derivatives thereof, to bind at least the 222-501 amino acid sequence of TRAF2.

All the proteins and polypeptides of the invention by virtue of their capability to bind to TRAF2, are considered as mediators or modulators of TRAF2 signaling. As such, said molecules of the invention have a role in, for example, the signaling process in which the binding of TRAF2 ligand to CD30, CD40, lymphotoxin beta (LT-β) receptor, p55 or p75 TNF receptors, as well as the other receptors and adaptor proteins noted herein above, leads to activation of the transcription factor NF-κB. Particularly interesting is protein NIK and a partial NIK protein, encoded by clone 10 of the invention; a detailed sequence analysis of NIK and this clone-10-encoded protein (originally termed NMPI) disclosed encoded amino acid sequences corresponding to I-XI conserved motifs characteristic to Ser/Thr protein kinases, thus assigning a function to this protein.

The new clones proteins, their analogs, fragments and derivatives have a number of possible uses, for example:

Utility (i)

They may be used to mimic or enhance NF-κB activity, the function of TRAF2 and the receptors to which they bind, in situations where an enhanced function is desired such as in anti-tumor or immuno-stimulatory applications where the TRAF2-induced effects are desired. In this case the proteins of the invention, their analogs, fragments or derivatives, which enhance the TRAF2 or receptors effects, may be introduced to the cells by standard procedures known per se. For example, as the proteins encoded by the DNA clones of the invention are intracellular and they should be introduced only into the cells where the TRAF2 effect is desired, a system for specific introduction of these proteins into the cells is necessary. One way of doing this is by creating a recombinant animal virus e.g., one derived from Vaccinia, to the DNA of which the following two genes will be introduced: the gene encoding a ligand that binds to cell surface proteins specifically expressed by the cells, e.g., ones such as the AIDS (HIV) virus gp120 protein which binds specifically to some cells (CD4 lymphocytes and related leukemias) or any other ligand that binds specifically to cells carrying a receptor that binds TRAF2, such that the recombinant virus vector will be capable of binding such cells; and the gene encoding the proteins of the invention. Thus, expression of the cell-surface-binding protein on the surface of the virus will target the virus specifically to the tumor cell or other receptor-carrying cell, following which the proteins encoding sequences will be introduced into the cells via the virus, and once expressed in the cells will result in enhancement of the receptor or TRAF2 effect leading to a desired immuno-stimulatory effect in these cells. Construction of such recombinant animal virus is by standard procedures (see for example, Sambrook et al., 1989). Another possibility is to introduce the sequences of the encoded proteins in the form of oligonucleotides which can be absorbed by the cells and expressed therein.

Utility (ii)

They may be used to inhibit the NFκB activity, the effects of TRAF2 or of the receptor that binds it, e.g., in cases such as tissue damage as in AIDS, septic shock or graft-vs.-host rejection, in which it is desired to block the induced intracellular signaling. In this situation it is possible, for example, to introduce into the cells, by standard procedures, oligonucleotides having the anti-sense coding sequence for the proteins of the invention, which would effectively block the translation of mRNAs encoding the proteins and thereby block their expression and lead to the inhibition of the undesired effect. Alternatively, other oligonucleotides may be used; oligonucleotides that preserved their ability to bind to TRAF2 in a way that interferes with the binding of other molecules to this protein, while at the same time do not mediate any activation or modulation of this molecule. Having these characteristics, said molecules can disrupt the interaction of TRAF2 with its natural ligand, therefor acting as inhibitors capable of abolishing effects mediated by TRAF2, such as NF-κB activation, for example. Such oligonucleotides may be introduced into the cells using the above recombinant virus approach, the second sequence carried by the virus being the oligonucleotide sequence.

Another possibility is to use antibodies specific for the proteins of the invention to inhibit their intracellular signaling activity.

Yet another way of inhibiting the undesired effect is by the recently developed ribozyme approach. Ribozymes are catalytic RNA molecules that specifically cleave RNAs. Ribozymes may be engineered to cleave target RNAs of choice, e.g., the mRNAs encoding the proteins of the invention. Such ribozymes would have a sequence specific for the mRNA of the proteins and would be capable of interacting therewith (complementary binding) followed by cleavage of the mRNA, resulting in a decrease (or complete loss) in the expression of the proteins, the level of decreased expression being dependent upon the level of ribozyme expression in the target cell. To introduce ribozymes into the cells of choice (e.g., those carrying the TRAF2 binding proteins) any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993).

Utility (iii)

They may be used to isolate, identify and clone other proteins which are capable of binding to them, e.g., other proteins involved in the intracellular signaling process that are downstream of TRAF2. For example, the DNA sequences encoding the proteins of the invention may be used in the yeast two-hybrid system in which the encoded proteins will be used as "bait" to isolate, clone and identify from cDNA or genomic DNA libraries other sequences ("preys") encoding proteins which can bind to the clones proteins. In the same way, it may also be determined whether the proteins of the present invention can bind to other cellular proteins, e.g., other receptors of the TNF/NGF superfamily of receptors.

Utility (iv)

The encoded proteins, their analogs, fragments or derivatives may also be used to isolate, identify and clone other proteins of the same class i.e., those binding to TRAF2 or to functionally related proteins, and involved in the intracellular signaling process. In this application the above noted yeast two-hybrid system may be used, or there may be used a recently developed system employing non-stringent Southern hybridization followed by PCR cloning (Wilks et al., 1989).

Utility (v)

Yet another approach to utilize the encoded proteins of the invention, their analogs, fragments or derivatives is to use them in methods of affinity chromatography to isolate and identify other proteins or factors to which they are capable of binding, e.g., proteins related to TRAF2 or other proteins or factors involved in the intracellular signaling process. In this application, the proteins, their analogs, fragments or derivatives of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the proteins, their analogs, fragments or derivatives of the invention, can be eluted, isolated and characterized.

Utility (vi)

As noted above, the proteins, their analogs, fragments or derivatives of the invention may also be used as immunogens (antigens) to produce specific antibodies thereto. These antibodies may also be used for the purposes of purification of the proteins of the invention either from cell extracts or from transformed cell lines producing them, their analogs or fragments. Further, these antibodies may be used for diagnostic purposes for identifying disorders related to abnormal functioning of the receptor system in which they function, e.g., overactive or underactive TRAF2-induced cellular effects. Thus, should such disorders be related to a malfunctioning intracellular signaling system involving the proteins of the invention, such antibodies would serve as an important diagnostic tool. The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof, such as, for example, Fab and $F(ab')_2$-fragments lacking the Fc fragment of intact antibody, which are capable of binding antigen.

Utility (vii)

The antibodies, including fragments of antibodies, useful in the present invention may be used to quantitatively or qualitatively detect the clones of the invention in a sample, or to detect presence of cells which express the clones of the present invention. This can be accomplished by immunofluorescence techniques employing a fluorescently labeled antibody coupled with light microscopic, flow cytometric, or fluorometric detection.

The antibodies (or fragments thereof) useful in the present invention may be employed histologically, as in immunofluorescence or immunoelectron microscopy, for in situ detection of the clones of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the clones, but also its distribution on the examined tissue. Using the present invention, those of ordinary skill will readily perceive that any of wide variety of histological methods (such as staining procedures) can be modified in order to achieve such in situ detection.

Such assays for the clones of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capably of identifying the encoded proteins, and detecting the antibody by any of a number of techniques well known in the art.

Utility (viii)

The encoded proteins of the invention may also be used as indirect modulators of a number of other proteins by virtue of their capability of binding to other intracellular proteins, which other intracellular proteins directly bind yet other intracellular proteins or an intracellular domain of a transmembrane protein.

For the purposes of modulating these other intracellular proteins or the intracellular domains of transmembranal proteins, the proteins of the invention may be introduced into cells in a number of ways as mentioned hereinabove in (ii).

It should also be noted that the isolation, identification and characterization of the proteins of the invention may be performed using any of the well known standard screening procedures. For example, one of these screening procedures, the yeast two-hybrid procedure which was used to identify the proteins of the invention. Likewise other procedures may be employed such as affinity chromatography, DNA hybridization procedures, etc. as are well known in the art, to isolate, identify and characterize the proteins of the invention or to isolate, identify and characterize additional proteins, factors, receptors, etc. which are capable of binding to the proteins of the invention.

Moreover, the proteins found to bind to the proteins of the invention may themselves be employed, in an analogous fashion to the way in which the proteins of the invention were used as noted above and below, to isolate, identify and characterize other proteins, factors, etc. which are capable of binding to the proteins of the invention-binding proteins and which may represent factors involved further downstream in the associated signaling process, or which may have signaling activities of their and hence would represent proteins involved in a distinct signaling process.

The DNA sequences and the encoded proteins of the invention may be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins are the derivatives produced by standard modification of the proteins or their analogs or fragments, produced by the transformed hosts.

The present invention also relates to pharmaceutical compositions for modulation of the effects mediated by TRAF2. The pharmaceutical compositions comprising, as an active ingredient, any one or more of the following: (i) one or more of the DNA sequences of the invention, or parts of them, subcloned into an appropriate expression vector; (ii) a protein according to the invention, its biologically active fragments, analogs, derivatives or a mixture thereof; (iii) a recombinant animal virus vector encoding for a protein according to the invention, its biologically active fragments, analogs or derivatives.

The pharmaceutical compositions are applied according to the disease to be treated and in amounts beneficial to the patent, depending on body weight and other considerations, as determined by the physician.

As noted above, one of the specific embodiments of the TRAF-binding proteins of the present invention is the TRAF2-binding protein NIK. Based on the findings in accordance with the present invention that NIK binds specifically to TRAF2 and as such is a mediator/modulator of TRAF2 and can thus mediate/modulate TRAF2's activity in NF-κB activation and hence its possible role in cell survival pathways in ways that TRAF2 functions independently or in conjunction with other proteins (e.g., p55 TNF and p75 TNF receptors, FAS/APO1 receptor, MORT-1, RIP and TRADD) it is of importance to design drugs which may enhance or inhibit the TRAF2-NIK interaction, as desired. For example, when it is desired to increase the cell cytotoxicity induced by TNF it would be desired to inhibit NF-κB induction, by inhibiting the TRAF2-NIK interaction or by inhibiting TRAF2 and/or NIK specifically. Likewise, for example, when it is desired to inhibit the cell cytotoxicity induced by TNF it would be desired to enhance NF-κB induction by enhancing the TRAF2-NIK interaction or by enhancing TRAF2- and/or NIK-specific NF-κB induction. There are many diseases in which such drugs can be of great help. Amongst others, (see above discussion as well) acute hepatitis in which the acute damage to the liver seems to reflect FAS/APO1 receptor-mediated death of the liver cells following induction by the Fas ligand; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

In such cases, it would be desired to inhibit the FAS/APO1 receptor-mediated cell cytotoxicity (apoptosis) pathway and enhance the FAS/APO1 receptor-mediated induction of NF-κB via TRAF2 and the TRAF2-NIK interaction. One way of doing this would be to increase the amount of NIK in the cells or to increase the amount of TRAF2 and NIK so that the NIK- or TRAF2-NIK-mediated induction of NF-κB activation will be increased providing higher levels of NF-κB activation and hence cell survival; or so that the direct or indirect interaction between FAS/APO1 receptor and TRAF2 (or TRAF2-NIK) will be increased resulting in a decrease in FAS/APO1 receptor interactions with cell cytotoxic mediators (e.g., MACH, see scheme in FIG. 2B) to provide for an increase in the induction of NF-κB activation and cell survival.

Conversely, in the case of, for example, tumors and infected cells (see also discussion above) it would be desired to increase the FAS/APO1 receptor-mediated cell cytotoxicity to bring about increased cell death. In this case it would be desired to inhibit FAS/APO1 receptor-TRAF2 (or -TRAF2-NIK) interactions and/or to inhibit NIK directly, and thereby to decrease the induction of NF-κB activity.

It is possible that NIK or one or more of its possible isoforms, analogs or fragments may serve as "natural" inhibitors of NIK itself or of the NIK-TRAF2 interaction, and as such serve as inhibitors of the induction of NF-κB activation. Such inhibitors may thus be employed as the specific inhibitors noted above, for example, those inhibitors to be used when it is desired to increase the cell cytotoxic effects of TNF or the ligand of the FAS/APO1 receptor in order to increase cell death. In fact, as exemplified herein below, various NIK analogs and muteins have been isolated in accordance with the present invention, which are kinase-deficient analogs/muteins and which are capable of blocking the induction of NF-κB activation mediated by the TNF receptors, the FAS/APO1 receptor, their associated proteins TRADD, RIP and MORT1; as well as mediated by the IL-1 receptor (which activation is via NIK but independent of TRAF2); and also as mediated by bacterial endotoxin (LPS), forbol myristate acetate, and the HTLV-1 protein TAX. Likewise, other substances such as peptides, organic compounds, antibodies, etc. may also be screened to obtain specific drugs which are capable of inhibiting the TRAF2-NIK interaction or the activity of NIK.

In a similar fashion, when it is desired to increase the NF-κB activation in various situations as noted above it is possible, for example, to increase the amount of NIK and/or TRAF2 in cells by various standard methods noted herein above (e.g., introducing DNA encoding NIK and/or TRAF2 into cells to induce increased expression, or preparing suitable formulations containing NIK and/or TRAF2 for direct introduction into cells, or any other way known to those of skill in the art). Likewise, other substances such as peptides, organic compounds, etc. may also be screened to obtain specific drugs which are capable of enhancing the activity of NIK or of enhancing the TRAF2-NIK interaction.

A non-limiting example of how peptide inhibitors of the NIK-TRAF2 interaction would be designed and screened is based on previous studies on peptide inhibitors of ICE or ICE-like proteases, the substrate specificity of ICE and strategies for epitope analysis using peptide synthesis. The minimum requirement for efficient cleavage of a peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thornberry et al., 1992). Furthermore, the fluorogenic substrate peptide (a tetrapeptide), acetyl-Asp-Glu-Val-Asp-a-(4-methyl-coumaryl-7-amide) (SEQ ID NO:21) abbreviated Ac-DEVD-AMC, corresponds to a sequence in poly (ADP-ribose) polymerase (PARP) found to be cleaved in cells shortly after FAS-R stimulation, as well as other apoptotic processes (Kaufmann, 1989; Kaufmann et al., 1993; Lazebnik et al., 1994), and is cleaved effectively by CPP32 (a member of the CED3/ICE protease family) and MACH proteases.

As Asp in the $P_1$ position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling, etc. This method of Geysen's was shown to be capable of testing at least 4000 peptides each working day.

In a similar way the exact binding region or region of homology which determines the interaction between TRAF2 and NIK (or any other TRAF protein and TRAF-binding protein) can be elucidated and then peptides may be screened which can serve to block this interaction, e.g., peptides synthesized having a sequence similar to that of the binding region or complementary thereto which can compete with natural NIK (or TRAF-binding protein) for binding to TRAF2 (or TRAF).

Since it may be advantageous to design peptide inhibitors that selectively inhibit TRAF2-NIK (or TRAF-TRAF binding protein) interactions without interfering with physiological cell death processes in which other members of the intracellular signaling pathway are involved, e.g., MACH proteases of the cell death pathway, which are members of the CED3/ICE family of proteases, the pool of peptides binding to TRAF2 (or TRAF) or NIK (or TRAF-binding proteins) in an assay such as the one described above can be further synthesized as a fluorogenic substrate peptide to test for selective binding to such other proteins to select only those specific for TRAF2/NIK (or TRAF/TRAF-binding protein). Peptides which are determined to be specific for, for example, TRAF2/NIK, can then be modified to enhance cell permeability and inhibit the activity of TRAF2 and/or NIK either reversibly or irreversibly. Thornberry et al. (1994) reported that a tetrapeptide (acyloxy) methyl ketone Ac-Tyr-Val-Ala-Asp-$CH_2OC$ (O)-[2,6-$(CF_3)_2$] Ph (SEQ ID NO:22) was a potent inactivator of ICE. Similarly, Milligan et al. (1995) reported that tetrapeptide inhibitors having a chloromethylketone (irreversibly) or aldehyde (reversibly) groups inhibited ICE. In addition, a benzyloxycarboxyl-Asp-$CH_2OC$ (O)-2,6-dichlorobenzene (DCB) was shown to inhibit ICE (Mashima et al., 1995). Accordingly, in an analogous way, tetrapeptides that selectively bind to, for example, TRAF2 or NIK, can be modified with, for example, an aldehyde group, chloromethylketone, (acyloxy) methyl ketone or a $CH_2OC$ (O)-DCB group to create a peptide inhibitor of TRAF2/NIK activity. Further, to improve permeability, peptides can be, for example, chemically modified or derivatized to enhance their permeability across the cell membrane and facilitate the transport of such peptides through the membrane and into the cytoplasm. Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the activity of, for example, NIK by inhibiting the NIK-TRAF2 interaction and likewise, the interaction between TRAF proteins and TRAF-binding proteins can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g., myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), α-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al., 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of the TRAF-TRAF-binding protein interaction, for example, the TRAF2-NIK interaction according to the present invention is meant to include peptidomimetic drugs or inhibitors, which can also be rapidly screened for binding to, for example TRAF2/NIK to design perhaps more stable inhibitors.

It will also be appreciated that the same means for facilitating or enhancing the transport of peptide inhibitors across cell membranes as discussed above are also applicable to the TRAF-binding proteins, for example, NIK, its analogs, fragments or its isoforms themselves as well as other peptides and proteins which exert their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, Nature, 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273-3277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., J. Immunol. 137:1066-1074 (1986); Robinson et al., International Patent Application No. WO8702671 (published May 7, 1987); Liu et al., Proc. Natl. Acad. Sci. USA 84:3439-3443 (1987); Sun et al., Proc. Natl. Acad. Sci. USA 84:214-218 (1987); Better et al., Science 240:1041-1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the TRAF-binding proteins, analogs, fragments or derivatives thereof, (e.g., NIK, its isoforms, analogs, fragments or derivatives) of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above TRAF-binding protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., J. Nucl. Med. 24:316-325 (1983)).

It will be appreciated that Fab and F(ab')2 and other fragments of the antibodies useful in the present invention may be used for the detection and quantitation of the TRAF-binding protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the TRAF-binding protein (e.g., NIK) in a sample or to detect presence of cells which express the TRAF-binding protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the TRAF-binding protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the TRAF-binding protein, but also its distribution on the examined tissue. Using the present invention, those of ordinary skill will readily perceive that any of wide variety of histological methods (such as staining procedures) can be modified in order to achieve such in situ detection.

Such assays for the TRAF-binding protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the TRAF-binding protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

As mentioned above, the present invention also relates to pharmaceutical compositions comprising recombinant animal virus vectors encoding the TRAF-binding proteins, which vector also encodes a virus surface protein capable of binding specific target cell (e.g., cancer cells) surface proteins to direct the insertion of the TRAF-binding protein sequences into the cells. Further pharmaceutical compositions of the invention comprises as the active ingredient (a) an oligonucleotide sequence encoding an anti-sense sequence of the TRAF-binding protein sequence, or (b) drugs that block the TRAF-binding protein-TRAF interaction.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as are well known to those of skill in the art.

The TRAF-binding protein and its isoforms or isotypes are suspected to be expressed in different tissues at markedly different levels and apparently also with different patterns of isotypes in an analogous fashion to the expression of various other proteins involved in the intracellular signaling pathways as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. The wide heterogeneity of MACH isoforms, which greatly exceeds that observed for any of the other proteases of the CED3/ICE family, should allow a particularly fine tuning of the function of the active MACH isoforms.

In accordance with the present invention there have also been isolated analogs/muteins of one of the TRAF-binding proteins, namely of the TRAF2-binding protein NIK. These NIK analogs/muteins (see above and see Examples below) are inhibitory to NIK-mediated as well as inhibitory to the induction of NF-κB activation mediated by the TNF receptors, FAS/APO1 receptor, their related proteins, the IL-1 receptor and other agents. Hence, as noted above, the TRAF-binding proteins or possible isoforms may have varying effects in different tissues as regards their interaction with TRAF proteins and their influence thereby on the activity of the TRAF proteins, or intracellular signaling mediated by the TRAF proteins.

It is also possible that some of the possible TRAF-binding protein isoforms serve other functions. For example, NIK or some NIK analogs, or isoforms may also act as docking sites for molecules that are involved in other, non-cytotoxic effects of, for example, Fas/APO1 and TNF receptors via interaction with TRAF2 or even independently of TRAF2.

Due to the unique ability of Fas/APO1 and TNF receptors to cause cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. In view of the suspected important role of TRAF proteins, e.g., TRAF2 and hence the TRAF-TRAF-binding protein, e.g., TRAF2-NIK interaction in Fas/APO1- and TNF-mediated NF-κB activation, it seems particularly important to design drugs that can block the TRAF-TRAF binding protein interaction, e.g., TRAF2-NIK interaction when it is desired to kill cells (by inhibiting NF-κB activation), and conversely, when it is desired to preserve cells this interaction should be enhanced (to enhance NF-κB activation).

The present invention also concerns proteins or other ligands which can bind to the TRAF-binding proteins of the invention and thereby modulate/mediate the activity of the TRAF-binding proteins. Such proteins or ligands may be screened, isolated and produced by any of the above mentioned methods. For example, there may be isolated a number of new ligands, including proteins, capable of binding to the NIK proteins of the invention (such new proteins/ligands excluding the known TRAF2 and possibly IκB if NIK actually binds I-κB).

As detailed above, such new TRAF-binding protein-binding proteins/ligands, e.g., NIK-binding proteins, may serve as, for example, inhibitors or enhancers of NIK-mediated activity or the activity mediated by the, for example, TRAF2-NIK interaction, and as such will have important roles in various pathological and other situations as detailed above. Another function of such TRAF-binding protein-binding proteins/ligands would be to serve as specific agents for the purification of the TRAF-binding proteins by, for example, affinity chromatography, these new binding proteins/ligands being attached to the suitable chromatography matrices to form the solid or affinity support/matrix through which a solution, extract or the like, containing the TRAF-binding proteins, e.g., NIK, will be passed and in this way to facilitate the purification thereof. Such methods of affinity chromatography are now well known and generally standard procedures of the art.

Likewise, all of the above mentioned TRAF-binding proteins, analogs, fragments, isoforms and derivatives of the present invention may be used to purify by affinity chromatography the various TRAF proteins to which they bind. For example, TRAF2-binding proteins like NIK, and analogs, fragments and muteins of NIK (see examples below) may be used for the affinity chromatography purification of TRAF2. Hence in the same way as the NIK protein, analogs/muteins of the present invention were isolated and produced (see Examples below) using these methods and any other equivalent methods readily apparent to those of skill in the art (as detailed herein above), any other TRAF2-binding proteins may be identified and produced. Such a method for identifying and producing these TRAF-binding proteins, e.g., TRAF2-binding proteins will include a screening step in which the TRAF (e.g., TRAF2) protein, or at least a specific portion thereof (e.g., the portion of TRAF2 between a.a. 222-501) is used as a substrate or 'bait' to obtain proteins or any other ligand capable of binding thereto; followed by steps of identifying and characterizing such proteins/ligands so-obtained; and subsequently producing such proteins/ligands in substantially isolated and purified forms. All these steps are well known to those of skill in the art and are detailed herein above and herein below.

The invention will now be described in more detail in the following non-limiting examples and the accompanying drawings.

It should also be noted that the procedures of: i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, as well as other procedures used in the following Examples have been detailed in previous publications by the present inventors in respect of other intracellular signaling proteins and pathways (see, for example, Boldin et al., 1995a, 1995b, and Boldin et al. 1996). These procedures also appear in detail in the co-owned co-pending Israel Application Nos. 114615, 114986, 115319, 116588, 117932, and 120367 as well as the corresponding PCT application No. PCT/US96/10521). Accordingly, the full disclosures of all these publications and patent applications are included herein in their entirety and at least as far as the detailed experimental procedures are concerned.

EXAMPLES

Materials and Methods cDNA Libraries

B-cell cDNA library: Oligo dT primed library constructed from human B cells was used (Durfee et al., 1993). The cDNAs of the library were inserted into the XhoI site of the pACT based vector pSE1107 in fusion with GAL4 activation domain.

λgt10 testis cDNA library: A cDNA library from human testis was used. The library is a random hexanucleotide primed library with an average insert size of 200 to 400 bp.

Yeast Strains

Two yeast stains were used as host strains for transformation and screening: HF7c strain that was used in the two hybrid screen and SFY526 strain that was used in the b-galactosidase assays. Both strains carry the auxotrophic markers trp1 and leu2, namely these yeast strains cannot grow in minimal synthetic medium lacking tryptophan and leucine, unless they are transformed by a plasmid carrying the wild-type versions of these genes (TRP1, LEU2). The two yeast strains carry deletion mutations in their GAL4 and GAL80 genes (gal4-542 and gal80-538 mutations, respectively).

SFY526 and HF7c stains carry the lacZ reporter in their genotypes; in SFY526 strain fused to the UAS and the TATA portion of GALL promoter, and in HF7c three copies of the GAL4 17-mer consensus sequence and the TATA portion of the CYC1 promoter are fused to lacZ. Both GALL UAS and the GAL4 17-mers are responsive to the GAL4 transcriptional activator. In addition, HF7c strain carries the HIS3 reporter fused to the UAS and the TATA portion of GALL promoter.

Cloning of Human TRAF2

The human TRAF2 (SEQ ID NO:23) was cloned by PCR from an HL60 cDNA library (for TRAF2 sequence and other details see Rothe et al., 1994; Rothe et al., 1995a; Cheng et al., 1996; Hsu et al., 1996; and Wallach, 1996). The primers used were: a) 30-mer forward primer CAGGATCCTC ATGGCTGCAGCTAGCGTGAC (SEQ ID NO:8) corresponding to the coding sequence of hTRAF2 starting from the codon for the first methionine (underlined) and including a linker with BamHI site. b) 32-mer reverse primer GGTCGAC TTAGAGCCCTGTCAGGTCCACAATG (SEQ ID NO:9) that includes hTRAF2 gene stop codon (underlined) and a SalI restriction site in its linker. PCR program comprised of an initial denaturation step 2 min. at 94° C. followed by 30 cycles of 1 min. at 94° C., 1 min. at 64° C., 1 min. and 40 sec. at 72° C. The amplified human TRAF2 was then inserted into the BamHI-SalI sites of pGBT9 vector in conjunction with GAL 4 DNA Binding domain.

Two Hybrid Screen of B-Cell Library

The two hybrid screen is a technique (see details in above mentioned publications and patent applications) used in order to identify factors that are associated with a particular molecule that serves as a "bait". In the present invention TRAF2 that was cloned into the vector pGBT9, served as the bait. TRAF2 was co-expressed together with the screened B-cell cDNA library in the yeast strain HF7c. The PCR-cloned TRAF2 was a recombinant fusion with the CAL4 DNA-binding domain and the screened cDNA library was fused to the GAL4 activation domain in the pSE1107 vector. The reporter gene in HF7c was HIS3 fused to the upstream activating sequence (UAS) of the GALL promoter which is responsive to GAL4 transcriptional activator. Transformants that contained both pGBT9 and pSE1107 plasmids were selected for growth on plates without tryptophan and leucine. In a second step positive clones which expressed two hybrid proteins that interact with each other, and therefore activated GAL1-HIS3, were picked up from plates devoided of tryptophan, leucine and histidine and contained 50 mM 3-aminotriazol (3AT).

β-Galactosidase Assay

Positive clones picked up in the two hybrid screen were subjected to lacZ color development test in SFY526 yeast cells, following Clontech Laboratories' manual (for details see above mentioned publications and patent applications). In brief, transformants were allowed to grow at 30° C. for 2-4 days until reaching about 2 mm in diameter, then were transferred onto Whatman filters. The filters went through a freeze/thaw treatment in order to permeabilize the cells, then soaked in a buffer (16.1 mg/ml $Na_2HPO_4.7H_2O$; 5.5 mg/ml $NaH_2PO_4.H_2O$; 0.75 mg/ml KCl; 0.75 mg/ml $MgSO_4.7H_2O$, pH=7) containing 0.33 mg/ml X-gal and 0.35 mM β-mercaptoethanol. Colonies were monitored for development of blue color which is an indication for induction of β-galactosidase.

Expression of Cloned cDNAs

Two kinds of expression vectors were constructed:
a) A pUHD10-3 based vectors containing the open reading frame (ORF) of either clone 9, 10 or 15 in fusion with the Hemeaglutinine (HA) epitope.
b) A pUHD10-3 based vector into which FLAG octapeptide sequence was introduced just in front of cloned TRAF2, hereby named FLAG/B6/TRAF2.

The constructs containing an ORF of clone 9, 10 or 15 were transfected into HeLa-Bujard cells (for these cells see Gossen, M. and Bujard, M. (1992)) either alone or cotransfected with FLAG/B6/TRAF2 using standard calcium-phosphate method (Method in, for example, Current Protocols in Molecular Biology, eds. Ausubel, F. M et al.)

Luciferase Assay

Typically $5 \times 10^5$ transfected cells were harvested by washing three times with cold PBS and resuspending in 400 µl extraction buffer (0.1 M $K_2HPO_4/KH_2PO_4$ pH=7.8; 1 mM DTT). Lysis of the cells was achieved by three times freezing in liquid nitrogen and thawing. Cell debris was removed by centrifugation (5 min. at 10,000×g). For the luciferase assay, 200 µl of luciferase buffer (25 mM glycylglycine, 15 mM $K_2HPO_4/KH_2PO_4$ pH=7.8, 15 mM $MgSO_4$, 4 mM EGTA, 2 mM ATP, 1 mM DTT) were added to 50 µl of the lysate. Subsequently, 100 µl of 0.2 mM D-luciferine, 25 mM glycylglycine, 1 mM DTT were added to the reaction. Luciferase activity was determined by reading light emission using a Lumitron luminometer set on 10 seconds integration (see above publications and patent applications for additional details).

Example 1

Cloning of New Clones 9, 10 and 15

A cDNA library prepared from B-cells was screened for proteins that associate with TRAF2, using the two hybrid technique as described in Materials and Methods (iv). Only in transformants that expressed both TRAF2 and a protein capable of interacting with it, the GAL4 DNA-binding domain and the transcriptional activation domain were brought together. The result was the activation and expression of the reporter gene, in this case HIS3 fused to the UAS and the TATA portion of the GALL promoter.

The screen yielded approximately 2000 clones which were able to grow on Trp-, Leu-, His-3AT plates. DNA prepared from 165 randomly selected positive clones served for transient co-transfection of SFY526 yeast strain together with TRAF2 cloned into pGBT9 vector. Assay for β-galactosidase activity was performed on the transformed SFY526 yeast colonies as described in Materials and Methods (v). The blue color that developed was an indication for yeast colonies that contain cDNA encoding a protein or polypeptide that binds to TRAF2.

The results of the two hybrid screen; the ability of the picked clones to grow on 3AT plates and to induce LacZ as measured in the color test, are summarized in Table II. Of the positive clones checked, two were cDNAs coding for known proteins; TRAF2 itself that is capable of self-associating and forming homodimers, and the lymphotoxin beta receptor whose intracellular domains were shown to bind TRAF2. Three of the cloned cDNAs (clones 9, 10 and 15) were novel.

The positive clones were further checked in a binding specificity test, namely checked for their interaction with irrelevant baits. As shown in Table III, clones 9 and 10 reacted only with TRAF2 and did not bind to any one of a number of irrelevant proteins checked. Clone 15, on the other hand, did not bind to MORT1, nor to the intercellular domains of the p55 and p75 TNF receptors, but did weakly bind to Lamin and to Cycline D.

In order to narrow down the region on TRAF2 molecule which interact with clones 9, 10 and 15, two additional constructs were made. One construct comprised of the N-terminal part of the TRAF2 molecule, amino-acids 1 to 221, that included the Ring finger and the zinc finger motifs. The second construct included only the C-terminal part of the molecule, amino acids 222 to 501, covering the "TRAF-domain" and additional 42 amino acids. These two constructs were served as baits in two hybrid tests. The results clearly show that while clones 9, 10 and 15 did not interact with the construct comprising amino acids 1 to 221 of TRAF2 molecule, they all did bind to the C-terminal construct comprising the "TRAF domain" with the same efficiency as they bound to the full length TRAF2 molecule.

TABLE II

Summary of the results of the two hybrid screen using TRAF2 as a "bait", in which clones 9, 10 and 15 were picked up

| Growth on 50 mM 3AT | Color test (min.) | ID/name of clone, as defined by its sequencing | Number of independent clones |
|---|---|---|---|
| +++ | 10 min | TRAF2 | 150 |
| ++ | 20 min | new clone number 9 | 6 |
| +++ | 15 min | new clone number 10 | 2 |
| ++++ | 10 min | Lymphotoxin beta receptor | 2 |
| + | 15 min | new clone number 15 | 5 |

TABLE III

Specificity tests (interaction with irrelevant baits in the two-hybrid test)

| clone: | clone 9 | clone 10 | clone 15 |
|---|---|---|---|
| bait |  |  |  |
| LAMIN | − | − | − |
| cyclin D | − | − | − |
| p75-IC | − | − | − |
| p55-IC | − | − | − |
| MORT1 | − | − | − |
| TRAF2 | +++ | +++ | +++ |

Applying several PCR steps to cDNA clone 10, the full length cDNA was cloned from cDNA libraries obtained from RNA of human tissues. This protein was designated NIK for 'NF-κB inducing kinase' due to the fact that it contains a protein-kinase region (see below). It should be noted that the sequence of clone 10, when initially analyzed (before the obtention of NIK by PCR) was seen to encode for a protein, originally designated NMPI (see co-owned, co-pending IL 117800). This NMPI or clone 10 encoded protein was seen to have sequences corresponding to the I to XI conserved motifs that characterize Ser/Thr protein kinases.

Example 2

Sequencing of New Clones

Three of the novel cDNA clones (clones 9, 10 and 15) were purified, amplified in *E. Coli* and their DNA was subject to sequence analysis. All three clones were found to be partial cDNA clones.

The total lengths of clones 9, 10 and 15 were around 2000, 2700 and 1300 base pairs, respectively.

FIGS. 3A-C and 5A show the sequenced part of clones 9 and 15 and FIGS. 4A-B show the full sequence of clone 10.

FIGS. 5A-B show the entire nucleotide sequence of clone 15 sequenced from both 5' and 3' ends (FIG. 5A) and the deduced amino acids encoded thereby (FIG. 5B). Clone 15, which is a partial cDNA clone, was found to encode a 172 amino acid long protein.

Clones 9 and 15 are partial clones, which lack their most 5' end of the coding DNA sequences. The deduced amino acid sequences shown in FIGS. 3B, 4B and 5B, are all started from the first nucleotide of the respective clone.

The sequence of clone 10 (a partial cDNA clone) which was most thoroughly analyzed, encodes for a protein called NMP1 as noted above, containing Ser/Thr protein kinase motifs. The full length cDNA clone obtained from PCR using the clone 10 as noted above revealed the new TRAF2-binding kinase NIK as mentioned above.

The full nucleotide sequence and its deduced amino acid sequence of NIK are shown in FIGS. 6A-G in which the initiator ATG at nucleotide no. 232 is underlined, and in which the stop codon at nucleotide no. 3073 is indicated by a star. The fully sequenced NIK clone of FIGS. 6A-G is 4596 nucleotides in length within which the NIK coding sequence is contained, this coding for a NIK protein of 947 amino acid residues.

Databank searches revealed that the new amino acid sequence of NIK shows particularly high homology to a group of kinases of which several are known to serve as MAP kinase kinase kinase.

FIGS. 7A-BB show the alignment of:
mouse MEKK (s1),
BYR2 (s2),
Tpl-2 (s3),
Ewing's sarcoma oncogene (s4),
SSC3 (s5),
(STE11) (s6),
(NPK1) (s7),
(BCK1) (s8), and
(NIK) (s9).

Some of those kinases have been identified by virtue of oncogene activity that they possess when in mutated form.

Example 3

Expression of Cloned cDNAs and their Co-Immunoprecipitation with TRAF2

HeLa-Bujard cells were transfected with TRAF2 tagged with FLAG in pUHD10-3 based expression vector and constructs containing ORF of either clone 9, 10 or 15 fused to HA epitope, as described in Materials and Methods (iv). Cells were then grown for 24 hrs. in Dulbecco's Modified Eagle's Medium (DMEM) plus 10% calf serum with added $^{35}$S-Methionine and $^{35}$S-Cysteine. At the end of that incubation time cells were lysed in radioimmune precipitation buffer (10 mM Tris-HCl, pH 7.5, 150 mM NaCl, 1% Nonident P-40, 1% deoxycholate, 0.1% SDS, and 1 mM EDTA; 1 ml/5×10$^5$ cells), and the lysate was precleared by incubation with irrelevant rabbit antiserum and Protein G-Sepharose beads (Pharmacia, Sweden). Immunoprecipitation was performed by 1 hour incubation at 4° C. of aliquots of the lysate with anti-FLAG (purchased from Eastman Kodak Co.) or anti-HA (clone 12CA5 (Field, J. et al. (1988)) monoclonal antibodies. The expressed proteins were analyzed on SDS-PAGE gel followed by autoradiography.

The results of such experiments demonstrated that the partial cDNA clones 9, 10 and 15 encoded proteins of molecular weights around 50-65, 45 and 26 kDa respectively.

No interaction of clone 15 with TRAF2 could be detected, but the proteins encoded by clones 9 and 10 (NIK) as well as the full length NIK, were co-immunoprecipitated with the TRAF2 protein. Samples of cells that were co-transfected with TRAF2 and either one of these two clones and immunoprecipitated with either anti-FLAG or anti-HA antibodies followed by analysis on SDS-PAGE as described above, displayed three bands in each lane; one band corresponding to either clone 9 or 10 encoded proteins and the other two is a doublet of 42 and 44 kDa corresponding to TRAF2 protein.

Example 4

Functional Tests

NIK was found to have NF-κB induction by gel retardation assay. Typically 0.5-1×10$^6$ 293 EBNA cells were transfected with either 10 μg of clone 10 in pcDNA3, 3 μg of pcDNA3 containing cDNA for the p75 TNF receptor, or with both clone 10 (10 μg) and p75 TNF receptor (3 μg). In each one of the transfections the total amount of transfected DNA was brought to 15 μg with the "empty" pcDNA3 vector. As a control serve 293 EBNA cells transfected with 15 μg pcDNA3 vector alone. Cells were grown for 24 hrs in DMEM medium+10% calf serum, then were harvested and treated according to Schreiber et al. (Schreiber, E. et al. (1989). Samples were run on 5% polyacrylamide gel. NF-κB was monitored using a set of $^{32}$P_radiolabelled oligonucleotides corresponding to the NF-κB binding site as probes. (The probes were GATGCCATTGGGGATTTCCTCTTT (SEQ ID NO:10) and CAGTAAAGAGGAAATCCCCAATGG (SEQ ID NO:11)).

As shown in Table IV NIK induced NF-κB even more effectively than TRAF-2. On the other hand, clone 10 did not have this effect at all.

Reporter gene assay was performed as follows:
293 EBNA cells were co-transfected with the pcDNA3 vector containing HIV LTR linked to the luciferase reporter gene, together with either pcDNA3 plasmid containing cDNA for the p75 TNF receptor alone, pcDNA3 plasmid containing clone 10 cDNA alone, or with pcDNA3 plasmid containing cDNA for the p75 TNF receptor and a pcDNA3 plasmid listed in Tables IV and V.

The results shown in Tables IV and V demonstrate:
a) that clone 10 transfection does not activate NF-κB induction, while NIK strongly does (Table IV), and
b) that clone 10 as well as NIK in which the active site lysine was replaced with alanine (NIK*) strongly inhibited NF-κB induction by the cDNA listed in the first column of Table IV.

Deletion of the 3' UTR of NIK (NIK-3'UTR) greatly increased its expression and consequently its ability to block NF-κB induction when expressed in the mutated form.

TABLE IV

Activation of NF-κB by NIK.

| transfected cDNA | counts | area (mm²) |
|---|---|---|
| empty vector | 327 | 70.7 |
| TRAF2 | 3411 | 70.7 |
| NIK | 6532 | 70.7 |
| clone 10 | 343 | 70.7 |

Gel-retardation assay. Numbers are counts of radioactivity decay events as detected by 'phosphoimager' plate.

TABLE V

Dominant-negative effect of clone 10, NIK K –> A mutant on induction of NF-κB by overexpression of TRAF2, TRADD, MORT1/FADD, TNFR-I, TNFR-II, TNFR-I/FAS chimera, RIP and activation of NF-κB by NIK.

| Inducer of NF-κB | empty vector | NIK | NIK-3'UTR | clone 10 | NIK* | NIK*-3'UTR | TRAF2 225-501 aa |
|---|---|---|---|---|---|---|---|
| TRAF2 | 300 | 1000 | | 25 | 30 | | ND |
| TRADD | 300 | 800 | 1000 | 100 | 100 | 5 | ND |
| MORT1/FADD | 300 | 1000 | | 25 | 80 | | 90 |
| TNFR-I | 200 | 800 | 1000 | 50 | 100 | 5 | ND |
| TNFR-II | 200 | 750 | 800 | 20 | 90 | 6 | ND |
| FAS chimera | 300 | 1200 | | 25 | 50 | | 30 |
| RIP | 300 | 800 | | 75 | 50 | | ND |
| NIK | 500 | | | 100 | | 10 | ND |
| TNF | 200 | | | 80 | | | |
| RelA | 1000 | ND | ND | 1000 | ND | ND | ND |

Luciferase test.

Example 5

Additional Characteristics of NIK

In addition to the specificity tests of Example 2 above, further two-hybrid testing of the binding properties of NIK revealed (results not shown) that the initially isolated partial clone of NIK (NIK 624-947) binds specifically to the C-terminal region of TRAF2 (C-TRAF domain), while, in contrast, the full-length NIK bound to both the C-TRAF domain and a region upstream of it (N-TRAF domain). NIK also does not bind to TRAF3. Further, a chimeric molecule containing the C-TRAF domain of TRAF2 and the N-terminal portion of TRAF3 could bind the partial NIK molecule (NIK 624-947) but not the full-length NIK indicating that the binding of full-length NIK to TRAF2 requires both the C-TRAF and N-TRAF domains of TRAF2.

Moreover, NIK does not self-associate, nor does it bind to the intracellular domains of the: p55 and p75 TNF receptors; the CD40 receptor (a member of the TNF/NGF receptor family); and the FAS/APO1 (CD95 receptor). NIK also does not bind to the intracellular proteins associated with these receptors, such as for example TRADD, MORT1 and RIP. These results correlate with those shown in Table II above concerning the binding specificities of the proteins encoded by clones 9, 10 and 15. The various interactions between the various receptors and proteins are depicted schematically in FIGS. 2A and 2B, FIG. 2B being more complete.

Northern blot analysis revealed that there is a single transcript of NIK expressed in various tissues at different levels, which transcript has a size of about 5000 nucleotides which is essentially the same as the cloned NIK cDNA (as noted above, see FIGS. 6A-G).

Furthermore, as noted above in respect of the protein encoded by clone 10 (originally designated NMPI), the full-length NIK protein also has a serine/threonine protein kinase motif similar to several MAP kinase kinase kinases (MAP-KKK) as also arises from the sequence alignments shown in FIGS. 7A-BB.

In vitro testing of NIK kinase activity revealed that NIK can be autophosphorylated, but not when the active-site lysine and adjacent lysine are replaced with alanine (NIK analog or mutein designated NIK KK429-430AA indicating that the lysines in positions 429 and 430 are replaced with alanines). This also correlates with the above results set forth in Example 4 and shown in Table IV with respect to the NIK* mutein.

As mentioned above, overexpression of NIK in 293 EBNA cells induced NF-κB to an even greater extent than overexpression of TRAF2, but overexpression of the partial NIK (NIK 624-947) did not bring about NF-κB activation. In addition, the above noted NIK analog/mutein NIK KK429-430AA also did not bring about NF-κB activation when overexpressed in these cells. Thus, induction of NF-κB by NIK depends on an intace kinase function of NIK. In contrast, RIP (see FIGS. 2A-B) which also has a kinase domain can still induce NF-κB activation when its kinase activity is abolished by mutation.

The activation of NF-κB upon overexpression of NIK was indistinguishable from that produced by treating the cells with TNF, and as with TNF or TRAF2 overexpression, the principal components of NIK-activated NF-κB were p50 and p65. NIK overexpression caused the degradation of IκBα and blocking this degradation with N-acetyl-Leu-Leu-norleucinol (ALLN) resulted (as with TNF) in the accumulation of IκB molecules having slower SDS-PAGE migration indicative of phosphorylated IκBα.

Other tests have revealed that NF-κB can be activated in 293-EBNA cells by TNF as well as by overexpression of p55 and p75 TNF receptors, or overexpression of a p55 TNF receptor in which the intracellular domain of the p55 TNF receptor is replaced by that of the FAS/APO1 receptor. NF-κB can also be activated by overexpression of TRAF2, TRADD, RIP or MORT1, but not by a MORT1 deletion mutant lacking the region upstream of the 'death domain' of MORT1. As noted above, full length NIK, but not the NIK mutein NIK KK429-430AA nor the partial NIK (NIK 624-947), induces NF-κB activation. Moreover, expression of the NIK KK429-430AA mutein or NIK 624-947 in 293-EBNA cells together with any of the other above noted agents, i.e., the receptors or associated proteins resulted in the blocking of induction of NF-κB activation by all of these agents, indicating that NIK activity is directly involved in this NF-κB induction. Likewise the above observed inhibition by inactive NIK molecules correlates with less IκB reduction.

NF-κB is also activated by IL-1 (see scheme in FIG. 2B). This effect is apparently independent of TRAF2 (IL-1 does not bind TRAF2 and the IL-1 effect is not blocked by the expression of a TRAF2 dominant-negative mutant). However, this IL-1 effect is inhibited by the expression of NIK mutants. In addition, the NF-κB activity observed upon overexpression of the p65 Rel homologue in 293-EBNA cells was unaffected by co-expression of kinase-deficient NIK mutants, indicating that NIK does not affect the function of Rel proteins directly, but participates in their receptor-induced activation.

The cytotoxic activity of TNF (apparently mediated by MORT1-associated protease MACH—see FIG. 2B) is subject to negative regulation by some NF-κB-inducible genes. The antagonizing consequences of NF-κB-mediated gene induction and MACH activation may explain why TNF itself, as well as IL-1 can induce cellular resistance to TNF cytotoxicity. In line with this, it has also been found in accordance with the present invention that the expression of NIK dominant-negative mutants in 293-EBNA cells significantly increased their susceptibility to killing by TNF, and that overexpression of native (full-length, wild-type) NIK inhibited the killing of the cells by TNF or by overexpression of the p55 TNF receptor (this receptor has an intracellular domain containing a 'death domain' region that when expressed in cells, in the absence of any TNF, can induce on its own cell cytotoxicity—see above referred-to publications of present inventors and co-owned, co-pending applications).

Example 6

Further Functional Tests for NIK Biological Activity

In accordance with the present invention, it has also been found that expression of NIK dominant-negative mutants could also block the induction of NF-κB activation in 293-EBNA cells by other inducing agents including: (i) the well known bacterial endotoxin, lipopolysaccharide (LPS); (ii) a well known forbol myristate acetate, which is a known protein kinase C activator; and (iii) the HTLV-1 protein TAX.

Furthermore, the expression of dominant-negative mutants of NIK in the 293-EBNA cells has been found to have essentially no effect on the TNF-induced activation of the Jun kinase indicating that NIK acts in a specific and possibly direct manner to enhance the phosphorylation of IκB without affecting the MAP kinases involved in Jun phosphorylation.

In view of all of the above mentioned it arises that the kinase activity of NIK is part of a signaling cascade that is responsible for NF-κB activation and which cascade is common to the two TNF receptors, the FAS/APO1 receptor and the IL-1-receptor. NIK appears to play a specific role in this cascade. The binding of NIK to TRAF2 may serve to enable NIK to be affected by both the TNF receptors and the FAS/APO1 receptor. By analogy to the MAP kinase cascades, NIK may serve as a substrate for a kinase (MAPKKKK) upon being recruited by TRAF2 to the stimulated receptors, so that when NIK is phosphorylated it phosphorylates and activates other kinases (or may induce directly NF-κB activation by direct phosphorylation of IκB). The IL-1-induced NF-κB activation is independent of TRAF2 and hence the activation of NIK by the IL-1-receptor may be mediated by another protein IRAK, a serine/threonine kinase that is recruited to the IL-1 receptor after stimulation (Cao et al., 1996b), and also by TRAF6 which binds IRAK (see Cao et al., 1996a, as well as scheme in FIG. 2B). As noted above, the target of NIK, or of a cascade of kinases activated by it, is likely to be IκB. NIK may also phosphorylate TRAF proteins or regulatory proteins that bind to them for example TANK-I/TRAF (see Cheng and Baltimore, 1996; Rothe et al., 1996) creating docking sites for other proteins

REFERENCES

1. Adelman et al., (1983) DNA 2, 183.
2. Alnemri, E. S. et al. (1995) J. Biol. Chem. 270, 4312-4317.
3. Ausubel, F. M. et al. eds., Current Protocols in Molecular Biology.
4. Baeuerle, P. A., and Henkel, T. (1994) Annu Rev Immunol.
5. Bazan, J. F. (1993). Current Biology 3, 603-606.
6. Berberich, I., Shu, G. L., and Clark, E. A. (1994). J Immunol 153, 4357-66.
7. Beutler, B., and van Huffel, C. (1994). Science 264, 667-8.
8. Blank, V., Kourilsky, P., and Israel, A. (1992). Trends Biochem. Sci 17, 135-40.
9. Boldin, M. P. et al. (1995a) J. Biol. Chem. 270, 337-341.
10. Boldin, M. P., Varfolomeev, E. E., Pancer, Z., Mett, I. L., Camonis, J. H., and Wallach, D. (1995b). J. Biol. Chem. 270, 7795-7798.
11. Boldin, M. P. et al. (1996) Cell 85, 803-815.
12. Cao, Z. et al. (1996a) Nature 383, 443-446.
13. Cao, Z. et al. (1996b) Science 271, 1128-1131.
14. Chen, C. J. et al. (1992) Ann. N.Y. Acad. Sci. 660:271-273.
15. Cheng, G., Cleary, A. M., Ye, Z-s., Hong, D. I., Lederman, S, and Baltimore, D. (1995) Science 267:1494-1498).
16. Cheng, G. and Baltimore, D. (1996) Genes Dev. 10, 963-973.
17. Chinnalyan, A. M., O'Rourke, K., Tewari, M., and Dixit, V. M. (1995) Cell 81, 505-512.
18. Creighton, T. E., Proteins: Structure and Molecular Properties, W.H. Freeman & Co., San Francisco, Calif. 1983.
19. Croston, G. E., Cao, Z., and Goeddel, D. V. (1995). J Biol Chem 270, 16514-7.
20. DiDonato, J. A., Mercurio, F., and Karin, M. (1995). Mol Cell Biol 15, 1302-11.
21. Durfee, T. et al. (1993) Genes Dev. 7:555-569.
22. Field, J. et al. (1988) Mol. Cell. Biol. 8:2159-2165.
23. Geysen, H. M. (1985) Immunol. Today 6, 364-369.
24. Geysen, H. M. et al. (1987) J. Immunol. Meth. 102, 259-274.
25. Gilmore, T. D., and Morin, P. J. (1993). Trends Genet 9, 427-33.
26. Gossen, M. and Bujard, M. (1992) PNAS 89:5547-5551.
27. Grell, M., Douni, E., Wajant, H., Lohden, M., Clauss, M., Baxeiner, B., Georgopoulos, S., Lesslauer, W., Kollias, G., Pfizenmaier, K., and Scheurich, P. (1995). Cell 83, 793-802.
28. Grilli, M., Chiu, J. J., and Lenardo, M. J. (1993). Int RevCytol.
29. Hanks, S. K., Quinn, A. M., and Hunter, T. (1988). Science 241, 42-52.
30. Howard, A. D. et al. (1991) J. Immunol. 147, 2964-2969.
31. Hsu, H., Shu, H.-B., Pan, M.-G., and Goeddel, D. V. (1996). Cell 84, 299-308.
32. Hsu, H., Xiong, J., and Goeddel, D. V. (1995). Cell 81, 495-504.
33. Kaufmann, S. H. (1989) Cancer Res. 49, 5870-5878.
34. Kaufmann, S. H. (1993) Cancer Res. 53, 3976-3985.
35. Lalmanach-Girard, A. C., Chiles, T. C., Parker, D. C., and Rothstein, T. L. (1993). J Exp Med 177, 1215-1219.
36. Lazebnik, Y. A. et al. (1994) Nature 371, 346-347.
37. Mashima, T. et al. (1995) Biochem. Biophys. Res. Commun. 209, 907-915.
38. McDonald, P. P., Cassatella, M. A., Bald, A., Maggi, E., Romagnani, S., Gruss, H. J., and Pizzolo, G. (1995). Eur J Immunol 25, 2870-6.
39. Messing et al., Third Cleveland Symposium on Macromolecules and Recombinant DNA, Ed. A. Walton, Elsevier, Amsterdam (1981)
40. Milligan, C. E. et al. (1995) Neuron 15, 385-393.
41. Mosialos, G., Birkenbach, M., Yalamanchili, R., VanArsdale, T., Ware, C., and Kieff, E. (1995). Cell 80, 389-399.

42. Muranishi, S. et al. (1991) Pharm. Research 8, 649.
43. Nagata, S. and Golstein, P. (1995) Science 267, 1449-1456.
44. Rensing-Ehl, A., Hess, S., Ziegler-Heitbrock, H. W. L., Riethmüller, G., and Engelmann, H. (1995). J. Inlamm. 45, 161-174.
45. Rothe, M., Pan, M.-G., Henzel, W. J., Ayres, T. M., and Goeddel, D. V. (1995b). Cell 83, 1243-1252.
46. Rothe, M., Sarma, V., Dixit, V. M., and Goeddel, D. V. (1995a). Science 269, 1424-1427.
47. Rothe, M., Wong, S. C., Henzel, W. J., and Goeddel, D. V. (1994). Cell 78, 681-692.
48. Rothe, M. et al. (1996) Proc. Natl. Acad. Sci. U.S.A. 93, 8241-8246.
49. Ruzicka et al., (1993) Science 260, 487.
50. Sambrook et al. (1989) Molecular cloning: a laboratory manual, Cold Spring Harbor Laboratory Press, Cold Spring Harbor, N.Y.
51. Sano et al., (1992) Science 258, 120.
52. Sano et al., (1991) Biotechniques 9, 1378.
53. Schreiber, E., Matthias, P., Muller, M. M. and Schaffner, W. (1989), Nuc. Acids Res. 17:6419.
54. Schulz et al., G. E., Principles of Protein Structure, Springer-Verlag, New York, N.Y. 1798.
55. Sleath, P. R. et al. (1990) J. Biol. Chem. 265, 14526-14528.
56. Smith, C. A., Farrah, T., and Goodwin, R. G. (1994). Cell 76, 959-962.
57. Stanger, B. Z. et al. (1995) Cell 81, 513-523.
58. Thornberry, N. A. et al. (1992) Nature 356, 768-774.
59. Thornberry, N. A. et al. (1994) Biochemistry 33, 3934-3940.
60. Vandenabeele, P., Declercq, W., Beyaert, R., and Fiers, W. (1995). Trends Cell Biol. 5, 392-400.
61. Varfolomeev, E. E., Boldin, M. P., Goncharov, T. M., and Wallach, D. (1996). J. Exp. Med. in press.
62. Vassalli, P. (1992) Ann. Rev. Immunol. 10, 411-452.
63. Veira et al., (1987) Meth. Enzymol. 153, 3.
64. Wallach, D. (1996) Eur. Cytokine Net. 7, 713-724.
65. Wang, L. et al. (1994) Cell 78, 739-750.
66. Wilks, A. F. et al. (1989) Proc. Natl. Acad. Sci. USA, 86:1603-1607.
67. Zaccharia, S. et al. (1991) Eur. J. Pharmacol. 203, 353-357.
68. Zhao, J. J. and Pick, L. (1993) Nature 365: 448-451.

The invention claimed is:

1. An isolated polypeptide that binds to TRAF2, said polypeptide comprising:
   a) the amino acid sequence of SEQ ID NO:2, the amino acid sequence encoded by the nucleotide sequence of SEQ ID NO:3, or the amino acid sequence of SEQ ID NO:5;
   b) the amino acid sequence of a fragment of a), which fragment binds to TRAF2 and comprises a serine/threonine protein kinase motif of (a);
   c) the amino acid sequence of an analog of a), said analogue differing from a) by not more than five amino acid changes, each such change being a conservative substitution, which analog binds to TRAF2; or
   d) a derivative of a), b) or c) which binds to TRAF2, said derivative selected from the group consisting of glycosylation or phosphorylation of an amino acid side chain or an N- or C-terminal, aliphatic esters of the carboxyl groups, amides of the carboxyl groups by reaction with ammonia or with primary or secondary amines, N-acyl derivatives or free amino groups of the amino acid residues formed with acyl moieties and O-acyl derivatives of free hydroxyl group formed with acyl moieties.

2. An isolated polypeptide in accordance with claim 1, wherein said polypeptide is NIK (SEQ ID NO:7).

3. A pharmaceutical composition comprising, as active ingredient at least one polypeptide according to claim 1.

4. A method for the treatment of a pathological condition associated with TRAF2, said method comprising administering to a patient in need an effective amount of a polypeptide according to claim 1.

5. A method for screening of a ligand capable of binding to a polypeptide according to claim 1 comprising contacting an affinity chromatography matrix to which said polypeptide is attached with a cell extract whereby the ligand is bound to said matrix, and eluting, isolating and analyzing said ligand.

6. A method for identifying and producing a ligand capable of binding to a polypeptide according to claim 1, comprising:
   a) screening for a ligand capable of binding to the NIK sequence of SEQ ID NO:7;
   b) identifying and characterizing a ligand, other than TRAF2 or portions of a receptor of the TNF/NGF receptor family, found by said screening step to be capable of said binding; and c) producing said ligand in substantially isolated and purified form.

7. A method for identifying and producing a molecule capable of binding to a polypeptide according to claim 1, comprising:
   a) screening for a molecule capable of binding to a polypeptide according to claim 1;
   b) identifying and characterizing said molecule; and
   c) producing said molecule in substantially isolated and purified form.

8. The isolated polypeptide of claim 1, wherein said sequence
   b) differs from a) by omission of not more than 70 consecutive amino acids from the N- or C-terminal of a).

9. The isolated polypeptide of claim 1, wherein said sequence b) differs from a) by omission of not more than 10 consecutive amino acids from the N- or C-terminal of a).

* * * * *